United States Patent [19]
Kordis et al.

[11] Patent Number: 5,549,661
[45] Date of Patent: Aug. 27, 1996

[54] SYSTEMS AND METHODS FOR CREATING COMPLEX LESION PATTERNS IN BODY TISSUE

[75] Inventors: Thomas F. Kordis, Sunnyvale; David K. Swanson, Mountain View; Jerome Jackson, Sunnyvale; Terry E. Spraker, Portolla, all of Calif.

[73] Assignee: EP Technologies, Inc., Sunnyvale, Calif.

[21] Appl. No.: 566,291

[22] Filed: Dec. 1, 1995

Related U.S. Application Data

[63] Continuation of Ser. No. 137,580, Oct. 15, 1993, abandoned.

[51] Int. Cl.$^6$ .................................................... A61N 1/06
[52] U.S. Cl. ................................................. 607/99; 128/642
[58] Field of Search ............................... 128/642; 607/98, 607/99, 122, 125, 126

[56] References Cited

U.S. PATENT DOCUMENTS

| | | |
|---|---|---|
| 2,245,880 | 6/1941 | Tipton et al. . |
| 3,230,957 | 1/1966 | Seifert . |
| 4,481,953 | 11/1984 | Gold et al. . |
| 4,522,212 | 6/1985 | Gelinas et al. . |
| 4,532,880 | 8/1985 | Auth et al. . |
| 4,552,212 | 6/1985 | Gelinas et al. ........................... 128/642 |
| 4,641,649 | 2/1987 | Walinski et al. . |
| 4,643,186 | 2/1987 | Rosen et al. . |
| 4,660,571 | 4/1987 | Hess et al. . |
| 4,677,990 | 7/1987 | Neubauer . |
| 4,699,147 | 10/1987 | Chilson et al. ........................... 128/642 |
| 4,724,836 | 2/1988 | Okada . |
| 4,759,378 | 7/1988 | Swendson et al. . |
| 4,765,331 | 8/1988 | Petruzzi et al. . |
| 4,892,102 | 1/1990 | Astrinsky ................................. 128/642 |
| 4,913,142 | 4/1990 | Kittrell et al. . |
| 5,057,106 | 10/1991 | Kasevich et al. . |
| 5,101,836 | 4/1992 | Lee . |
| 5,117,828 | 6/1992 | Metzger et al. ........................... 128/642 |
| 5,150,717 | 9/1992 | Rosen et al. . |
| 5,186,171 | 2/1993 | Kurhy . |
| 5,192,280 | 3/1993 | Parins . |
| 5,197,963 | 3/1993 | Parins . |
| 5,215,103 | 6/1993 | Desai . |
| 5,228,442 | 7/1993 | Imran ........................................ 128/642 |
| 5,237,996 | 8/1993 | Waldman et al. ....................... 128/642 |
| 5,255,679 | 10/1993 | Imran ........................................ 128/642 |
| 5,263,493 | 11/1993 | Avitall ...................................... 607/122 |
| 5,265,623 | 11/1993 | Kroll et al. . |
| 5,293,869 | 3/1994 | Edwards et al. ......................... 128/642 |
| 5,311,866 | 5/1994 | Kagan et al. ............................. 128/642 |
| 5,313,943 | 5/1994 | Houser et al. . |
| 5,324,284 | 6/1994 | Imran . |
| 5,327,889 | 7/1994 | Imran ........................................ 128/642 |
| 5,327,905 | 7/1994 | Avitall . |
| 5,345,936 | 9/1994 | Pomeranz et al. . |
| 5,397,341 | 3/1995 | Hirschberg et al. ..................... 128/642 |

FOREIGN PATENT DOCUMENTS

| | | |
|---|---|---|
| 0317489 | 11/1988 | European Pat. Off. . |
| WO89/06148 | 1/1989 | WIPO . |
| WO93/04734 | 9/1991 | WIPO . |

OTHER PUBLICATIONS

Radiofrequency Catheter Ablation of Atrial Arrhythmias Results and Mechanisms; M, Leah MD; pp. 1074–1089, Mar. 94.

Catheter Ablation of Atrial Flutter Using Radiofrequency Energy; H. Calkins et al., p. 2879, Oct. 1992.

(List continued on next page.)

*Primary Examiner*—Krista M. Zele
*Assistant Examiner*—Brian L. Caster
*Attorney, Agent, or Firm*—Ryan, Maki, Mann & Hohenfeldt

[57] ABSTRACT

Systems and methods form curvilinear lesions in tissue within the body. The systems and methods expose tissue to electrode arrays with intersecting energy emitting elements. The systems and methods apply ablating energy for emission by the elements to create intersecting curvilinear lesion patterns in the tissue.

40 Claims, 31 Drawing Sheets

OTHER PUBLICATIONS

Radiofrequency Catheter Ablation for the Treatment of Human Type 1 Atrial Flutter; Identification of a Critical Zone in the Reentrant Circuit by Endocardial Mapping Techniques; G. Feld, Oct. 1992.

Delivery of Radiofrequency Energy to all Four Poles of a Catheter Increases Lesion Size; Sean C. Mackey et al., pp. 3119, Oct. 1992.

Observations on Electrode–Tissue Interface Temperature & Effect on Electrical Impedance During Radiofrequency Ablation of Vantricular Myocardium; D. Haines MD, pp. 1034–1038, Sep. 1990.

Catheter Ablation of the Atrioventicular Junction with Radiofrequency Energy; J. Langberg MD et al., pp. 1527–1535, Dec. 1989.

Atrial Flutter Update on the Mechanism and Treatment; B. Olshansky et al., Dec. 1992.

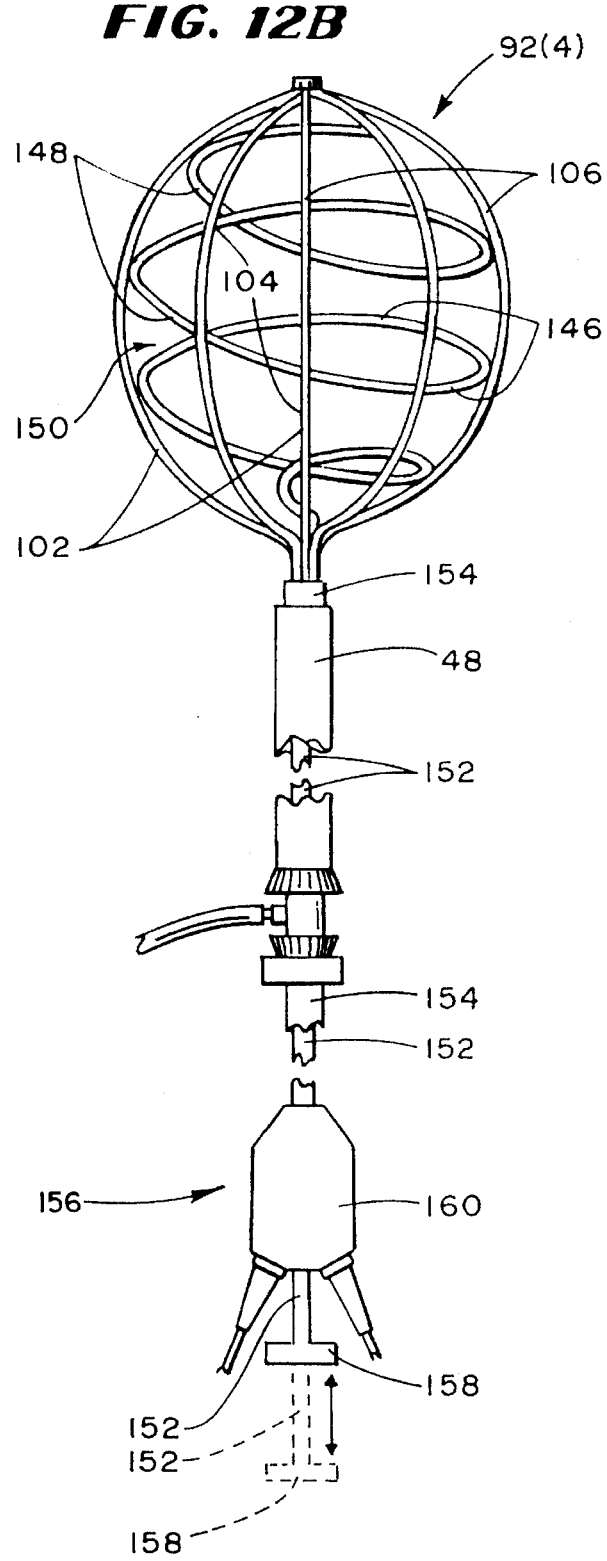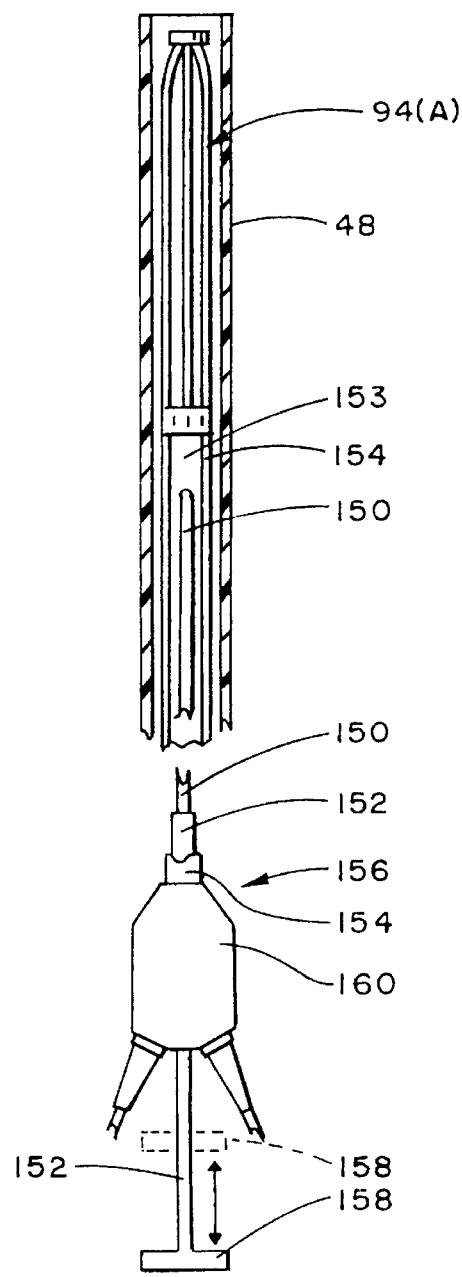

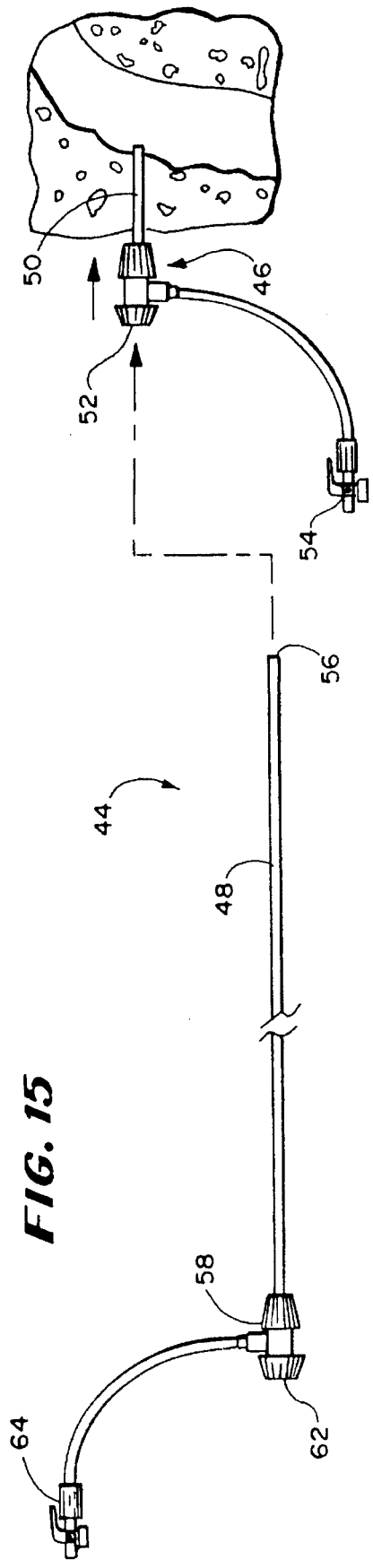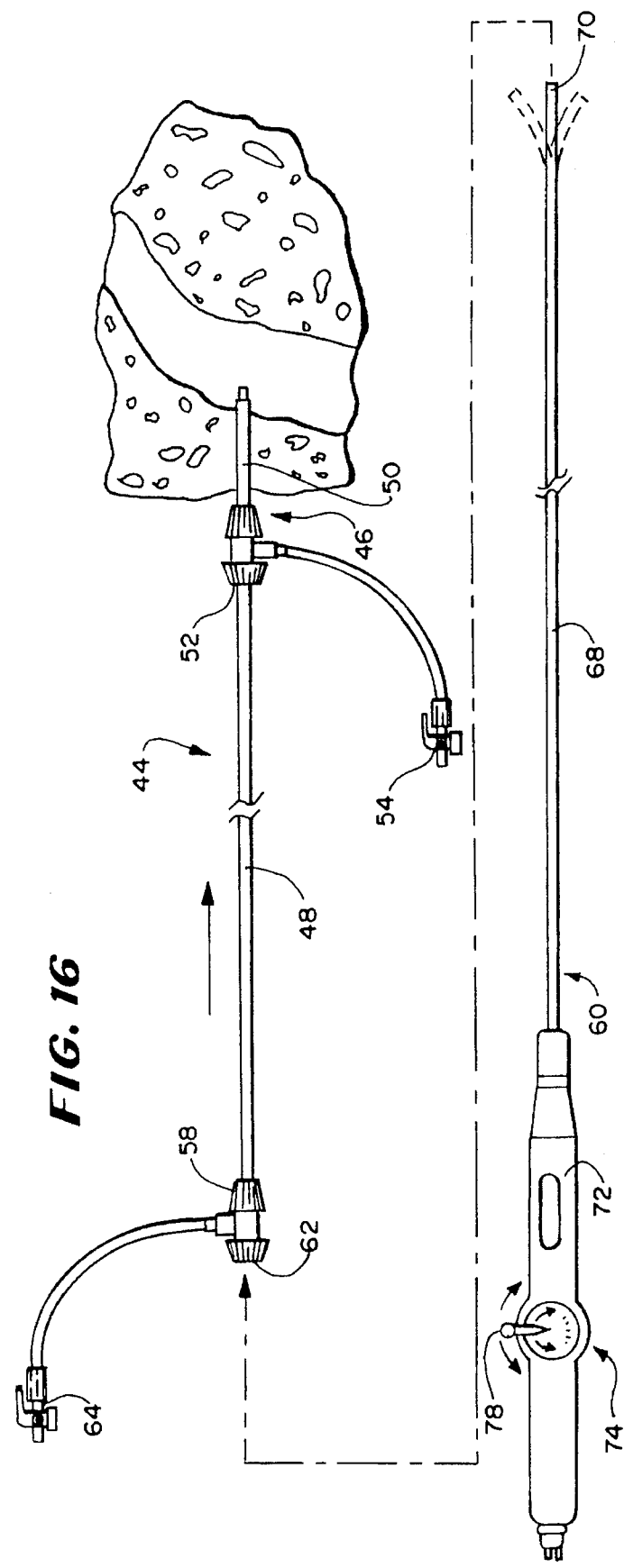

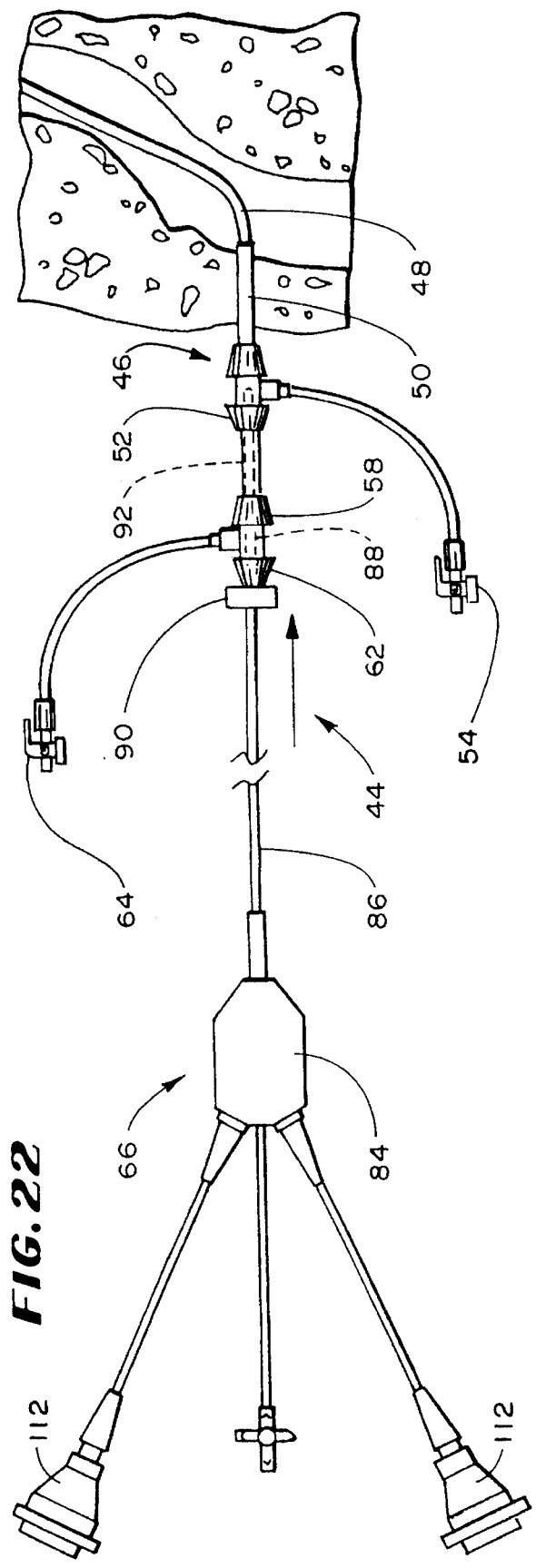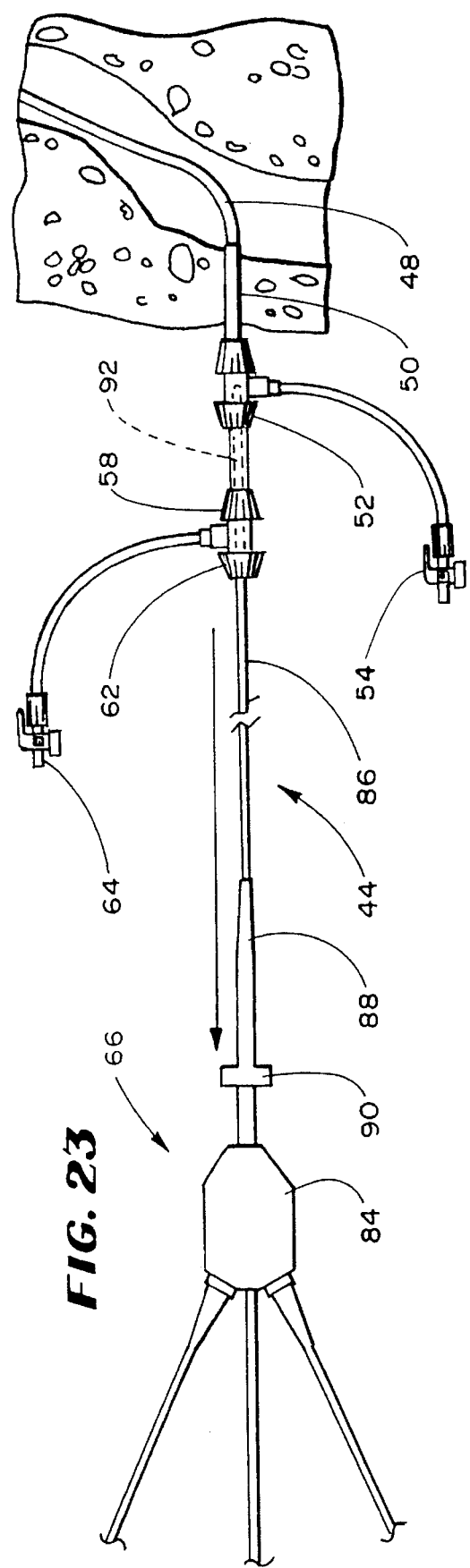
FIG.22
FIG.23

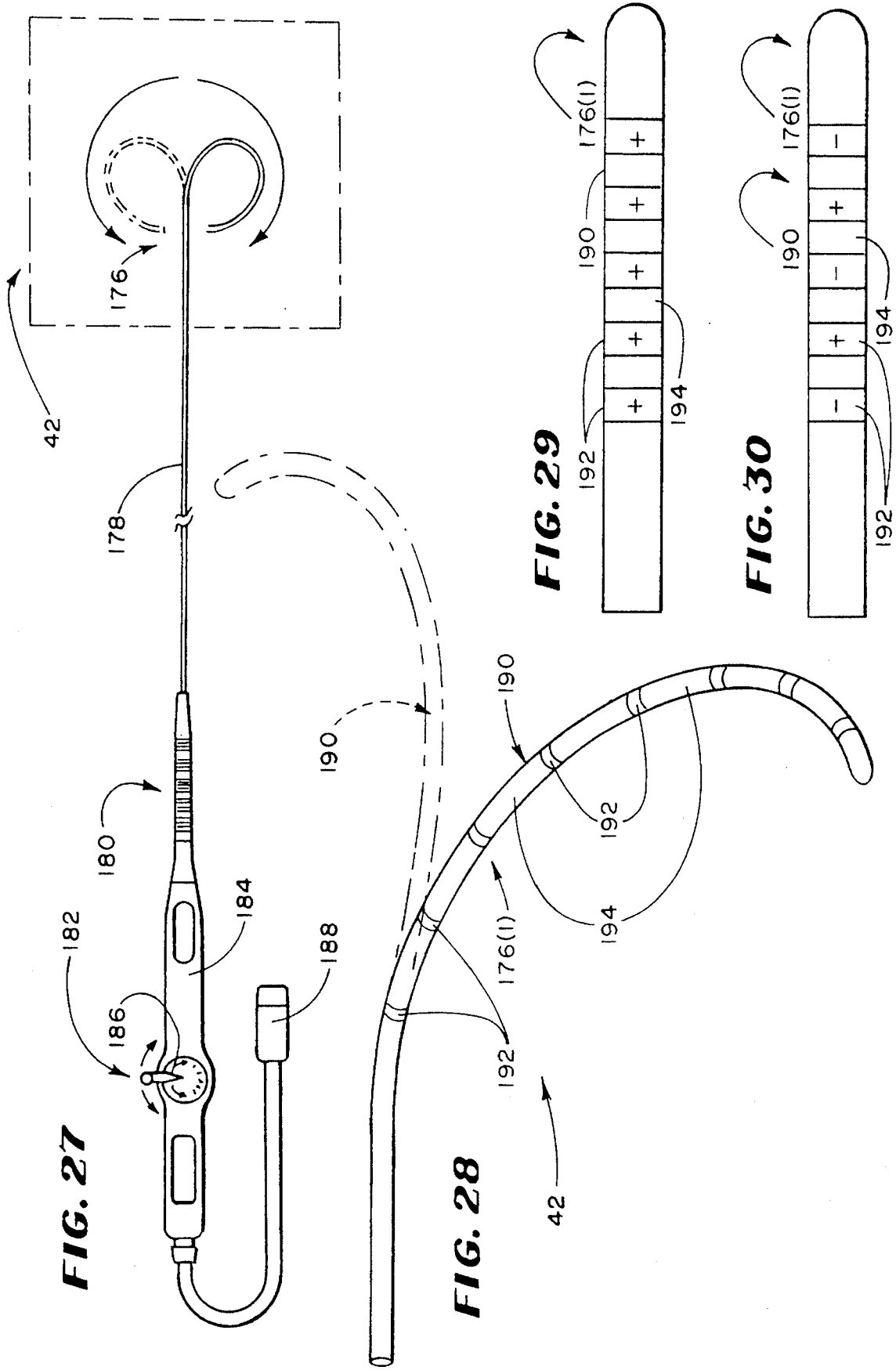

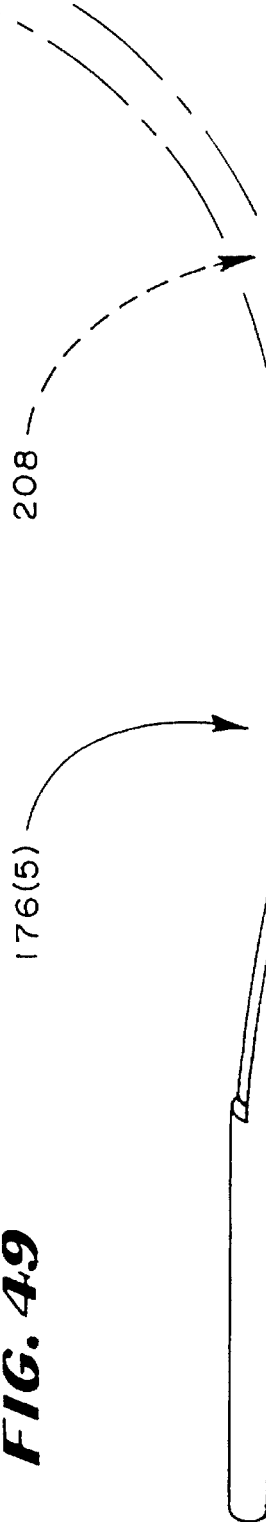
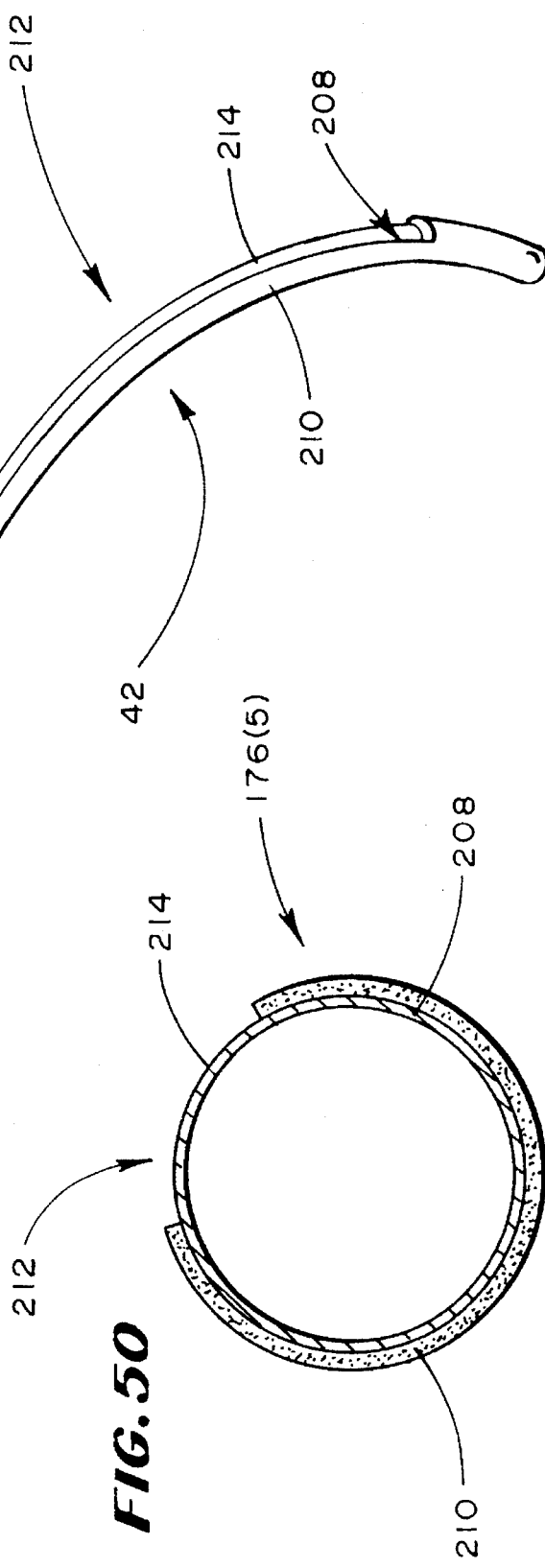
FIG. 49
FIG. 50

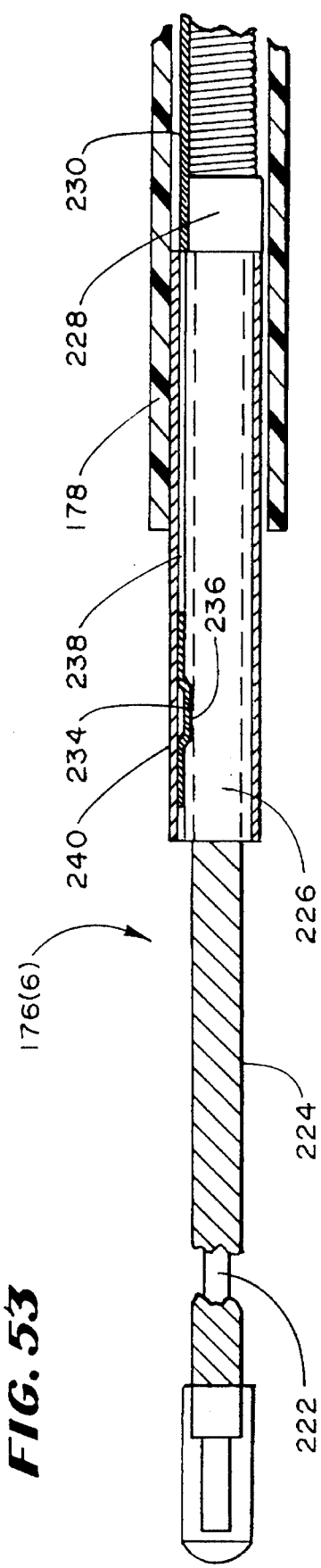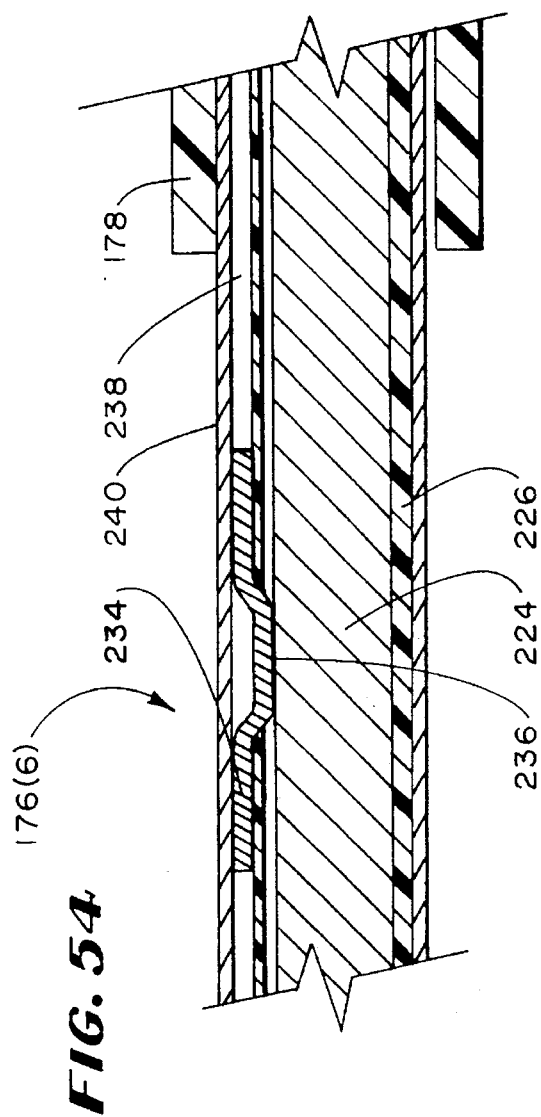

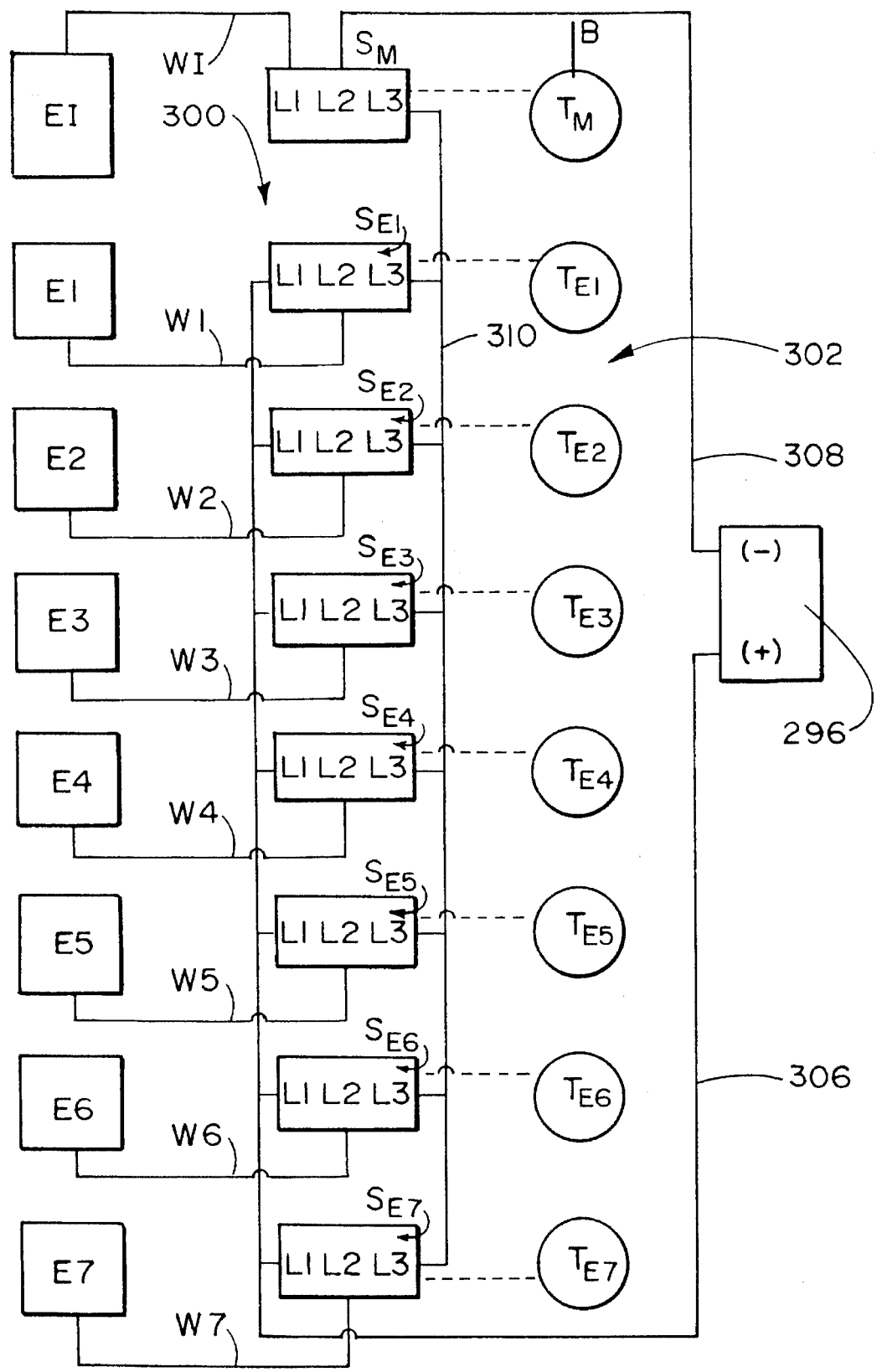
FIG. 62 (OFF)

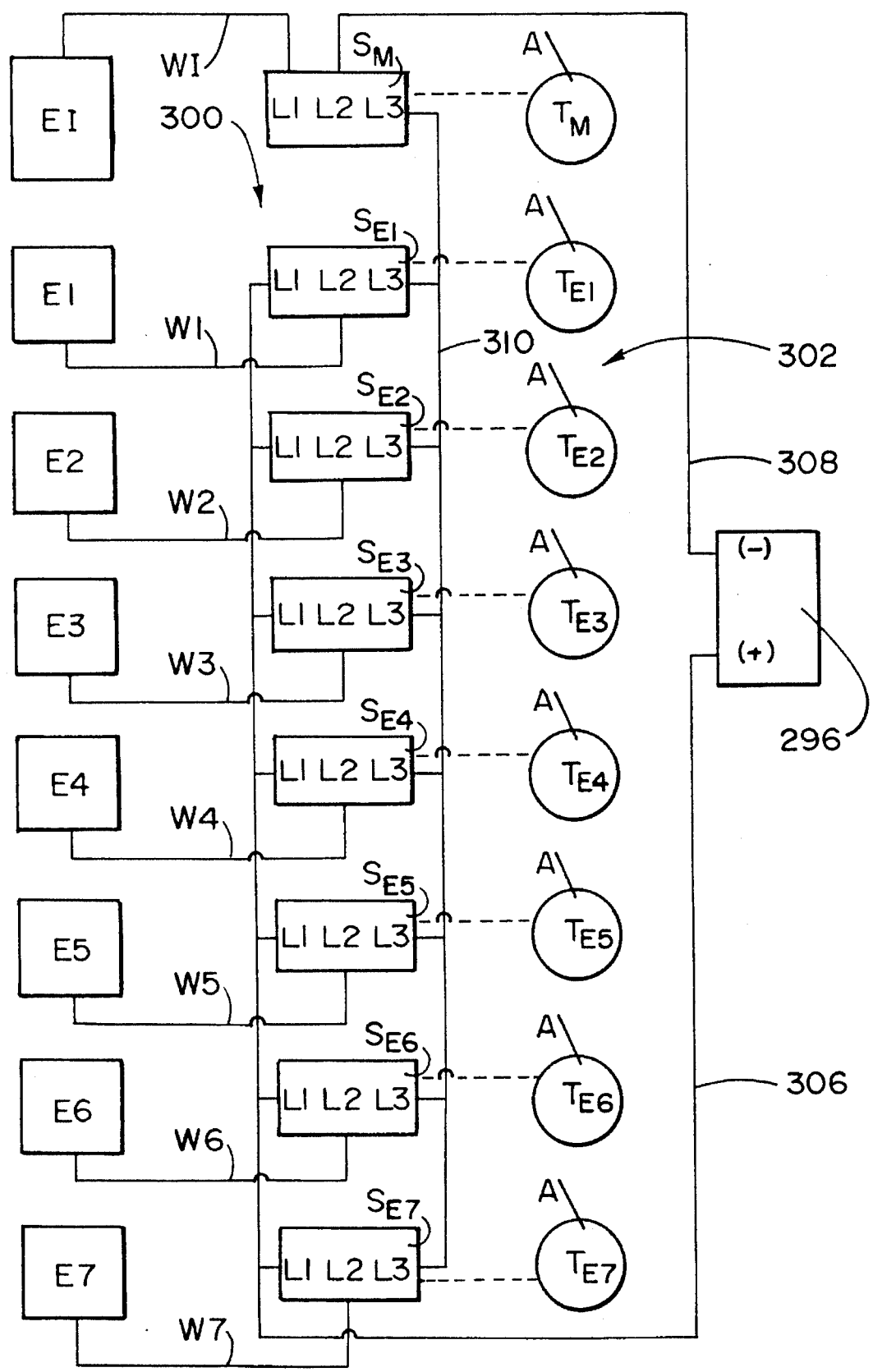
FIG. 63 UNIPOLAR CONTINUOUS

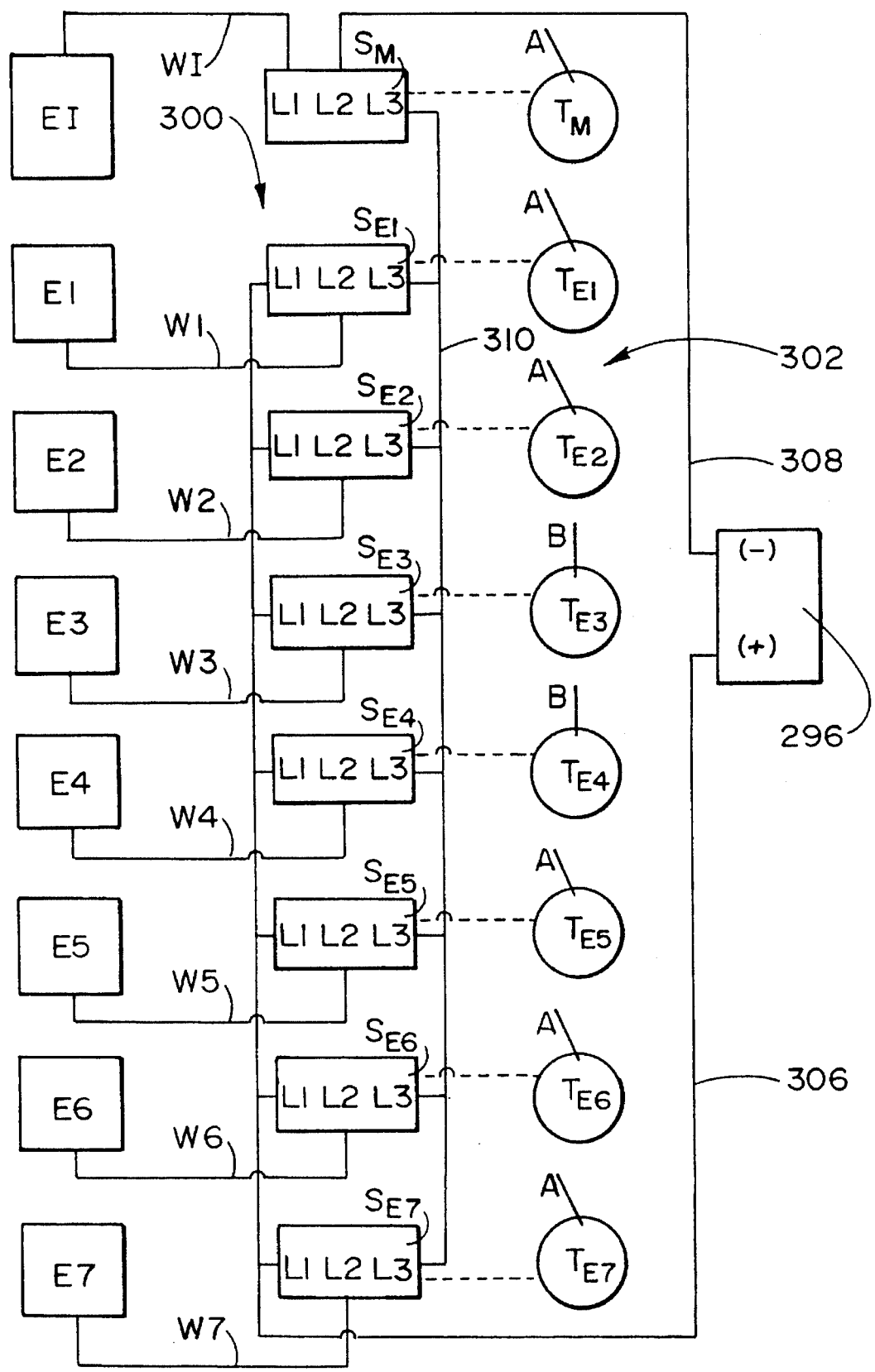
FIG. 64 UNIPOLAR INTERRUPTED

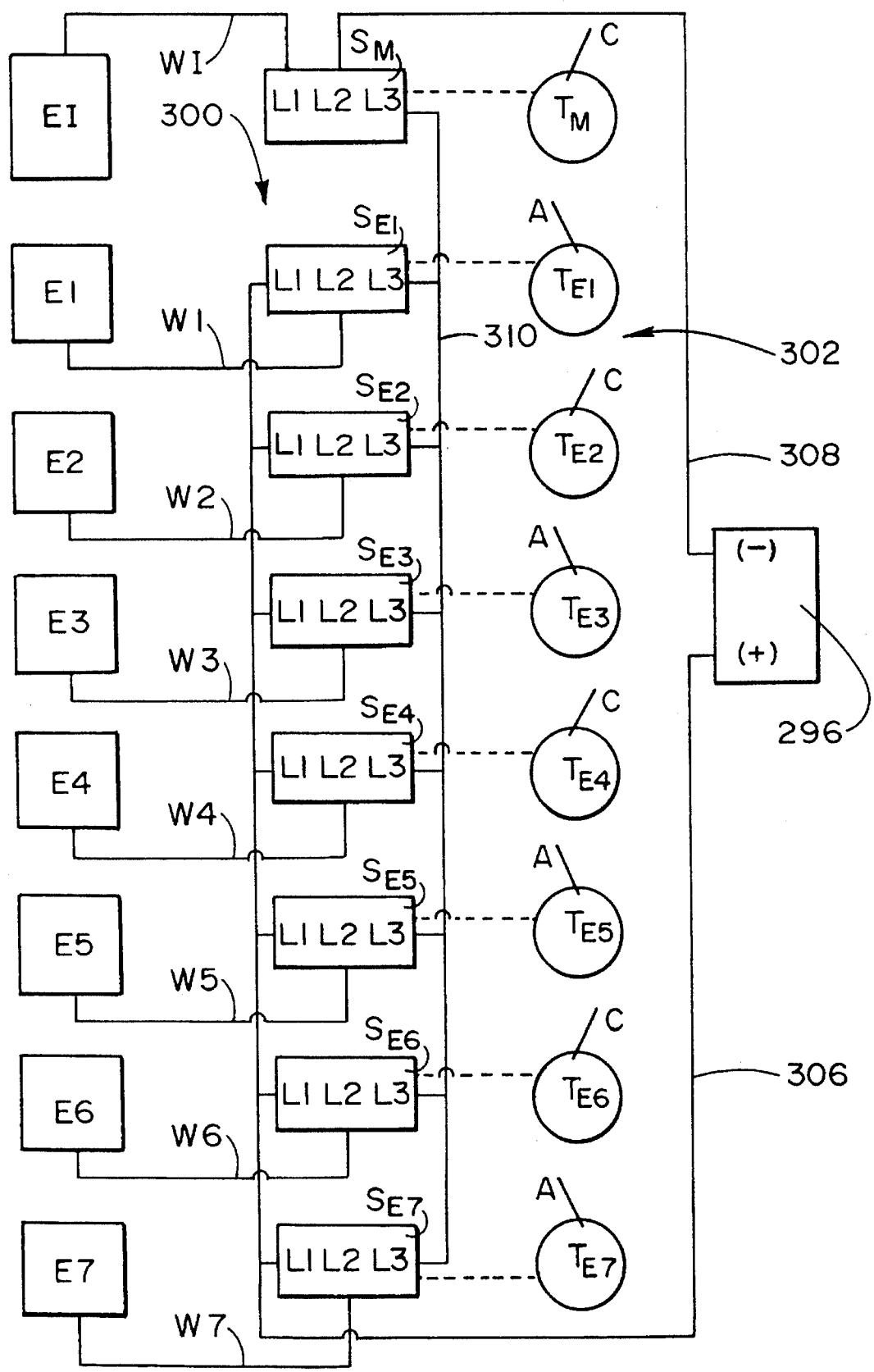
FIG. 65 BIPOLAR CONTINUOUS

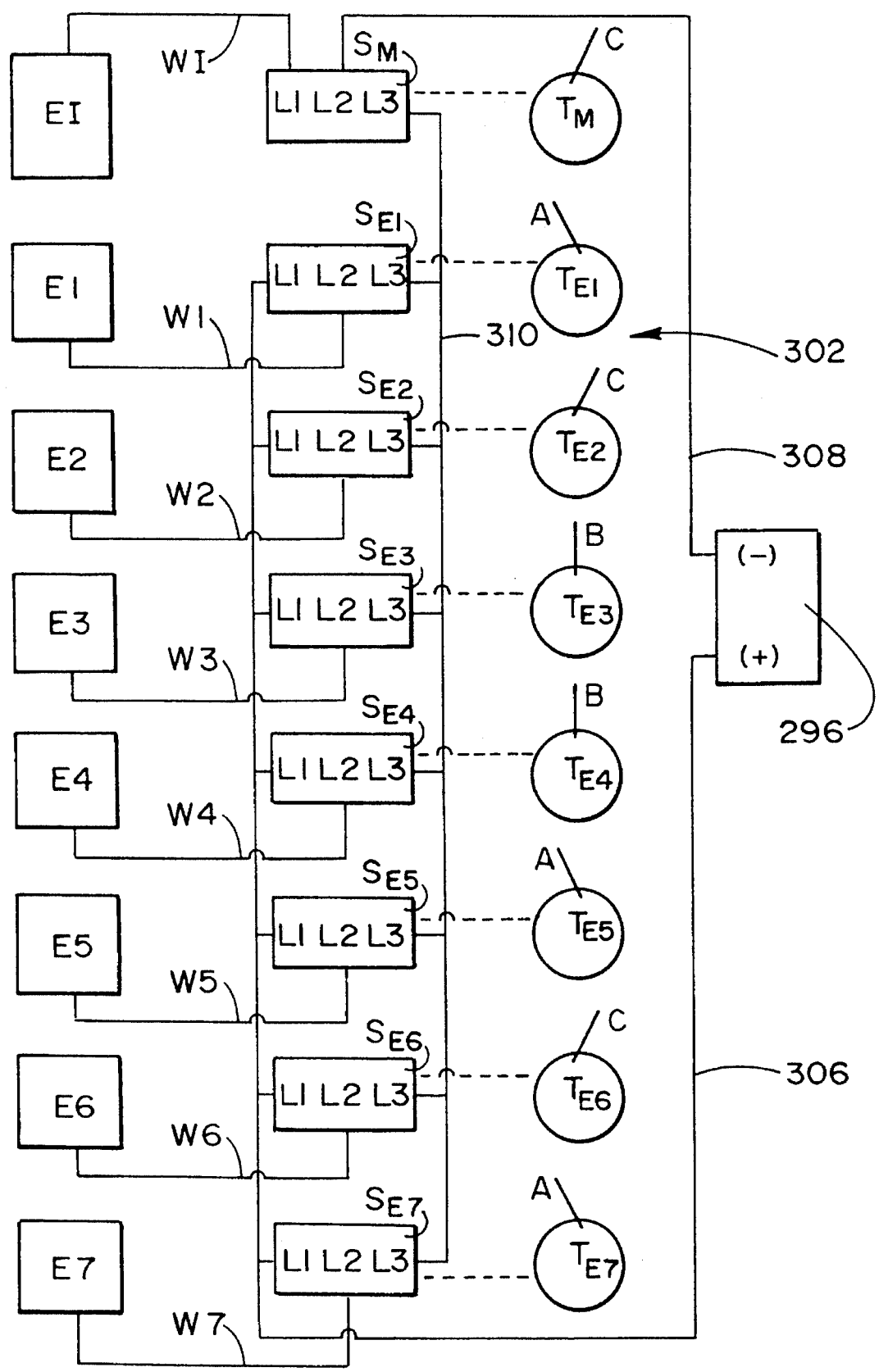
FIG. 66  BIPOLAR INTERRUPTED

SYSTEMS AND METHODS FOR CREATING COMPLEX LESION PATTERNS IN BODY TISSUE

This is a continuation of application Ser. No. 08/137,580 filed on Oct. 15, 1993 now abandoned.

FIELD OF THE INVENTION

In a general sense, the invention is directed to systems and methods for creating lesions the interior regions of the human body. In a more particular sense, the invention is directed to systems and methods for ablating heart tissue for treating cardiac conditions.

BACKGROUND OF THE INVENTION

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract.

The AV node regulates the propagation delay to the atrioventricular bundle (or "HIS" bundle). This coordination of the electrical activity of the heart causes atrial systole during ventricular diastole. This, in turn, improves the mechanical function of the heart.

Atrial geometry, atrial anisotropy, and histopathologic changes in the left or right atria can, alone or together, form anatomical obstacles. The obstacles can disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria. Abnormal, irregular heart rhythm, called arrhythmia, results. This form of arrhythmia is called atrial fibrillation, which is a very prevalent form of arrhythmia.

Today, as many as 3 million Americans experience atrial fibrillation. These people experience an unpleasant, irregular heart beat. Because of a loss of atrioventricular synchrony, these people also suffer the consequences of impaired hemodynamics and loss of cardiac efficiency. They are more at risk of stroke and other thromboembolic complications because of loss of effective contraction and atrial stasis.

Treatment is available for atrial fibrillation. Still, the treatment is far from perfect.

For example, certain antiarrhythmic drugs, like quinidine and procainamide, can reduce both the incidence and the duration of atrial fibrillation episodes. Yet, these drugs often fail to maintain sinus rhythm in the patient.

Cardioactive drugs, like digitalis, Beta blockers, and calcium channel blockers, can also be given to control the ventricular response. However, many people are intolerant to such drugs.

Anticoagulant therapy also combat thromboembolic complications.

Still, these pharmacologic remedies often do not remedy the subjective symptoms associated with an irregular heartbeat. They also do not restore cardiac hemodynamics to normal and remove the risk of thromboembolism.

Many believe that the only way to really treat all three detrimental results of atrial fibrillation is to actively interrupt all the potential pathways for atrial reentry circuits.

James L. Cox, M.D. and his colleagues at Washington University (St. Louis, Mo.) have pioneered an open heart surgical procedure for treating atrial fibrillation, called the "maze procedure." The procedure makes a prescribed pattern of incisions to anatomically create a convoluted path, or maze, for electrical propagation within the left and right atria, therefore its name. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits.

The maze procedure has been found very effective in curing atrial fibrillation. Yet, despite its considerable clinical success, the maze procedure is technically difficult to do. It requires open heart surgery and is very expensive. Because of these factors, only a few maze procedures are done each year.

One objective of the invention is to provide catheter-based ablation systems and methods providing beneficial therapeutic results without requiring invasive surgical procedures.

Another objective of the invention is to provide systems and methods that simplify the creation of complex lesions patterns in body tissue, such as in the heart.

SUMMARY OF THE INVENTION

The invention provides new systems and methods for creating specially shaped lesion patterns in body tissue.

One aspect of the invention proves a device comprising first and second energy emitting elements. According to this aspect of the invention, the second energy emitting element intersects the first energy emitting element to form an angled junction between them. When ablating energy is emitted by the first and second elements, they form a lesion pattern that, due to the angled junction, is curvilinear in shape.

Another aspect of the invention provides a device having first, second, and third energy emitting elements. The second energy emitting element intersects the first energy emitting element to form a first angled junction. The third energy emitting element also intersects the first energy emitting element to form a second angled junction. When ablating energy is emitted by the first, second, and third elements, they create an intersecting, compound curvilinear lesion pattern in the body tissue.

According to each aspect of the invention, the curvilinear lesion patterns created are preferably long and thin in shape, having a length that is substantially greater than its width. In these preferred arrangements, the lesion patterns created have a length to width ratio that is at least about 3:1. It width is no greater than about 5 mm.

In these preferred embodiments, the energy emitting elements are mutually resilient for bending relative to each other when exposed to body tissue.

Another aspect of the invention provides an array of main splines extending side by side in a spaced-apart relationship to form a structure for creating curvilinear lesions in tissue within the body. The array comprises at least one bridge spline extending between two main splines. The bridge spline intersects one main spline to form an angled junction.

The one main spline has a first region for emitting energy. The bridge spline likewise has a second region for emitting energy. The first energy emitting region and the second energy emitting region intersect to form an angled junction.

When ablating energy is emitted by the regions, they form an intersecting curvilinear lesion pattern in the body tissue.

In the preferred embodiments, the main splines form a resilient, three-dimensional basket structure that encloses an open interior. In these embodiments, the bridge spline is located either within or outside the open interior of the three-dimensional basket structure.

In one arrangement, the bridge spline is part of a helical structure located within the open interior of the three-dimensional basket structure.

In another arrangement, the bridge spline is steerable within the open interior of the three-dimensional basket structure.

In yet another arrangement, the bridge spline is part of a second three-dimensional structure located within the open interior of the three-dimensional basket structure.

In still another arrangement, the bridge spline comprises a helical structure wrapped about the outside of the three-dimensional basket structure.

Another aspect of the invention provides a method for forming curvilinear lesions in tissue within the body. The method exposes tissue to an electrode array comprising a first energy emitting element and a second energy emitting element that intersects the first energy emitting element to form an angled junction between them. The method applies ablating energy for emission by both elements to create an intersecting curvilinear lesion pattern in the tissue.

Another aspect of the invention provides a method for forming compound curvilinear lesions in tissue within the body. This method exposes tissue to an electrode array comprising a first energy emitting element, a second energy emitting element that intersects the first energy emitting element to form an angled junction between them, and a third energy emitting element that intersects one of the first and second energy emitting elements at a second angled junction spaced from the first mentioned angled junction. The method applies ablating energy for emission by the first, second, and third elements to create an intersecting compound curvilinear lesion pattern.

In a preferred embodiment, the invention provides a catheter-based systems and methods that create lesions in myocardial tissue. In purpose and effect, the systems and methods emulate an open heart maze procedure, but do not require costly and expensive open heart surgery. The systems and methods can be used to perform other curative procedures in the heart as well.

BRIEF DESCRIPTION OF THE DRAWINGS

FIGS. 12A and 12B are plan views of another ablating probe that carries a three-dimensional basket structure that, in use, forms curvilinear lesions within the atria of the heart;

FIGS. 15 to 26 are views of a delivery system that, when used in the manner shown in these Figures, introduces and deploys ablating elements shown in the preceding Figures into the atria of the heart;

FIG. 27 is a plan view of a probe that carries a family of flexible, elongated ablating elements that can be used to emit ablating energy to form curvilinear lesions within the atria of the heart;

FIGS. 28 to 30 are views of one flexible, elongated ablating element that carries a pattern of closely spaced electrically conductive regions that can be used to emit ablating energy to form curvilinear lesions within the atria of the heart;

FIGS. 49 and 50 show a flexible, elongated ablating element that includes an elongated opening that exposes a conductive region that can form curvilinear patterns of lesions in myocardial tissue;

FIGS. 51 to 54 show a flexible, elongated ablating element that carries a wound spiral winding with a sliding sheath that can form curvilinear patterns of lesions in myocardial tissue;

FIG. 62 is a schematic view of the controller shown in FIG. 60 electronically configured in its OFF mode;

FIG. 63 is a schematic view of the controller shown in FIG. 60 electronically configured to provide a continuous, unipolar lesion pattern;

FIG. 64 is a schematic view of the controller shown in FIG. 60 electronically configured to provide an interrupted, unipolar lesion pattern;

FIG. 65 is a schematic view of the controller shown in FIG. 60 electronically configured to provide a continuous, bipolar lesion pattern; and FIG. 66 is a schematic view of the controller shown in FIG. 60 electronically configured to provide an interrupted, bipolar lesion pattern.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

The invention provides systems and methods for ablating tissue inside a living body. The invention creates elongated lesions, which can be either straight or curvilinear. The invention also creates patterns of lesions, which can be either simple or complex.

The invention lends itself to use in many relatively noninvasive catheter-based procedures. In contrast with complex, invasive surgical procedures, these catheter-based procedures introduce ablation elements into interior regions of the body by steering them through a vein or artery.

The Specification that follows focuses upon a particular field of use, which is the treatment of cardiac disease. Still, the diverse applicability of the invention in other fields of use will also become apparent.

Figure 1:
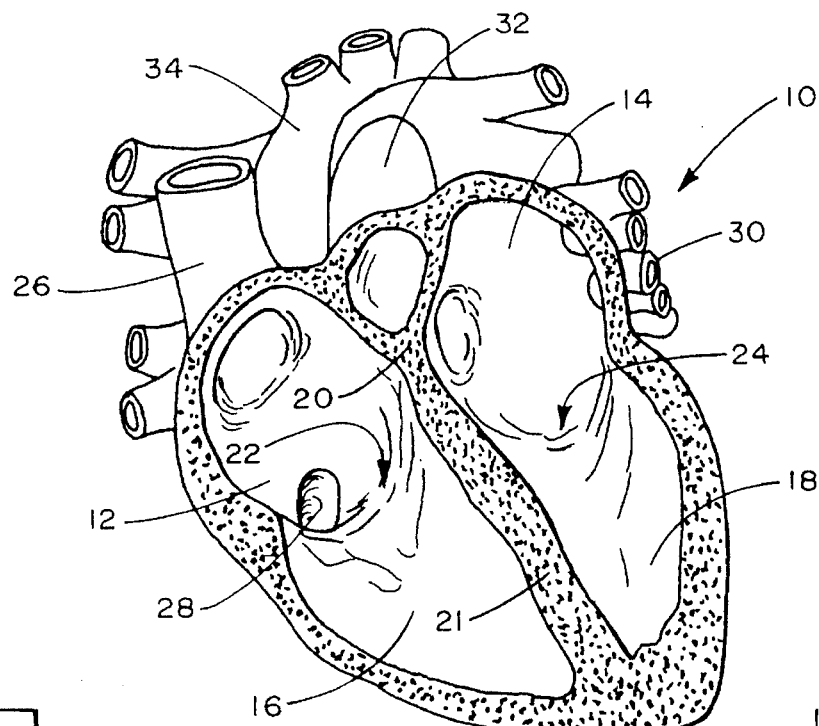
FIG. 1 is a simplified and somewhat diagrammatic perspective view of the human heart.

FIG. 1 shows a simplified and somewhat diagrammatic perspective view of the human heart 10.

The views of the heart 10 shown in FIG. 1 and other Figures in this Specification are not intended to be anatomically accurate in every detail. The Figures show views of the heart 10 in diagrammatic form as necessary to show the features of the invention.

As will be described in greater detail later, one application of the invention provides systems and methodologies for forming long, curvilinear ablation patterns inside the heart 10.

The Figures focus upon the details of using the invention to form long, curvilinear lesions for the treatment of atrial fibrillation. It should be appreciated, however, that the invention has applicability for use in other regions of the heart to treat other cardiac conditions. The invention also has application in other regions of the body to treat other maladies.

FIG. 1 shows the significant heart chambers and the blood vessels that service them. FIG. 1 shows the right and left right atria, respectively 12 and 14. FIG. 1 also shows the right and left ventricles, respectively 16 and 18.

FIG. 1 further shows the atrial septum 20 that separates the right and left atria 12/14. FIG. 1 also shows the ventricular septum 21 that separates the right and left ventricles 16/18.

As FIG. 1 further shows, the tricuspid valve 22 joins the right atrium 12 with the right ventricle 16. The mitral (bicuspid) valve 24 joins the left atrium 14 with the left ventricle 18.

The superior vena cava 26 (the "SVC") and the inferior vena cava 28 (the "IVC") open into the right atrium 12. The pulmonary veins 30 (the "PV's") open into the left atrium 14. The pulmonary artery 32 leads from the right ventricle 16. The aorta 34 leads from the left ventricle 18.

During normal sinus rhythm, blood enters the right atrium 12 through the SVC 26 and the IVC 28, while entering the left atrium 14 through the PV's 30. The atria 12/14 contract, and the blood enters the ventricles 16/18 (through the tricuspid and mitral valves 22 and 24, respectively). The ventricles 16/18 then contract, pumping the blood through the aorta and pulmonary arteries 32 and 34.

Figure 2:
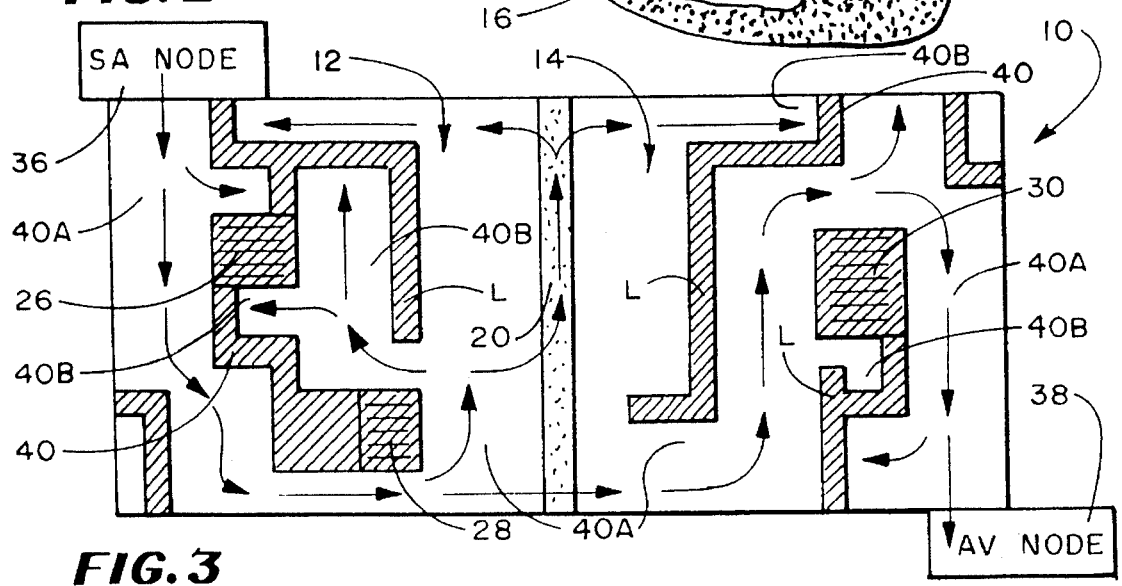
FIG. 2 is a diagrammatic plan view of the atrial region of the heart, showing a circuitous path for an electrical impulse to follow between the SA node and the AV node.

FIG. 2 shows a diagrammatic plan view of the atrial region of the heart 10. FIG. 2 shows the right atrium 12, the left atrium 14, and the atrial septum 20 dividing the right atrium 12 from the left atrium 14. FIG. 2 also shows the approximate location of the orifices of the SVC 26 and the IVC 28 entering the right atrium 12. FIG. 2 further shows the approximate location of the orifices of the PV's 30 entering the left atrium 14.

FIG. 2 also shows the atrial electrophysiology pertinent to the generation and treatment of atrial arrhythmias. FIG. 2 shows the SA node 36 located near the SVC 26. It also shows the AV node 38.

By folding the left-hand edge of the plan view of FIG. 2 against the center septum 20, one forms the three-dimensional contour of the right atrium 12. By folding the right-hand edge of the plan view of FIG. 2 against the center septum 20, one forms the three-dimensional contour of the left atrium 14.

FIG. 2 further shows a maze pattern 40 overlaid upon the plan view of the right and left atria 12 and 14. The particular maze pattern 40 shown is adopted from one developed by Dr. Cox. See Cox et al., "The Surgical Treatment of Atrial Fibrillation," *The Journal of Cardiovascular Surgery*, Vol. 101, No. 4, pp. 569–592 (1991).

The maze pattern 40 directs the sinus impulse from the SA node 36 to the AV node 38 along a specified route. The route that the pattern 40 establishes includes a main conduction route 40A that leads circuitously from the SA node to the AV node. The route also includes multiple blind alleys 40B off the main conduction route 40A.

The pattern 40 is laid out to assure that the sinus impulse activates most of the atrial myocardium. Also, the pattern 40 blocks portions of the most common reentry circuits around the SVC 26, IVC 28, and the PV's 30. The lesion pattern 40 interrupts each of these common reentry circuits to thereby interrupt the generation of reentry circuits in these atrial regions.

The invention provides systems and methods for establishing the maze pattern 40, or one like it, without open heart surgery and without conventional surgical incisions.

The systems and methods that embody the invention ablate myocardial tissue in the atria. In the process, they form elongated (i.e., long and thin) and sometimes curvilinear lesions (designated "L" in FIG. 2). The lesions L destroy the myocardial tissue in those regions where reentry circuits usually occur. Electrical conduction is interrupted in the regions the lesions L occupy.

The presence of the lesions L force electrical impulses emanating in the SA node 36 to follow the open (i.e., not ablated) myocardial regions, which extend between the lesions L. The open regions form a circuitous path leading from the SA node 36 to the AV node 38, while eliminating reentry pathways.

In this way, the lesions L prevent atrial fibrillation from occurring.

The lesions L thus serve the same purpose as the incisions made during a surgical maze procedure. However, they do not require an invasive and costly surgical technique. Instead, according to the invention, the physician forms the lesions L without opening the heart. Instead, the physician maneuvers one or more ablation elements through a vein or artery into the atria.

For this purpose, the systems and methods that embody the invention provide a family of ablating elements. Numeral 42 generally designates each individual element in FIGS. 5 to 10 and 25 to 41. In use, the elements 42 form various curvilinear lesion patterns.

In the preferred embodiments, the elements 42 create the lesions L by thermally destroying myocardial tissue by the application of electromagnetic energy. In the particular illustrated embodiments, the elements 42 emit radiofrequency electromagnetic energy. Alternatively, microwave electromagnetic energy or light (laser) energy could be employed for the same purpose.

The direct emission of heat energy by an elongated element by resistance heating does not form uniformly long, thin lesion patterns as defined by the invention. Direct heating of an elongated element results in lesion patterns having regions of charring that offer no therapeutic benefit.

Still, it is believed the invention can be adapted to other ablation techniques that do not involve the direct contact between a resistance heated element and tissue. For example, it is believed that long, thin, and curvilinear lesions can be formed by destroying myocardial tissue by cooling or by injecting a chemical substance that destroys myocardial tissue.

The preferred embodiments of the invention provide two general categories or types of curvilinear ablating elements 42 that emit radiofrequency energy.

FIGS. 5 to 14 show one preferred category of radiofrequency ablating elements 42. In this category, the ablating elements 42 make intimate contact against the atrial wall to create an array of adjoining curvilinear lesions L all at once. One of these types of elements 42, once deployed, can form all or substantially all of desired maze pattern. This category of ablating elements will sometimes be identified as "Category 1 Curvilinear Ablating Elements."

According to another aspect of the invention, the Category 1 Ablating Elements share a common delivery system 44. The delivery system 44 introduces and deploys a selected Category 1 Ablating Elements in the atria 12/14.

FIGS. 27 to 55 show another preferred category of radiofrequency ablating elements 42. In this category, the ablating elements 42 make intimate contact against the atrial wall to create discrete elongated, curvilinear lesions L, one at a time. The physician individually deploys these ablating elements 42 in succession to form the desired maze pattern. This category of ablating elements will sometimes be identified as "Category 2 Curvilinear Ablating Elements."

Unlike the Category 1 Ablating Elements, the Category 2 Ablating Elements do not require a delivery system 44 for introduction and deployment in the atria 12/14. The Category 2 Ablating Elements are steerable. They can be introduced into the atria 12/14 like a conventional steerable catheter.

The Delivery System

FIGS. 15 to 26 best show the details of common delivery system 44.

Figures 20, 21:
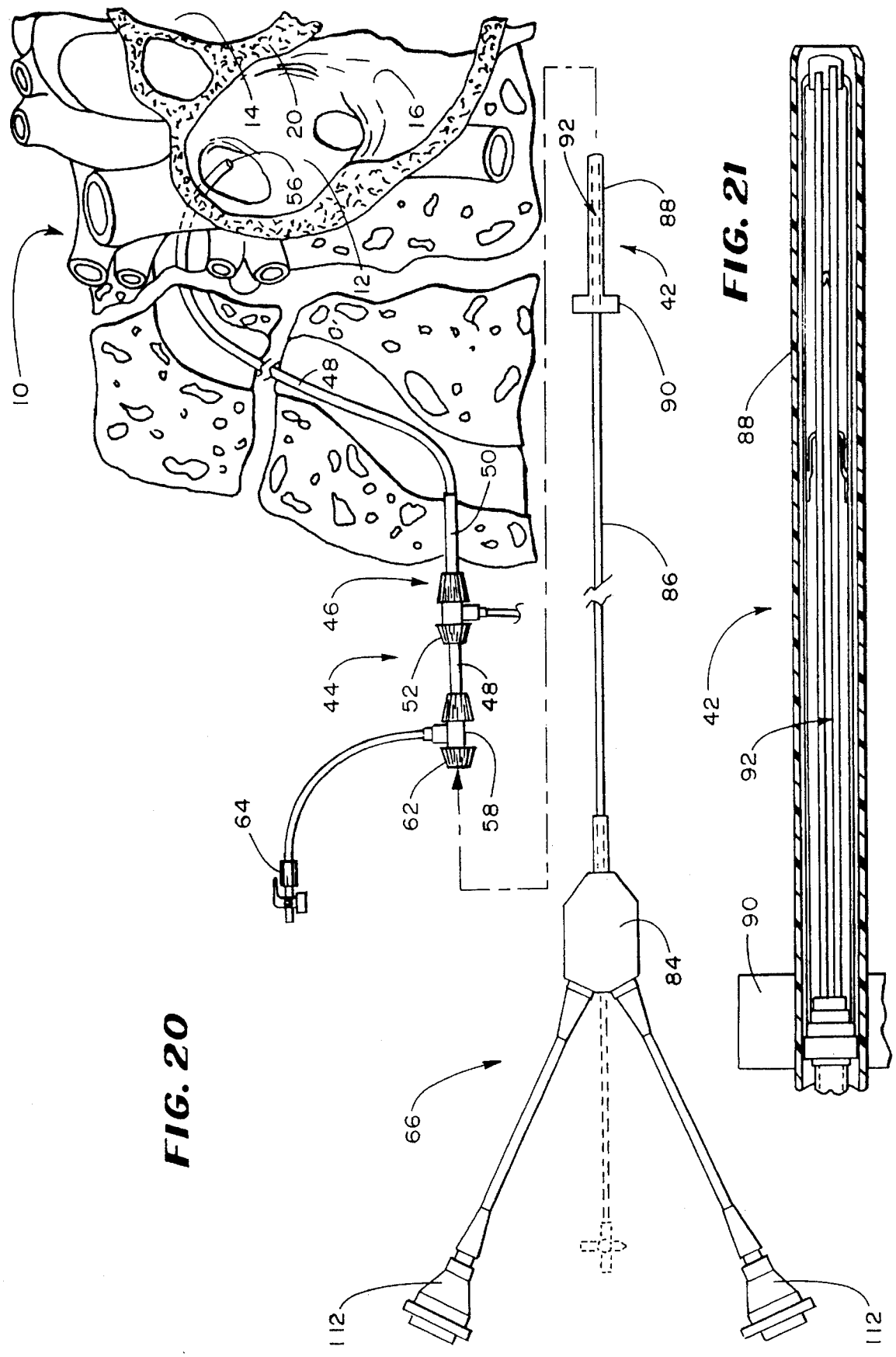

Using the delivery system 44, the physician first introduces a selected ablating element 42 into the right atrium 12 through the femoral vein (as FIG. 20 generally shows). The physician transmits radiofrequency ablating energy through the ablating element 42 to create the curvilinear lesion L or pattern of lesions L in the myocardium of the right atrium 12.

Figure 25A:
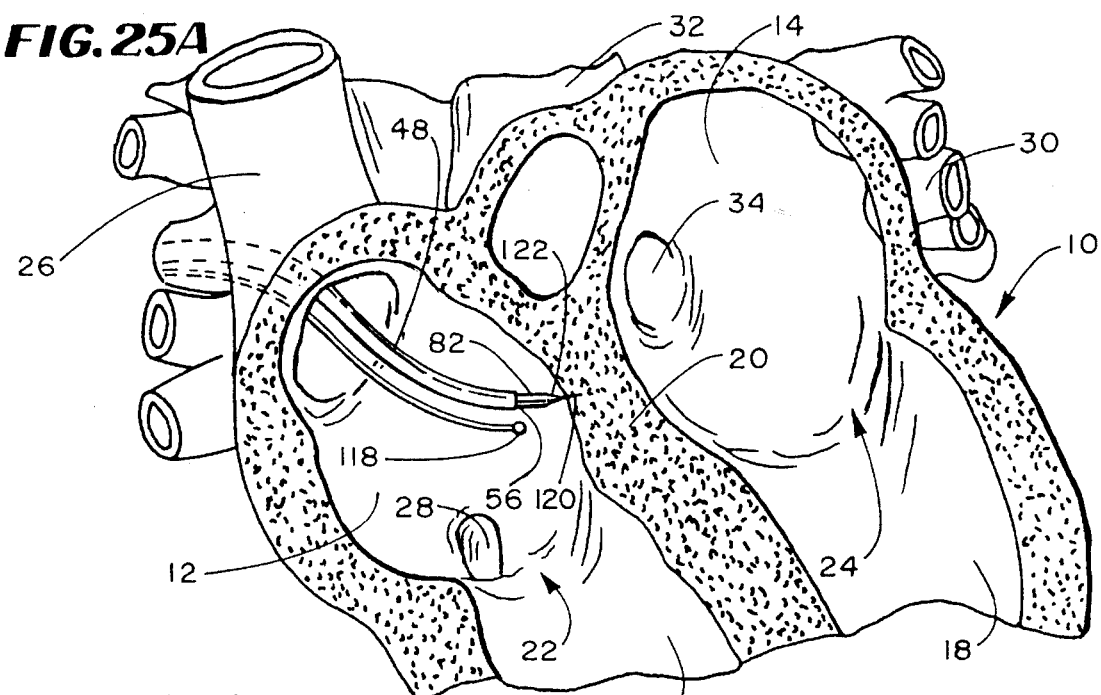
Figure 25B:
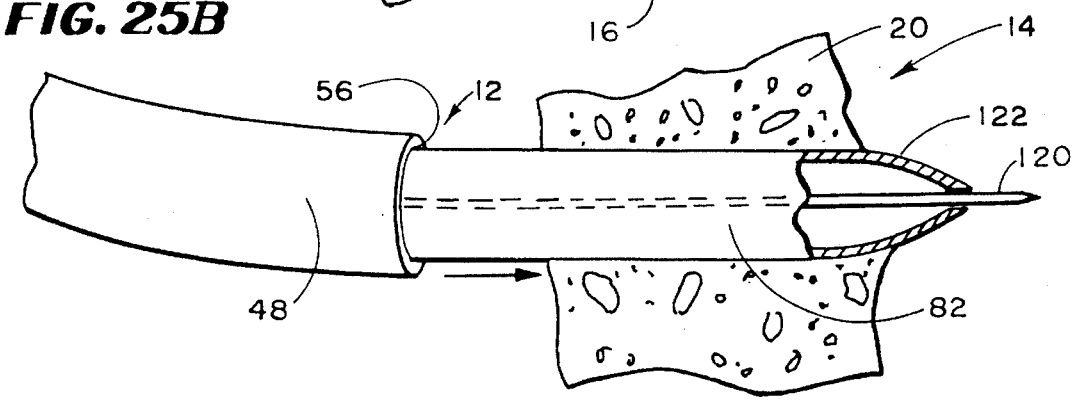
Figure 26:
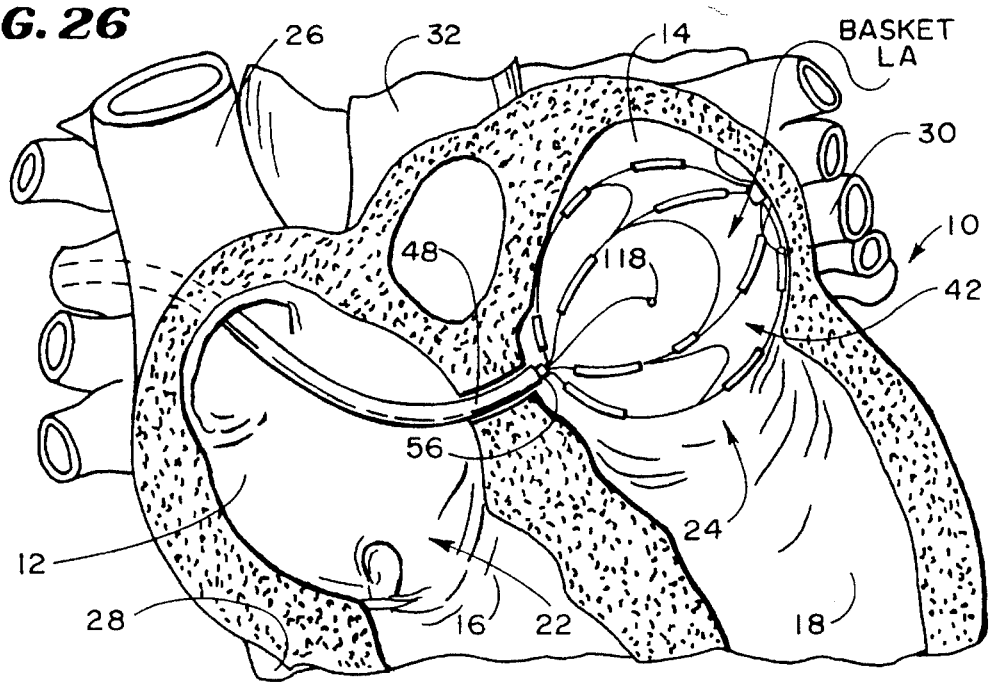

Once the desired lesion pattern is made in the right atrium, the physician enters the left atrium 14 through the atrial septum 20 (as FIGS. 25 and 26 generally show). The physician deploys another selected ablating element 42 into the left atrium 14 by puncturing through the atrial septum 20 (as FIG. 26 generally shows). The physician transmits radiofrequency ablating energy through the ablating element 42 to create the desired curvilinear lesion L or pattern of curvilinear lesions L in the myocardium of the left atrium 14.

To carry out the above sequence of steps, the delivery system 44 includes an introducer 46 and an outer guide sheath 48 (see FIGS. 15 and 16). Both the introducer 46 and the guide sheath 48 are made from inert plastic materials, like polyester.

As FIG. 15 shows, the introducer 46 has a skin-piercing cannula 50. The physician uses the cannula 50 to establish percutaneous access into the femoral vein.

The exposed end of the introducer 46 includes a conventional hemostatic valve 52 to block the outflow of blood and other fluids from the access. The valve 52 may take the form of a conventional slotted membrane or conventional shutter valve arrangement (not shown).

The hemostatic valve 52 allows the introduction of the outer guide sheath 48 through it, as FIG. 16 shows.

The introducer 46 also preferably includes a flushing port 54 for introducing anticoagulant or other fluid at the access site, if required.

In the illustrated and preferred embodiment, the delivery system 44 also includes a guide catheter 60 for directing the outer guide sheath 48 into the right and left atria 12 and 14.

In one embodiment (see FIG. 16), the guide catheter 60 takes the form of a conventional steerable catheter with active steering of its distal tip. Alternatively, the guide catheter 60 can take the form of a catheter with a precurved distal tip, without active steering, like a conventional "pig tail" catheter. The catheter with a precurved distal tip is most preferred, because of its simplicity and lower cost. However, for the purposes of this Specification, the details of a catheter with active steering of the distal tip will also be discussed.

As FIG. 16 shows, the steerable catheter 60 includes a catheter body 68 having a steerable tip 70 at its distal end. A handle 72 is attached to the proximal end of the catheter body 68. The handle 72 encloses a steering mechanism 74 for the distal tip 70.

The steering mechanism 74 can vary. In the illustrated embodiment (see FIG. 17), the steering mechanism is the one shown in Copending U.S. application Ser. No. 07/789, 260, which is incorporated by reference.

Figures 17, 18:
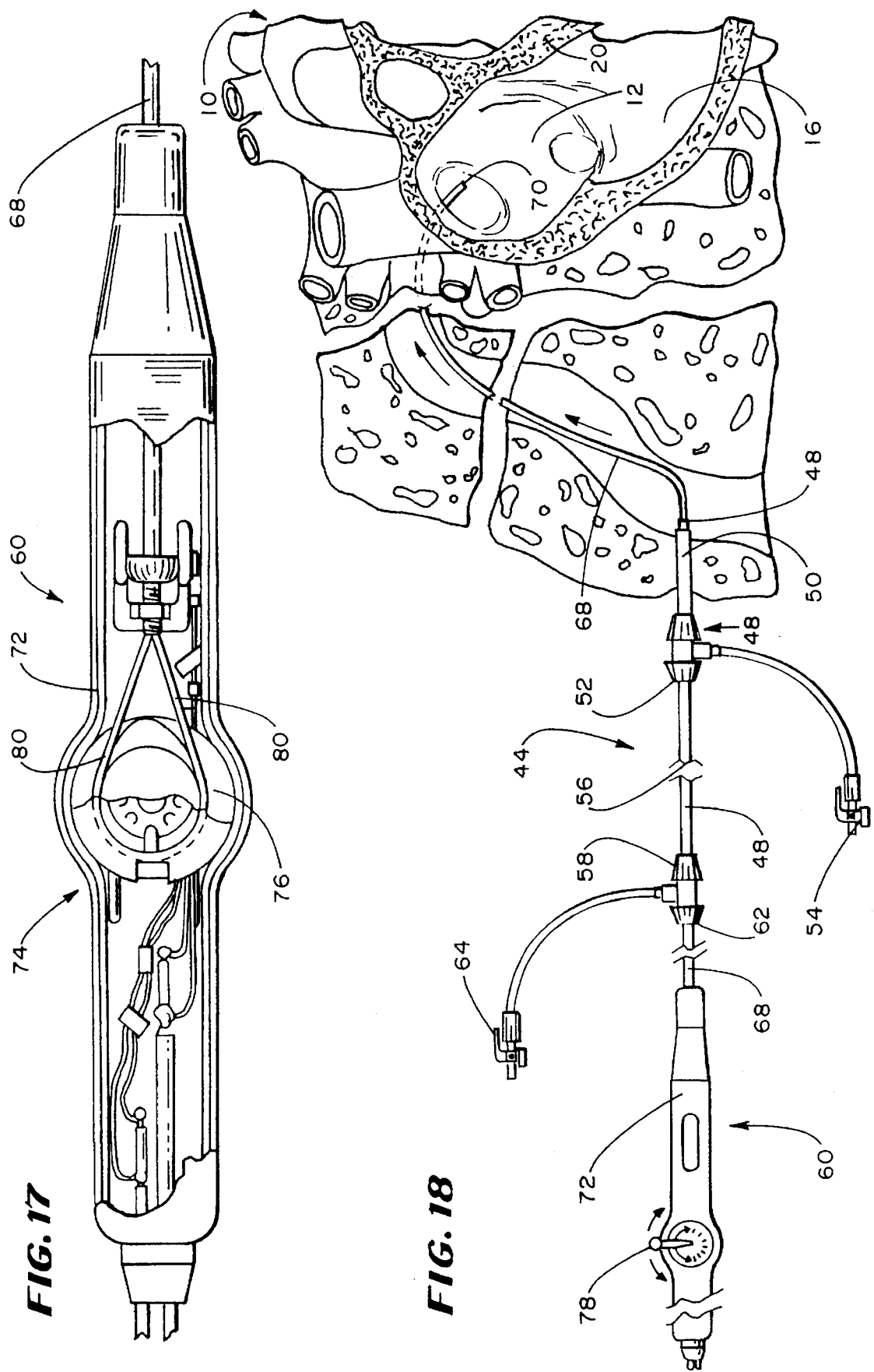

As FIG. 17 shows, the steering mechanism 74 of this construction includes a rotating cam wheel 76 within the handle 72. An external steering lever 78 rotates the cam wheel. The cam wheel 76 holds the proximal ends of right and left steering wires 80.

The steering wires 80 extend along the associated left and right side surfaces of the cam wheel 76 and through the catheter body 68. The steering wires 80 connect to the left and right sides of a resilient bendable wire or spring (not shown). The spring deflects the steerable distal tip 70 of the catheter body 68.

As FIG. 16 shows, forward movement of the steering lever 80 bends the distal tip 70 down. Rearward movement of the steering lever 80 bends the distal tip 70 up. By rotating the handle 70, the physician can rotate the distal tip 70. By manipulating the steering lever 80 simultaneously, the physician can maneuver the distal tip 70 virtually in any direction.

Figure 19:
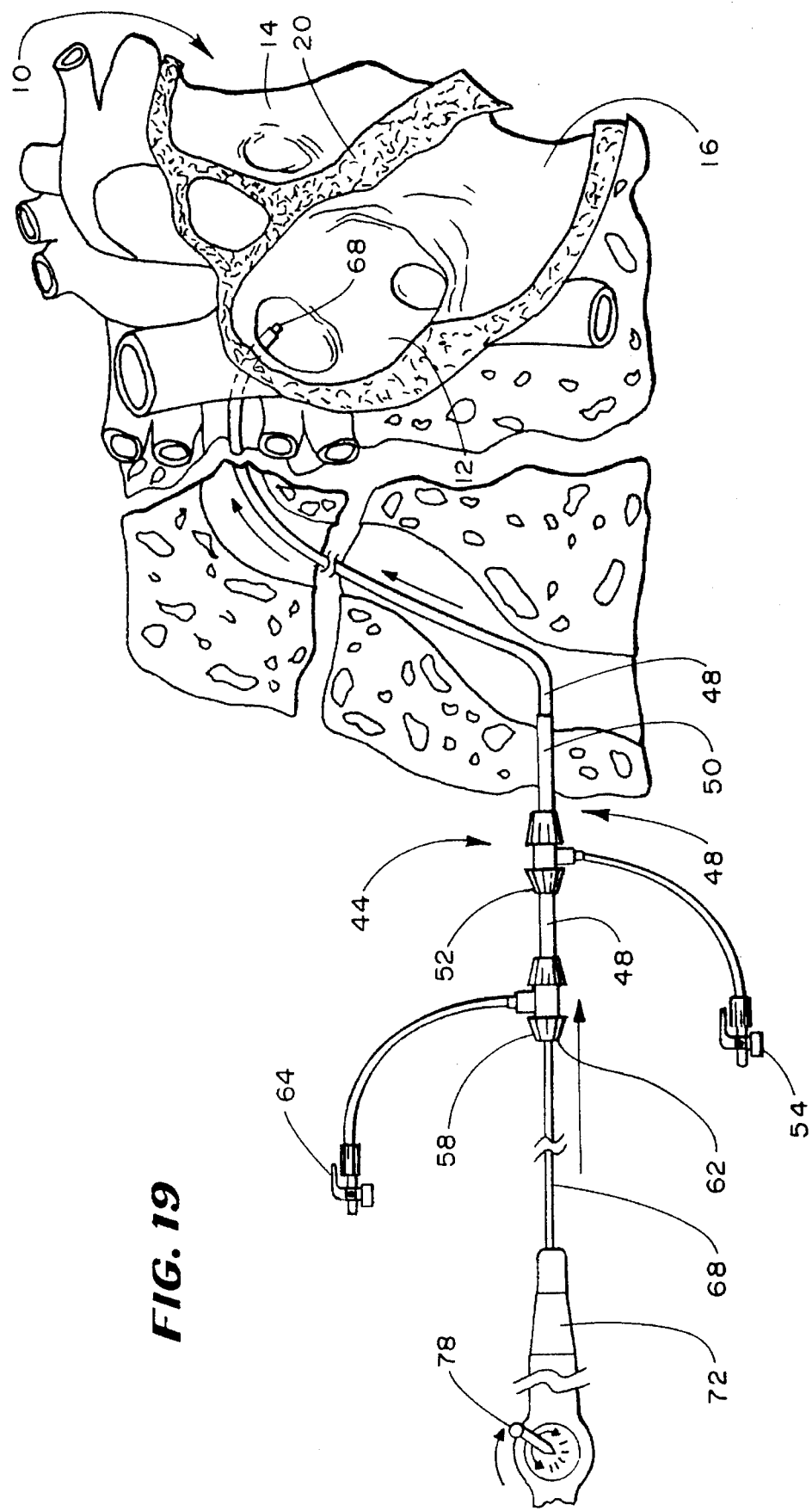

FIGS. 18 and 19 show the details of using the steerable catheter 60 to guide the outer sheath 48 into position.

The outer guide sheath 48 includes an interior bore 56 that receives the steerable catheter body 68. The physician can slide the outer guide sheath 48 along the steerable catheter body 68.

The handle 58 of the outer sheath 48 includes a conventional hemostatic valve 62 that blocks the outflow of blood and other fluids. The valve 62, like the valve 52, may take the form of either a resilient slotted membrane or a manually operated shutter valve arrangement (not shown).

Together, the valves 52 and 62 provide an effective hemostatic system. They allow performance of a procedure in a clean and relatively bloodless manner.

In use, the steerable catheter body 68 enters the bore 56 of the guide sheath 48 through the valve 62, as FIG. 18 shows. The handle 58 of the outer sheath 48 also preferably includes a flushing port 64 for the introduction of an anticoagulant or saline into the interior bore 56.

As FIG. 18 also shows, the physician advances the catheter body 68 and the outer guide sheath 48 together through the femoral vein. The physician retains the sheath handle 58 near the catheter handle 72 to keep the catheter tip 70 outside the distal end of the outer sheath 48.

In this way, the physician can operate the steering lever 78 to remotely point and steer the distal end 70 of the catheter body 68 while jointly advancing the catheter body 68 through the femoral vein.

The physician can observe the progress of the catheter body 68 using fluoroscopic or ultrasound imaging, or the like. The outer sheath 48 can include a radio-opaque compound, such as barium, for this purpose. Alternatively, a radio-opaque marker can be placed at the distal end of the outer sheath 16.

This allows the physician to maneuver the catheter body 68 through the femoral vein into the right atrium 12, as FIG. 18 shows.

As FIG. 19 shows, once the physician locates the distal end 70 of the catheter body 68 in the right atrium 12, the outer sheath handle 58 can be slid forward along the catheter body 68, away from the handle 72 and toward the introducer 46. The catheter body 68 directs the guide sheath 48 fully into the right atrium 12, coextensive with the distal tip 70.

Holding the handle 58 of the outer sheath 48, the physician withdraws the steerable catheter body 68 from the outer guide sheath 48.

The delivery system 44 is now deployed in the condition generally shown in FIG. 20. The system 44 creates a passageway that leads through the femoral vein directly into the right atrium 12. The delivery system 44 provides this access without an invasive open heart surgical procedure.

Alternatively, the outer guide sheath 48 can itself be preshaped with a memory. The memory assumes a prescribed curvature for access to the right or left atrium 12 or 14 through venous access, without need for a steerable catheter 60.

To assist passage through the atrial septum 20, the delivery system 44 includes a transeptal sheath assembly 82. The delivery system 44 guides the sheath assembly 82 into the right atrium 12 and through the atrial septum 20 (see FIGS. 25A and 25B) to open access to the left atrium 14.

The delivery system 44 further includes ablation probes 66 to carry a selected ablating element 42. FIG. 20 shows the common structural features shared by the ablation probes 66. Each ablating probe 66 has a handle 84, an attached flexible catheter body 86, and a movable hemostat sheath 88 with associated carriage 90. Each ablating probe 66 carries at its distal end a particular type of curvilinear ablating element 42.

Category 1

Curvilinear Ablating Elements

FIGS. 5 to 14 show structures representative of Category 1 Curvilinear Ablating Elements 42 that the probes 66 can carry. Elements 42 in this category take the form of various three-dimensional structures, or baskets 92.

The basket 92 can be variously constructed. In the illustrated and preferred embodiment, the basket 92 comprises a base member 98 and an end cap 100. An array of generally resilient, longitudinal splines 102 extend in a circumferentially spaced relationship between the base member 98 and the end cap 100. They form the structure of the basket 92. The splines 102 are connected between the base member 98 and the end cap 100 in a resilient, pretensed condition.

The basket 92 also include one or more transverse bridge splines 108 that periodically span adjacent longitudinal splines 102.

The splines 102/108 collapse into a closed, compact bundle in response to an external compression force. This occurs when they are captured within the movable hemostat sheath 88, as FIG. 21 shows. As will be described in greater detail later, the splines 102/108 are introduced through the delivery system 44 in this collapsed state.

Upon removal of the compression force, the splines 102/108 resiliently spring open to assume their three-dimensional shape. In this condition, the resilient splines 102/108 bend and conform to the tissue surface they contact. The atrial wall is also malleable and will also conform to the resilient splines 102/108. The splines 102/108 thereby make intimate contact against the surface of the atrial wall to be ablated, despite the particular contours and geometry that the wall presents.

Figure 5A:
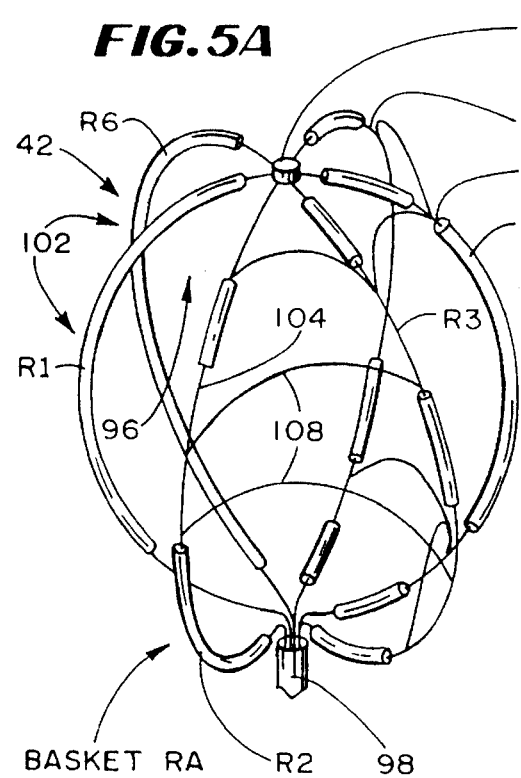
FIGS. 5A/5B are the three-dimensional structures formed when the splines shown in FIGS. 4A/4B are assembled, with the structure shown in FIG. 5A being intended for use within the right atrium and the structure shown in FIG. 5B being intended for use within the left atrium.

In the embodiment shown in FIGS. 5A/5B, six longitudinal splines 102 and six transverse bridge splines 108 form the basket 92. However, additional or fewer splines 102/108 could be used, depending upon continuity and complexity of the maze pattern wanted.

The splines 102/108 can be made of a resilient inert material, like Nitinol metal or silicone rubber. In the illustrated and preferred embodiment, each longitudinal spline 102 is rectangular in cross section and is about 1.0 to 1.5 mm wide. The bridge splines 108 are generally cylindrical lengths of material.

As FIGS. 5A/5B best show, the splines 102 include regions 104 that are electrically conductive (called the "conductive regions"). The splines 102 also include regions 106 that are electrically not conductive (called the "nonconductive regions").

In FIGS. 5A/5B, the bridge splines 108 comprise conductive regions 104 along their entire lengths.

The conductive regions 104 function as radiofrequency emitting electrodes held by the splines 102/108 in intimate contact against the atrial wall. These regions 104 emit radiofrequency ablating energy, when applied. The emitted energy forms the curvilinear lesions L in the myocardial tissue that generally conform to the propagation pattern of the emitted energy.

The lesions L formed by the conducting electrode regions 104 appear in juxtaposition with normal tissue that the nonconductive regions 106 contact. It is this juxtaposition of ablated tissue with normal tissue that forms the desired maze pattern.

The regions 104/106 can be variously created on the splines 102/108, depending upon the underlying material of the splines 102/108 themselves.

For example, when the splines 102/108 are made of an electrically conductive material, such as Nitinol, the electrically conductive regions 104 can consist of the exposed Nitinol material itself. In addition, the conductive regions 104 can be further coated with platinum or gold by ion beam deposition and the like to improve their conduction properties and biocompatibility. In this arrangement, insulating material is applied over regions of the Nitinol metal to form the nonconductive regions 106.

When the splines 102/108 are not made of an electrically conducting material, like silicone rubber, the conductive regions 104 are formed by coating the exterior surfaces with an electrically conducting material, like platinum or gold, again using ion beam deposition or equivalent techniques.

FIGS. 5A/5B and 4A/4B purposely exaggerate the diameter difference between the electrically conducting regions 104 and electrically nonconducting regions 106 to illustrate them. Actually, the diameter difference between the two regions 104/106 are approximately 0.05 mm to 0.1 mm, which is hard to detect with the naked eye, as FIGS. 7 to 14 show with greater realism.

The relative position of the conductive regions 104 and the nonconductive regions 106 on each spline 102, and the spaced apart relationship of the splines 102 and the bridge splines 108 take in the basket 92, depend upon the particular pattern of curvilinear lesions L that the physician seeks to form.

FIG. 5A shows a basket RA. Upon being deployed in the right atrium 12 and used to emit radiofrequency ablating energy, the basket RA creates the pattern of curvilinear lesions L shown in the left hand (i.e., right atrium) side of FIG. 2. The basket RA forms this pattern of lesions L essentially simultaneously when ablating energy is applied to it.

Figure 5B:
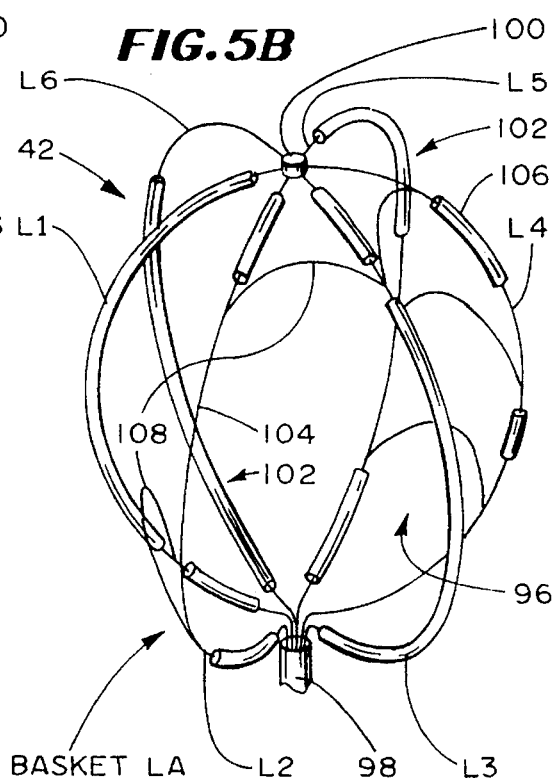

FIG. 5B shows a basket LA. Upon being deployed in the left atrium 14 and used to emit ablating energy, the basket LA creates the pattern of curvilinear lesions L shown in the right hand (i.e., left atrium) side of FIG. 2. Like basket RA, the basket LA forms this pattern of lesions L essentially simultaneously when ablating energy is applied to it.

Figure 3:
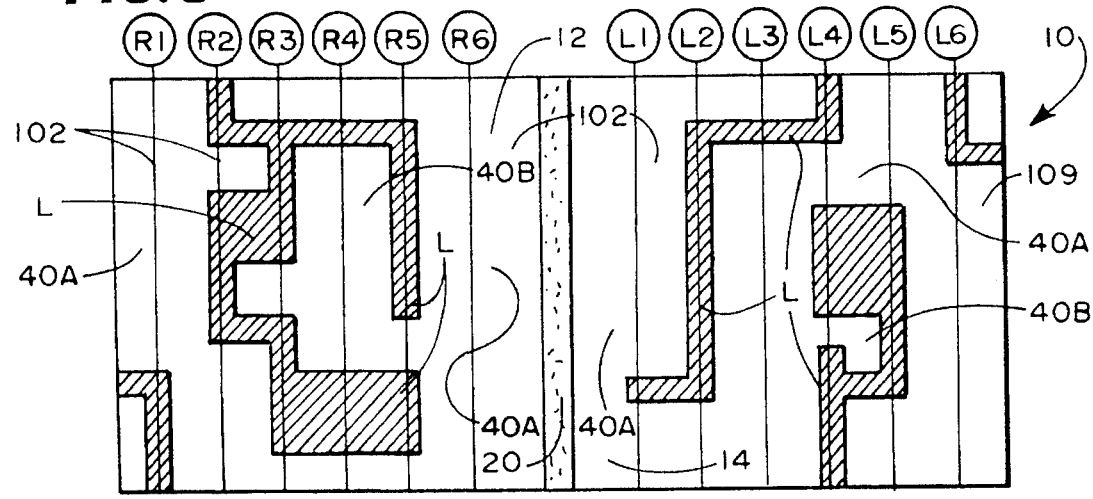
FIG. 3 is a grid for creating a three-dimensional structure for making curvilinear lesions within the atria of the heart.

FIGS. 3 and 4 generally show the methodology of assembling the splines 102/108 into the baskets RA and LA.

As FIG. 3 shows, the splines 102 are first laid out in an equally spaced arrangement upon a template 109. The template 109 displays the desired lesion pattern for the right and left atria 12 and 14.

FIG. 3 shows splines R1 to R6 laid out upon the template 109 where the lesion pattern for the right atrium 12 is displayed. FIG. 3 shows splines L1 to L6 laid out upon the template 109 where the lesion pattern for the left atrium is displayed.

The template 109 displays longitudinal lesion areas; that is, lesions L that run generally vertically on the template 109. The template 109 also displays transverse lesion areas; that is, lesions L that run generally horizontally on the template 109. The template 109 also displays areas that are to be free of lesions L.

Those portions of the splines R1–R6/L1–L6 that overlay a longitudinal lesion area must be electrically conducting to ablate tissue. These areas of the template 109 identify the electrically conducting regions 104 of the splines R1–R6/L1–L6.

Those portions of the splines R1–R6/L1–L6 that do not overlay a desired longitudinal lesion area must not be electrically conducting to create lesion-free areas. These areas of the template 109 identify the electrically nonconductive regions 106 of the splines R1–R6/L1–L6.

Figure 4A:
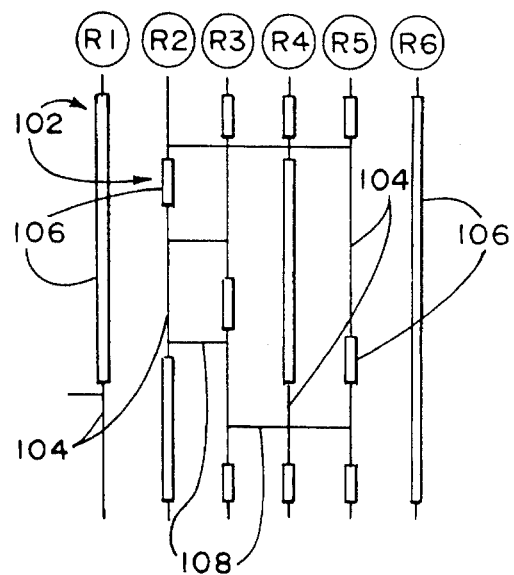
FIGS. 4A/4B are splines having electrically conductive and electrically non-conductive regions that, when assembled, emit ablating energy to form curvilinear lesions within the atria of the heart.
Figure 4B:
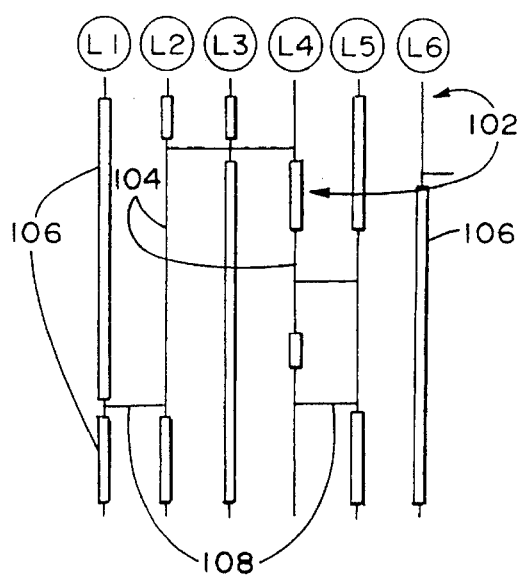

Electrically conducting or electrically insulating material are therefore applied, as appropriate, to the splines to form the regions 104/106 the template 109 identifies, as FIGS. 4A and 4B show. FIG. 4A shows these regions 104/106 formed on the splines R1–R6. FIG. 4B shows these regions 104/106 formed on the splines L1–L6.

In FIGS. 4A and 4B, the splines are made from an electrically conducting material (i.e., Nitinol), so an electrically insulating material is applied to form the nonconducting regions 106. The areas free of the electrically insulating material form the conducting regions 104.

The bridge splines 108 are positioned where the template 109 displays transverse lesion areas (shown in FIG. 3). The bridge splines 108 are soldered or otherwise fastened to the adjacent longitudinal splines 102. The bridge splines 108 are electrically conducting to ablate these transverse regions of tissue. The transverse lesions link the longitudinal lesions to create the circuitous bounds of the maze.

The invention therefore forms the template 109 that lays out the desired lesion pattern. The invention then uses the template 109 to identify and locate the conductive and nonconductive regions 104 and 106 on the longitudinal splines R1–R6/L1–L6. The template 109 is also used to identify and locate the bridge splines 108 between the longitudinal splines. The baskets RA and LA are then completed by attaching the base members 98 and end caps 100 to opposite ends of the longitudinal splines.

Figure 6:
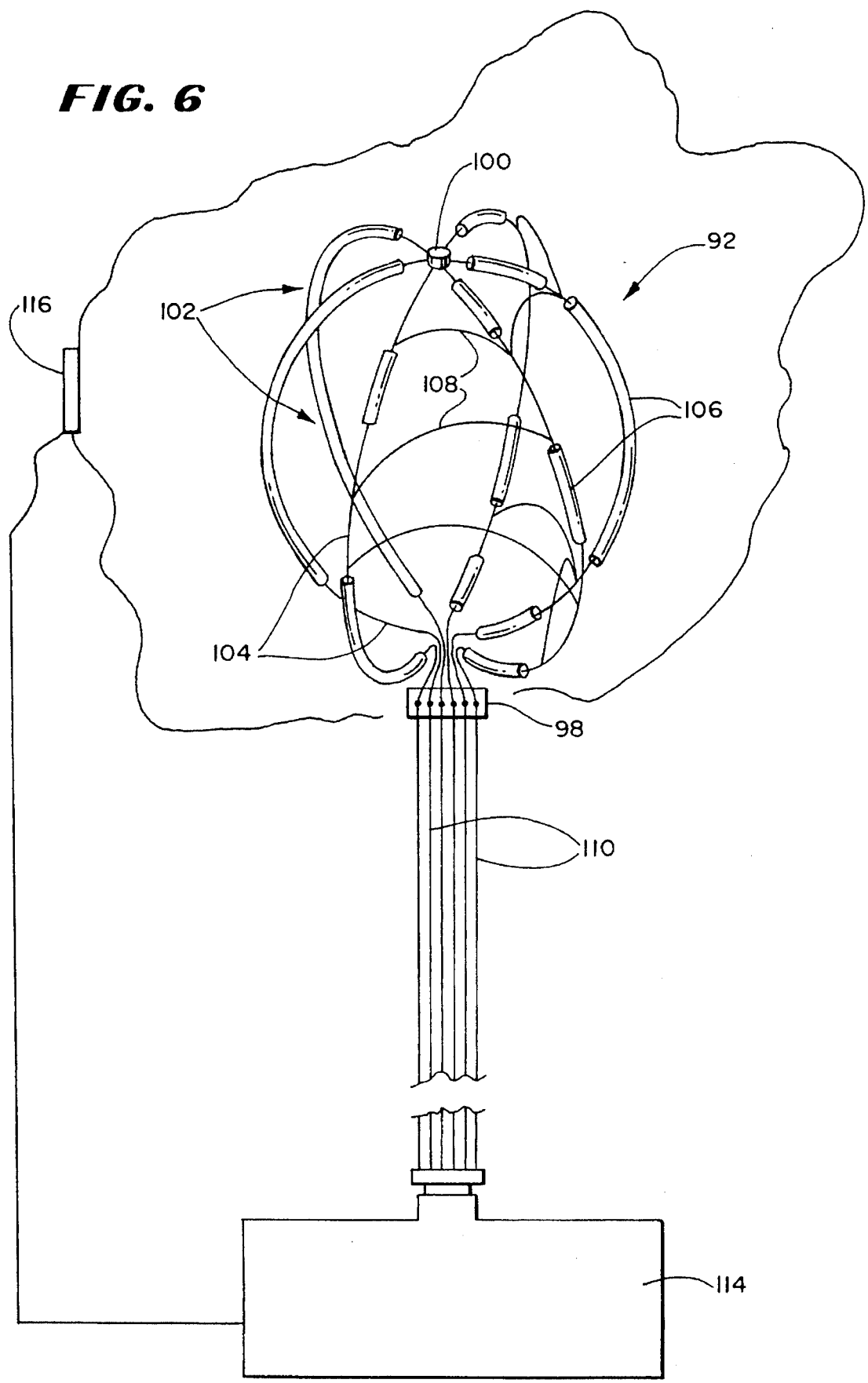
FIG. 6 is a perspective, largely diagrammatic view showing the electrical connections that transmit ablating energy to a three-dimensional structure for forming curvilinear lesions within the atria of the heart.

As FIG. 6 shows, each spline 102 is electrically coupled to a signal wire 110 made of an electrically conductive material, like copper alloy. The signal wires 110 extend through the base member 98 and catheter body 86 into the probe handle 84. Connectors 112 (shown in FIG. 20) attach the proximal ends of the signal wires 110 to an external source 114 of ablating energy.

The source 114 applies ablating energy to selectively activate all or some splines 102. The source 114 applies the ablating energy via the signal wires 110 to create iso-electric paths along the splines 102/108 conforming to the desired lesion pattern. Creation of iso-electric paths along the splines 102/108 reduces ohmic losses within the probe 66.

As FIG. 6 shows, the applied energy is transmitted by the conducting regions 104 of the splines 102/108. It flows to an exterior indifferent electrode 116 on the patient.

FIG. 20 shows the introduction of the catheter body 86 of the ablation probe 66 and its associated ablating element 42. The element 42 takes the form of basket RA shown in FIG. 5A. Before introducing the ablation probe 66, the physician advances the hemostat sheath 88 along the catheter body 86, by pushing on the carriage 90. The sheath 88 captures and collapses the basket RA with it, as FIG. 21 also shows.

As FIG. 22 shows, the physician introduces the hemostat sheath 88, with the enclosed, collapsed basket RA, through the hemostatic valve 62 of the outer sheath handle 58. The sheath 88 and enclosed basket RA enter the guide sheath 48. The hemostat sheath 88 protects the basket splines 102/108 from damage during insertion through the valve 62.

As FIG. 23 shows, when the catheter body 86 of the ablation probe 66 advances approximately three inches into the guide sheath 48, the physician pulls back on the sheath carriage 90. This withdraws the hemostat sheath 88 from the valve 62 along the catheter body 86. The hemostat valve 62 seals about the catheter body 86. The interior bore 56 of the guide sheath 48 itself now encloses and collapses the basket RA, just as the sheath 88 had done.

Figure 24:
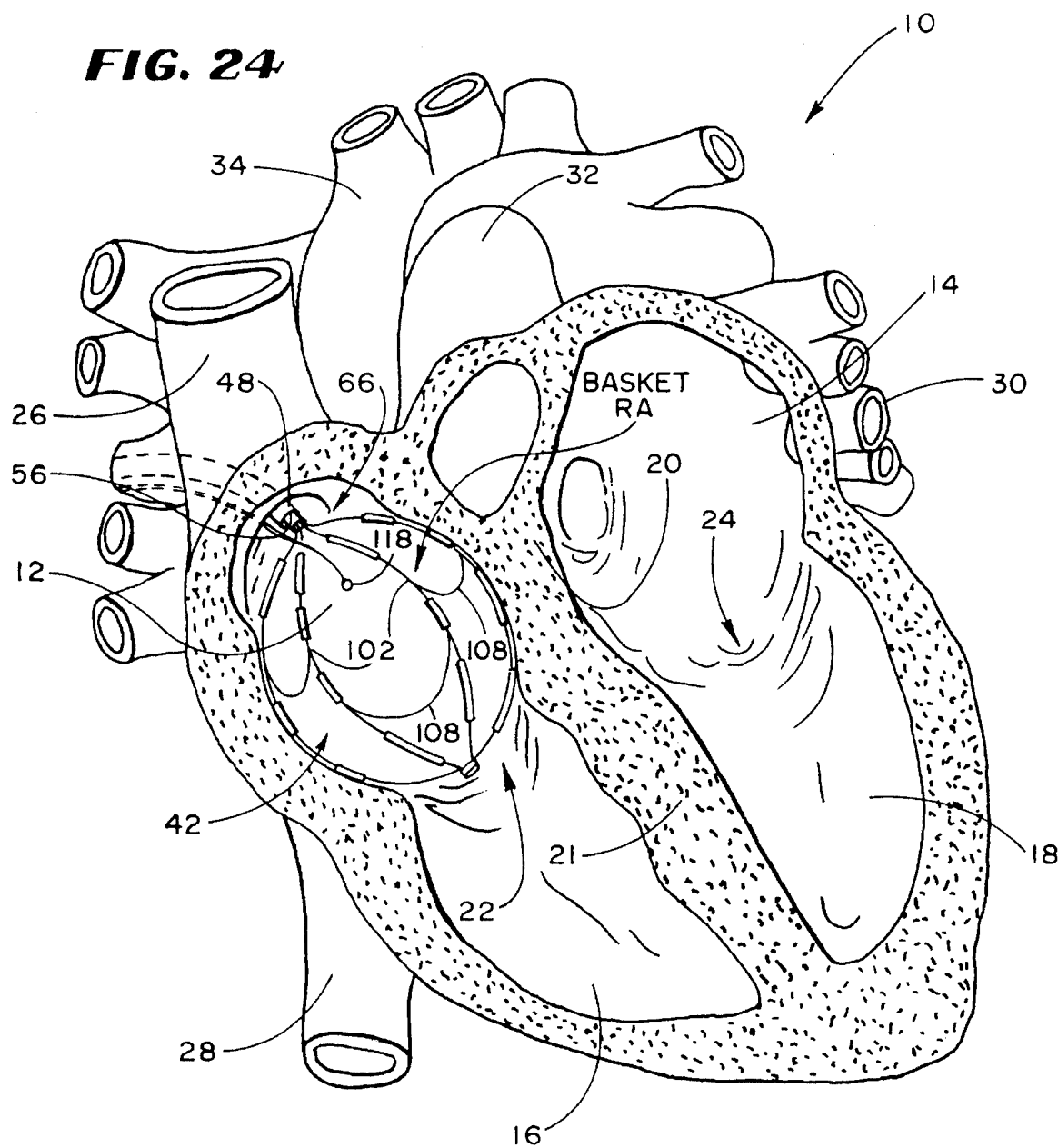

As FIGS. 23 and 24 show, the guide sheath 48 directs the catheter body 86 and attached basket RA of the ablation probe 66 into the right atrium 12. As the basket RA exits the distal end of the guide sheath 48, it will spring open within the right atrium 12, as FIG. 24 shows. The resilient splines 102/108 bend and conform to the myocardial surface of the right atrium 12.

In the illustrated and preferred embodiment (as FIG. 24 shows), the physician also deploys an ultrasonic viewing probe 118 through the femoral vein into the right atrium 12, either within our outside the guide sheath 48. Alternatively, fluoroscopy could be used. The physician operates the viewing probe 118 to observe the basket RA while maneuvering the basket RA to orient it within the right atrium 12. Aided by the probe 118, the physician can withdraw the basket RA back into the guide sheath 48. The physician can rotate the handle 84 to rotate the basket RA, and then redeploy the basket RA within the right atrium 12, until the physician achieves the desired orientation for the basket RA.

The physician now takes steps to ablate the myocardial tissue areas contacted by the conducting regions 104 of the basket RA. In this way, the physician forms the desired pattern of lesions L in the right atrium 12.

Upon establishing the desired lesion pattern, the physician withdraws the ablation probe 66 from the guide sheath 48, by that removing the basket RA from the right atrium 12. Aided by the viewing probe 118 (as FIG. 25A shows), the physician advances the guide sheath 48 further into the right atrium 12 into nearness with a selected region of the atrial septum 20.

To simplify placement of the guide sheath 48 next to the atrial septum 20, the physician preferable deploys the steerable catheter body 68 through the guide sheath 48 in the manner generally shown in FIGS. 18 and 19. Keeping the steerable tip 70 outside the distal end of the outer sheath 48, the physician operates the steering lever 78 to remotely point and steer the catheter body 68 across the right atrium toward the atrial septum 20, aided by the internal viewing probe 118, or by some external ultrasound or fluoroscopic imaging, or both.

Once the physician locates the distal end 70 of the catheter body 68 next to the desired site on the atrial septum 20, the physician slides the outer sheath 48 forward along the catheter body 68. The catheter body 68 directs the guide sheath 48 fully across the right atrium 12, coextensive with the distal tip 70 next to the atrial septum 20.

The physician withdraws the steerable catheter body 68 from the outer guide sheath 48 and (as FIG. 25A and 25B show) advances the transeptal sheath assembly 82 through the now-positioned guide sheath 48 into the atrial septum 20. The viewing probe 118 can be used to monitor the position of the guide sheath 48 and the advancement of the transeptal sheath assembly 82 toward the atrial septum 20.

As FIG. 25B shows, the transeptal sheath assembly 82 includes a cutting edge or dilator 122 that carries a sharpened lead wire 120. As the physician advances the transeptal sheath assembly 82, the lead wire 120 forms an initial opening in the septum 20. The dilator 122 enters this opening, enlarging it and punching through to the left atrium 14 (as FIG. 25B shows).

The Figures exaggerate the thickness of the atrial septum 20. The atrial septum 20 comprises a translucent membrane significantly thinner than the Figures show. This transeptal approach is a well known and widely accepted technique used in other left atrium access procedures.

The physician then slides the guide sheath 48 along the transeptal sheath assembly 82 and into the left atrium 14. The physician withdraws the transeptal sheath assembly 82 from the guide sheath 48. The guide sheath 48 now forms a path through the femoral vein and right atrium 12 into the left atrium 14 (as FIG. 26 shows)

The physician now introduces through the guide sheath 48 the catheter body 86 of another ablation probe 66 and its associated ablating element 42. At this step in the procedure, the ablating element 42 takes the form of basket LA shown in FIG. 5B. The physician advances the hemostat sheath 88 along the catheter body 86, as before described, to capture and collapse the basket LA. The physician introduces the hemostat sheath 88, with the enclosed, collapsed basket LA, through the hemostatic valve 62 of the outer sheath handle 58, and then withdraws the hemostat sheath 88.

Just as FIGS. 23 and 24 show the introduction of the basket RA into the right atrium 12, FIG. 26 shows the guide sheath 48 directing the basket LA into the left atrium 14. As the basket LA exits the distal end of the guide sheath 48, it will spring open within the left atrium 14, as FIG. 26 shows.

As FIG. 26 also shows, the physician also deploys the viewing probe 118 through the opening made in the atrial septum 20 into the left atrium 14. The physician operates the viewing probe 118 while maneuvering the basket LA to orient it within the left atrium 14. Aided by the probe 118, the physician can withdraw the basket LA back into the guide sheath 48, rotate the handle 84 to rotate the basket LA, and then redeploy the basket LA within the left atrium 14. The physician repeats these steps, until the desired orientation for the basket LA is achieved.

The physician now takes steps to ablate the myocardial tissue areas contacted by the conducting regions 104 of the basket LA. In this way, the physician forms the desired pattern of lesions L in the left atrium 14.

Upon establishing the desired lesion pattern, the physician withdraws the ablation probe 66 from the guide sheath 48, removing the basket LA from the left atrium 14. The physician then withdraws the guide sheath 48 from the heart and femoral vein. Last, the physician removes the introducer 46 to complete the procedure.

FIGS. 7 to 14 show alternative embodiments of ablating elements 42(1) to 42(7) that the ablation probe 66 can carry. The delivery system 44 as just described can be used to introduce and deploy each alternative ablating element 42(1) to 42(7) in the same way as baskets RA and LA.

The alternative ablating elements 42(1) to 42(5) shown in FIGS. 7 to 12 share many features that are common to that baskets RA and LA shown in FIGS. 5A and 5B. Consequently, common reference numerals are assigned.

The alternative elements 42(1)/(2)/(3)/(4)/(5) all take the form of a three-dimensional basket, designated 92(1), 92(2), 92(3), 92(4), and 92(5) respectively.

As before described, each basket 92(1)/(2)/(3)/(4)/(5) comprises a base member 98 and an end cap 100. As also earlier described, an array of generally resilient, longitudinal splines 102 extend in a circumferentially spaced relationship between the base member 98 and the end cap 100. They form the structure of the baskets 92(1)/(2)/(3)/(4)/(5).

As before described, the splines 102 are made of a resilient inert material, like Nitinol metal or silicone rubber. They are connected between the base member 98 and the end cap 100 in a resilient, pretensed condition.

Like the baskets RA and LA, the splines 102 of each basket 92(1)/(2)/(3)/(4)/(5) collapse for delivery into the atria 12/14 in a closed, compact bundle (as FIG. 21 generally shows). The splines 102 of each basket 92(1)/(2)/(3)/(4)/(5) also resiliently spring open to assume their three-dimensional shape when deployed in the atria 12/14, bending and conforming to the surrounding myocardial tissue surface.

As in the baskets RA and LA (shown in FIGS. 5A/5B), the splines 102 of each basket 92(1)/(2)/(3)/(4)/(5) include electrically conductive regions 104 juxtaposed with electrically nonconductive regions 106. These regions 104 and 106 are located and formed on the splines 102 of the baskets 92(1)/(2)/(3)/(4)/(5) using the same template 109 (shown in FIG. 3) and using the same surface alteration techniques (shown in FIGS. 4A/4B). As previously explained, the diameter differences between the two regions 104/106 are hard to detect with the naked eye, as FIGS. 7 to 10 show.

As before described, the conductive regions 104 function as radiofrequency emitting electrodes that form the curvilinear lesions L in the tissue that the conductive regions 104 contact. These lesion areas are juxtaposed with normal tissue that the nonconductive regions 106 contact.

Instead of the bridge splines 108 that the basket RA and LA carry, the baskets 92(1)/(2)/(3)/(4)/(5) use alternative assemblies to form the transverse legion regions spanning adjacent transverse splines 102.

Figure 7:
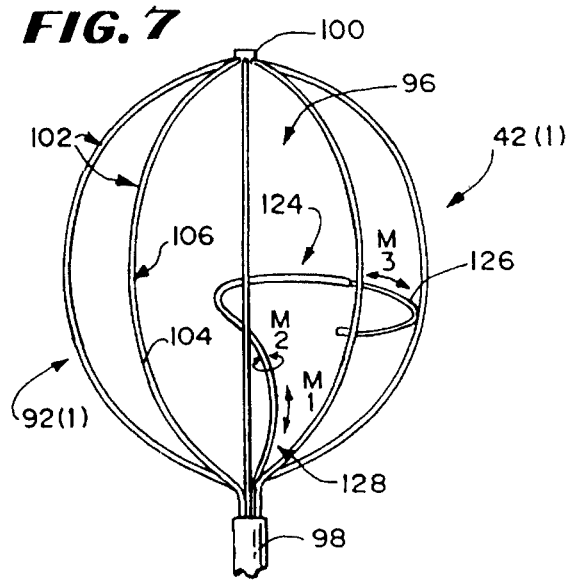
FIG. 7 is a perspective view of an alternate three-dimensional structure that can be used to emit ablating energy to form curvilinear lesions within the atria of the heart and that includes, as an integral part, a steerable distal element carried within the open interior area of the structure.
Figure 11:
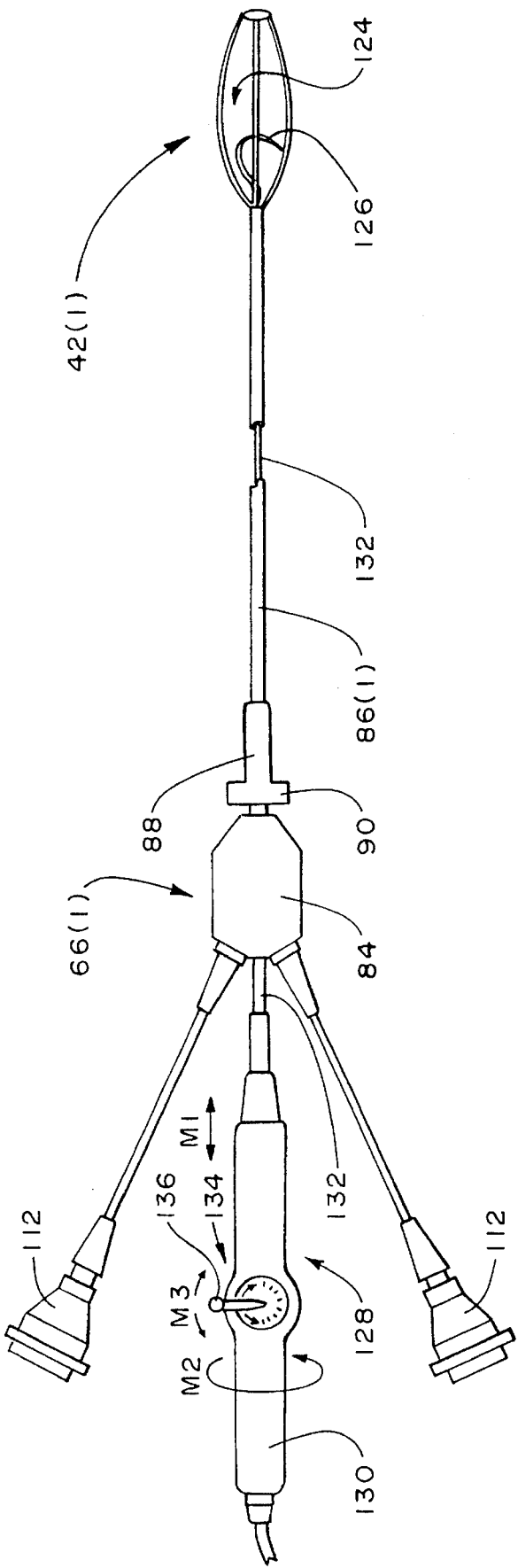
FIG. 11 is a plan view of an ablating probe that carries the three-dimensional basket structure shown in FIG. 7.

The ablating element 42(1) shown in FIGS. 7 and 11 includes, as an integral part, a steerable distal element 124 carried within the open interior area 96 of the basket 92(1). As FIG. 11 shows, the distal element 124 is itself part of a conventional steerable catheter assembly 128 that forms an integral part of the associated ablating probe 66(1).

The distal element 124 carries an electrode 126 comprising a strip of electrically conducting material, like Nitinol wire. In use, the electrode 126 serves as a single movable bridge electrode. In successive motions controlled by the physician, the single bridge electrode 126 can be positioned and ablating energy applied to it, to thereby make all the transverse lesions that the particular maze pattern requires. The single steerable bridge electrode 126 of the basket 92(1) thereby serves the function of the several fixed bridge splines 108 of the baskets RA and LA.

The bridge electrode 126 can also be used to "touch up" or perfect incomplete lesions patterns formed by the longitudinal splines 102.

The proximal end of the steering assembly 128 of the probe 66(1) includes a handle 130 (as FIG. 11 shows). A guide tube 132 extends from the handle 130, through the body 86(1) of the probe 66(1), and into the interior area 96 of the basket 92(1). The steerable distal element 124 and bridge electrode 126 make up the distal end of the guide tube 132.

The handle 130 encloses a steering mechanism 134 for the steerable distal element 124 and associated bridge electrode 126. The steering mechanism 134 for the assembly 128 is the same as the steering mechanism 74 for the distal tip 70 of the catheter 60 (shown in FIG. 17) and will therefore not be described again.

By manipulating the steering assembly 128 (as shown by arrows M1, M2, and M3 in FIG. 11), the physician can remotely steer the element 124 and the associated bridge electrode 126 in three principal directions inside the basket 92(1) (as shown arrows M1, M2 and M3 in FIG. 7).

First, by remotely pulling and pushing the handle 130, the physician moves the element 124 and bridge electrode 126 along the axis of the basket 92(1), in the direction of arrows M1 in FIGS. 7 and 11.

Second, by remotely rotating the handle 130, the physician rotates the element 124 and associated bridge electrode 126 about the axis of the basket 92(1), in the direction of arrows M2 in FIGS. 7 and 11.

Third, by manipulating the steering mechanism 134 by rotating the steering lever 136 (see FIG. 11), the physician bends the distal element 124, and with it, the bridge electrode 126 in a direction normal to the axis of the basket 92(1), in the direction of arrows M3 in FIGS. 7 and 11.

By coordinating lateral (i.e., pushing and pulling) movement of the handle 130 with handle rotation and deflection of the distal element 124, it is possible to move the bridge electrode 126 into any desired position, either between any two adjacent longitudinal splines 102 or elsewhere within the reach of the basket 92(1). Preferably, the physician deploys the interior viewing probe 118 or relies upon an external fluoroscopic control technique to remotely guide the movement of the bridge electrode 126 for these purposes.

Figure 8:
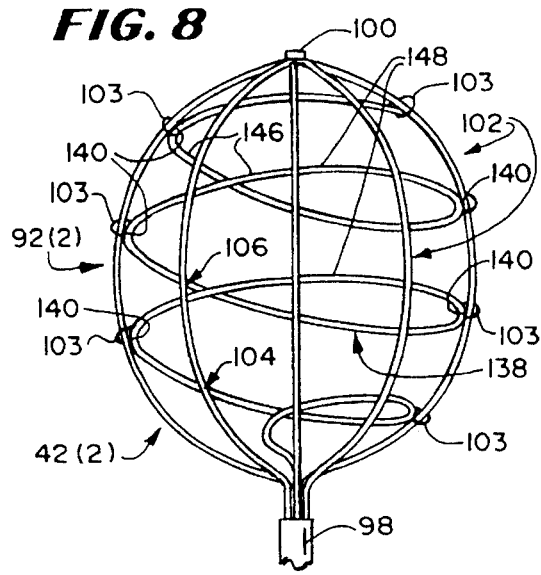
FIG. 8 is a perspective view of an alternate three-dimensional structure that can be used to emit ablating energy to form curvilinear lesions within the atria of the heart and that includes, as an integral part, an internal electrode structure that comprises a single length of wire material preshaped to assume a helical array.

The ablating element 42(2) shown in FIG. 8 includes, as an integral part, an internal electrode structure 138 that comprises a single length of wire material, such as Nitinol, preshaped to assume a helical array.

In FIG. 8, the helical electrode structure 138 extends from the base member 98 and spirals within the interior area 96 of the basket 92(2). Along its spiraling path within the basket 92(2), the helical electrode structure 138 creates interior points of contact 140 with the longitudinal splines 102. The structure 138 is slidably attached by eye loops 103 to the splines 102 at these interior points of contact 140.

The helical electrode structure 138 spanning the interior points of contact 140 includes regions 146 that are electrically conducting and regions 148 that are not electrically conducting. The precise location of the regions 146 and 148 along the spiraling path of the electrode structure 138 will depend upon the pattern of transverse lesions required.

Where a transverse lesion L is required, the structure 138 will include an electrically conducting region 146 between two points of contact 140 with adjacent splines 102. The points of contact 140 will also be conducting regions 104. In this way, the structure 138 serves to conduct ablating energy, when applied, between adjacent splines 102, just as the presence of the bridge splines 108 did in the baskets RA and LA.

Where a transverse lesion is not required, the structure 138 will include an electrically nonconducting region 148 between two points of contact 140 with adjacent splines 102. The points of contact 140 will also be nonconducting regions 106. In this way, the structure 138 will not conduct ablating energy between adjacent splines 102. The structure 138 in these regions 148 serve just as the absence of the bridge splines 108 did in the baskets RA and LA.

The electrically conducting regions 146 and electrically nonconducting regions 148 are formed along the helical structure 138 in the same way the comparable conducting and nonconducting regions 104 and 106 of the longitudinal splines 102 are formed.

The helical structure 138 captured within the basket 92(2) serves the same function as the bridge splines 108 of the baskets RA and LA in creating zones of transverse lesions.

The shape of the helical structure 138, its interior points of contact 140 with the longitudinal splines 102, and the location of the conducting and nonconducting regions 146 and 148 are, like the location of the regions 104/106 on the longitudinal splines 102, predetermined to create the desired pattern of longitudinal and transverse legions L when ablating energy is applied.

As with baskets RA and LA, these considerations for the basket 92(2) will require a particular arrangement of elements for use in the right atrium 12 and another particular arrangement of elements for use in the left atrium 14.

The helical electrode structure 138 will collapse laterally upon itself as the basket 92(2) itself collapses inward in response to an external compression force. The basket 92(2) can thereby be introduced into the atria 12/14 in the same manner as the baskets RA and LA. The structure 138 will assume its helical shape when the basket 92(2) springs open with the removal of the compression force. The basket 92(2) can thereby be deployed for use within the atria 12/14 in the same manner as the baskets RA and LA.

Figure 9:
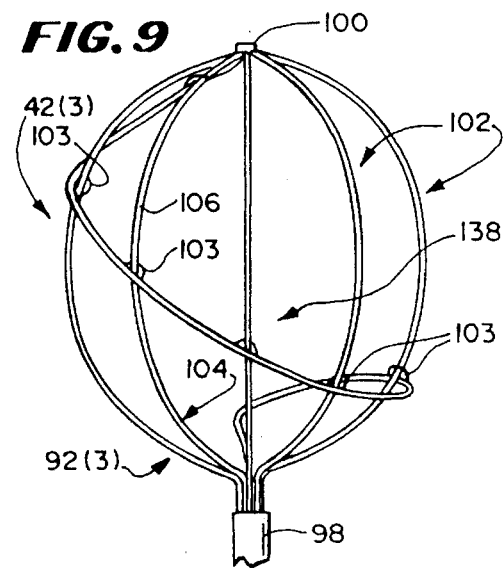
FIG. 9 is a perspective view of an alternate three-dimensional structure that can be used to emit ablating energy to form curvilinear lesions within the atria of the heart and that includes, as an integral part, an external electrode structure that comprises a single length of wire material preshaped to assume a helical array.

The ablating element 42(3) shown in FIG. 9 is similar in many respects to the ablating element 42(2) shown in FIG. 8. The ablating element 42(3) includes, as an integral part, an internal electrode structure 142. Like the structure 138 shown in FIG. 8, the structure 42(3) comprises a single length of wire material, such as Nitinol, preshaped to assume a helical array.

In FIG. 9, like the structure 138 in FIG. 8, the helical electrode structure 142 extends from the base member 98. However, unlike the structure 138 shown in FIG. 8, the structure 142 in FIG. 9 spirals outside along the exterior surface of the basket 92(3). Like the structure 138, the structure 142 is slidably attached by eye loops 103 to the splines 102 at the exterior points of contact 144.

In other respects, the helical structure 138 and the helical structure 142 are essentially identical. Similar to the structure 138, the helical structure 142 spanning the points of contact 144 includes regions 146 that are electrically conducting and regions 148 that are not electrically conducting, depending upon the pattern of transverse lesions required. Where a transverse lesion L is required, the structure 142 will include an electrically conducting region 146. Similarly, where a transverse lesion is not required, the structure 142 will include an electrically nonconducting region 148.

The electrically conducting regions 146 and electrically nonconducting regions 148 are formed along the helical structure 142 in the same way the comparable conducting and nonconducting regions 104 and 106 of the longitudinal splines 102 are formed.

The helical structure 138 carried outside the basket 92(3) serves the same function as the bridge splines 108 of the baskets RA and LA in creating zones of transverse lesions.

As with the structure 138, the shape of the helical structure 142, its exterior points of contact 144 with the longitudinal splines 102, and the location of the conducting and nonconducting regions 146 and 148 are predetermined to create the desired pattern of longitudinal and transverse legions L when ablating energy is applied.

As with baskets RA and LA, and the basket 42(2), these considerations for the basket 92(3) will require a particular arrangement of elements for use in the right atrium 12 and another particular arrangement of elements for use in the left atrium 14.

The helical electrode structure 142, like the structure 138, will collapse laterally upon itself and spring back and open into its predetermined shape as the basket 92(3) itself collapses and opens. The basket 92(3) can be introduced and deployed into the atria 12/14 in the same manner as the baskets RA and LA and the basket 92(2).

FIGS. 12A and B show an alternative helical electrode structure 150 within a basket 92(4). The basket 92(4) is essentially identical to the baskets 92(2) and 92(3) previously described. The helical structure 150, like the structures 138 and 142, includes electrically conducting regions 146 and electrically nonconducting regions 148 formed along its length.

However, unlike the structures 138 and 142 shown in FIGS. 8 and 9, the structure 150 is not integrally attached to the basket 92(4). Instead, the structure 150 can be remotely moved by the physician between a retracted position near the base member 98 of the associated basket 92(4) (as FIG. 12A shows) and a deployed position within the basket 92(4) (as FIG. 12B shows).

The structure 150 occupies its retracted position when the basket 92(4) is collapsed within the guide sheath 48 for introduction into the selected atria 12/14, as FIG. 12A shows. The structure 150 is deployed for use after the basket 92(4) is deployed outside the distal end of the guide sheath 48 for use within the selected atria 12/14, as FIG. 12B shows.

In this embodiment, the electrode structure 150 comprises a length of memory wire, like Nitinol, that is preshaped into the desired helical shape. The structure 150 is attached to the distal end of a push/pull rod 152 that extends through a bore 153 in the body 154 of an associated probe 156. The push/pull rod 152 is attached at its proximal end to a slide control lever 158 that extends from the handle 160 of the probe 156. Fore and aft movement of the slide control lever 158 causes axial movement of rod 152 within the bore 153.

Pulling back upon the slide control lever 158 (as FIG. 12A shows) moves the rod 152 aft (i.e., toward the handle 160). The aft movement of the rod 152 draws the structure 150 out of the basket 92(4) and into the distal end of the probe body 154. As the structure 150 enters the confines of the bore 153, it resiliently straightens out, as FIG. 12A shows.

Pushing forward upon the slide control lever 158 (as FIG. 12B shows) moves the rod 152 forward (i.e., away from the handle 160). The forward movement of the rod moves the structure 150 out of the confines of the bore 153 and into the interior area 96 of the basket 92(4). Since the structure 150 possesses a resilient memory, it will return to its preformed helical shape as it exits the bore 153 and enters the basket 92(4), as FIG. 12B shows. The resilient memory of the structure 150 generally aligns the conductive and nonconductive regions 146 and 148 of the structure 150 with the conducting and nonconducting regions 104 and 106 of the longitudinal splines 102 to form the desired pattern of longitudinal and transverse lesions L.

Figure 10:
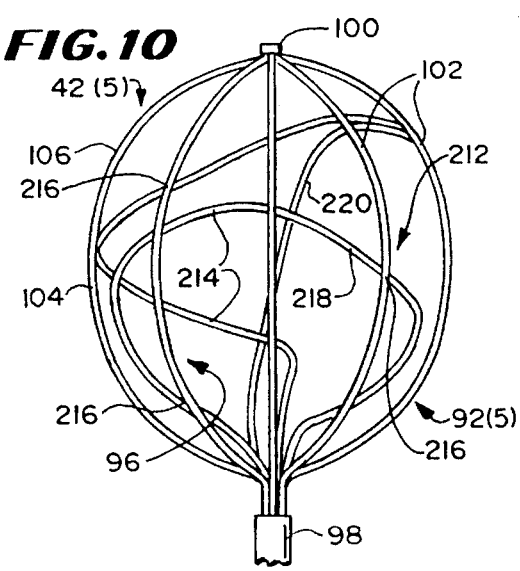
FIG. 10 is a perspective view of an alternate three-dimensional structure that can be used to emit ablating energy to form curvilinear lesions within the atria of the heart and that encloses, as an integral part, an internal basket structure.

The ablating element 42(5) shown in FIG. 10 includes an external basket 92(5) that encloses, as an integral part, an internal basket structure 212. The internal basket structure 212 includes several individual splines 214 of wire material, such as Nitinol, preshaped to assume a three-dimension array. The individual splines 214 extend from the base member 98 and transverse prescribed paths within the interior area 96 of the basket 92(5). The several paths the interior splines 214 create interior points of contact 216 with the longitudinal splines 102 of the exterior basket 92(5). The individual splines 214 are free to move with respect to the splines 102 at these interior points of contact 216.

The interior basket structure 212 spanning the interior points of contact 216 includes regions 218 that are electrically conducting and regions 220 that are not electrically conducting. The precise location of the regions 218 and 220 along the several paths of the interior splines 214 will depend upon the pattern of transverse lesions that is required.

Where a transverse lesion L is required, the interior basket structure 212 will include an electrically conducting region 218 between two points of contact 216 with adjacent exterior splines 102. The points of contact 216 will also be conducting regions 104. In this way, the interior basket structure 212 serves to conduct ablating energy, when applied, between adjacent splines 102, just as the presence of the bridge splines 108 did in the baskets RA and LA.

Where a transverse lesion is not required, the interior basket structure 212 will include an electrically nonconducting region 220 between two points of contact 216 with adjacent exterior splines 102. The points of contact will also be nonconducting regions 106. In this way, the interior basket structure 212 will not conduct ablating energy between adjacent exterior splines 102. The interior basket structure 212 in these regions 220 serve just as the absence of the bridge splines 108 did in the baskets RA and LA.

The electrically conducting regions 218 and electrically nonconducting regions 220 are formed along the interior splines 214 in the same way the comparable conducting and nonconducting regions 104 and 106 of the longitudinal exterior splines 102 are formed.

The interior basket structure 212 captured within the exterior basket 92(5) serves the same function as the bridge splines 108 of the baskets RA and LA in creating zones of transverse lesions.

The shape of the interior basket structure 212, its interior points of contact 216 with the longitudinal exterior splines 102, and the location of the conducting and nonconducting regions 218 and 220 are, like the location of the regions 104/106 on the longitudinal splines 102, predetermined to create the desired pattern of longitudinal and transverse legions L when ablating energy is applied.

As with baskets RA and LA, these considerations for the basket 92(5) and associated interior basket structure 212 will require a particular arrangement of elements for use in the right atrium 12 and another particular arrangement of elements for use in the left atrium 14.

The interior basket structure 212 will collapse upon itself as the exterior basket 92(5) itself collapses inward in response to an external compression force. The double basket 92(5)/212 can be introduced into the atria 12/14 in the same manner as the baskets RA and LA. The double basket 92(5)/212 will reassume its shape when the baskets 92(5)/212 spring open with the removal of the compression force. The double basket 92(5)/212 can be deployed for use within the atria 12/14 in the same manner as the baskets RA and LA.

Figure 13:
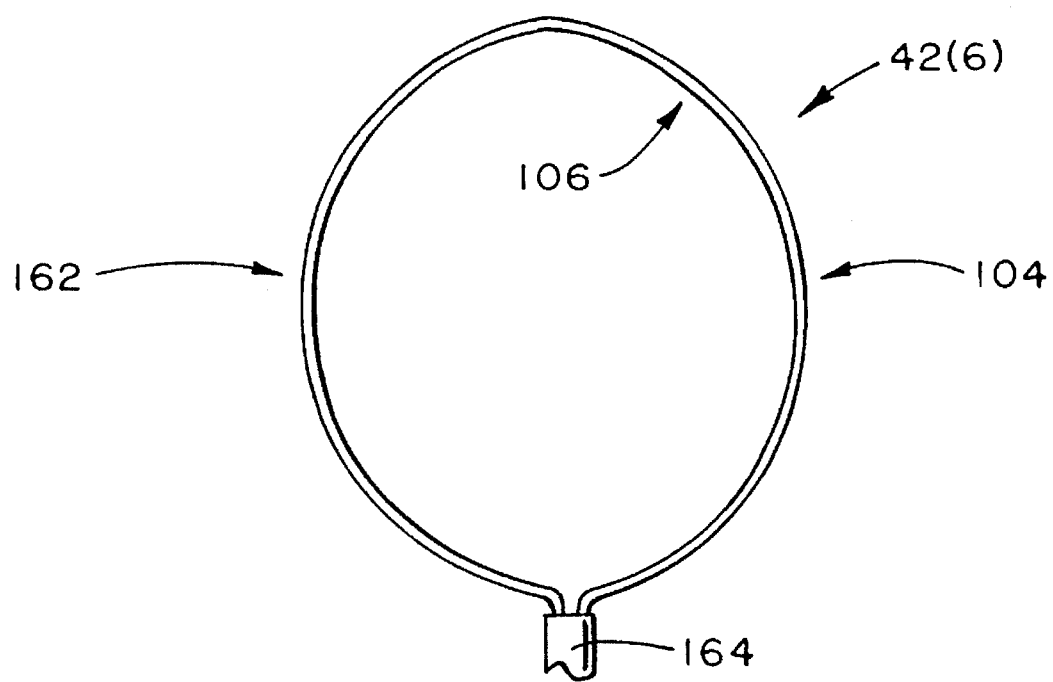
FIG. 13 is a plan view of an alternate ablating element that can be used to emit ablating energy to form curvilinear lesions within the atria of the heart.

FIG. 13 shows yet another alternative embodiment of an ablating element 42(6) that the ablation probe 66 can carry for introduction by the delivery system 44.

The alternative element 42(6) differs from the previously described multiple spline baskets 92(1) to (5) in that it forms a single hoop 162. The hoop 162 allows the physician to form, as part of the lesion pattern, lesions that substantially encircle the orifices of the SVC 26 and the IVC 28 in the right atrium 12 and the PV's 30 in the left atrium 14 (see FIG. 1). Furthermore, by using one or more hoops 162 in succession, the physician can eventually form an entire lesion pattern.

As before described, the hoop 162 can be made of a resilient inert material, like Nitinol metal or silicone rubber.

It extends from a base member 164 carried at the distal end of the catheter body of the associated ablating probe.

The hoop 162 can include electrically conductive regions 104 juxtaposed with electrically nonconductive regions 106, if needed. Alternatively, the hoop 162 can comprise a single, adjoining conductive region 104.

These regions 104 and 106 are located and formed on the hoop 162 using the same surface alteration techniques as before described.

As the baskets 92(1)/(2)/(3)/(4)/(5), the hoop 162 will resiliently collapse within the guide sheath 48 and resiliently spring open when deployed outside the guide sheath 48. In this way the hoop 162 can be collapsed for delivery into the atria 12/14 and then be deployed within the atria 12/14.

Figure 14:
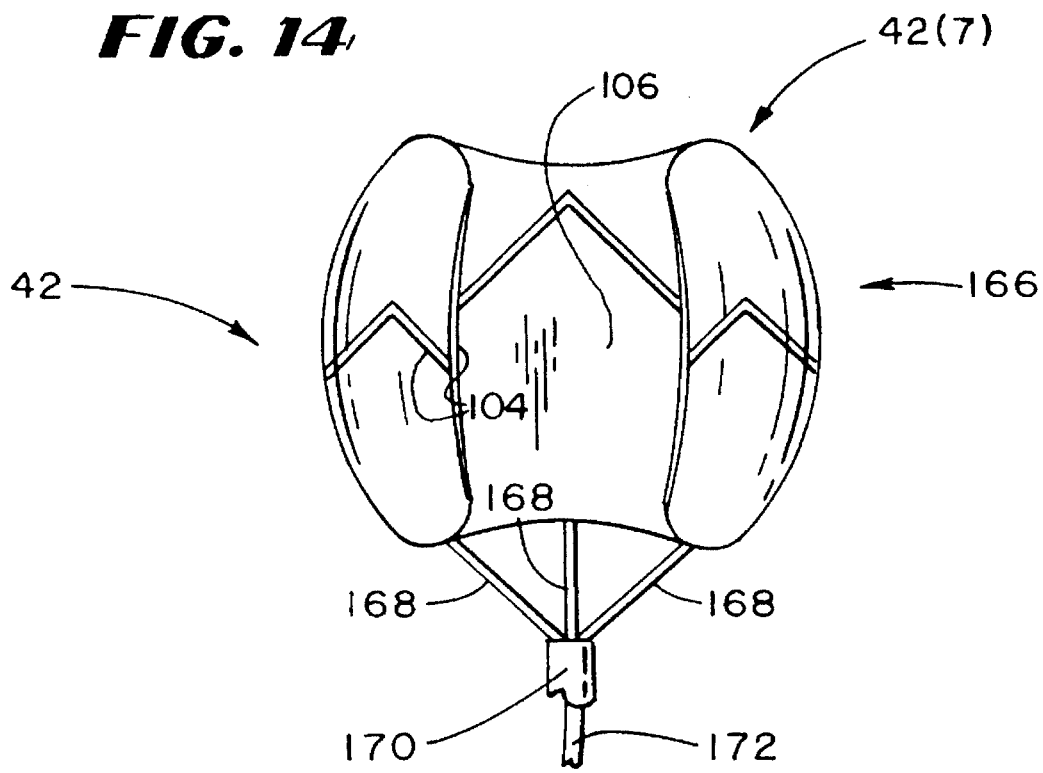
FIG. 14 is a plan view of an inflatable ablating element that can be used to emit ablating energy to form curvilinear lesions within the atria of the heart.

FIG. 14 shows yet another alternative embodiment of an ablating element 42(7) that the ablation probe 66 can carry for introduction by the delivery system 44.

This alternative element 42(7) differs from the previously described multiple spline baskets 92(1) to (5) and hoop 162 in that it comprises an inflatable balloon or bladder 166 made of a thermoplastic polymeric material, such as polyethylene. The bladder 166 is formed by either a free-blown process or a mold process.

The bladder 166 carries on its exterior surface a pattern of conduction regions 104 and nonconductive regions 106 to form the desired array of longitudinal and transverse lesions L.

In the illustrated and preferred embodiment, the conductive regions 104 are formed by coating the polymeric material of the bladder 166 with a conductive material. The nonconductive regions 106 are preserved free of the conductive material.

Coating of the conductive regions 104 may be accomplished by conventional sputter coating techniques. For example, gold can be sputtered onto the exterior surface of the bladder 166. Alternatively, a two phase sputter coating process may be employed in which an initial layer of titanium is applied followed by an outer coating of gold. The procedure may also use an ion beam assisted deposition (IBAD) process. This process implants the conductive material into the polymer of the bladder 166.

The conductive regions 104 of the bladder 166 are attached to signal wires (not shown) to conduct ablating energy to the conductive regions 104.

As with previously described elements 42, the difference in patterns in the right and left atria will require a particular pattern of conductive and nonconductive regions 104/106 for use in the right atrium 12 and another particular arrangement of conductive and nonconductive regions 104/106 for use in the left atrium 14.

As FIG. 14 shows, the element 42(6) includes one or more inflation lumens 168 that communicate with the interior of the bladder 166. The lumens 168 communicate with a common fluid supply tube 172 that extends through the bore of the catheter body 170 of the associated probe 66. As shown in phantom lines in FIG. 20, the supply tube 172 extends beyond the probe handle 84 to an injection port 174.

In use, the physician connects the port 174 to a source of fluid pressure (not shown), which is preferably a liquid such as water, saline solution, or the like. The bladder 166 is deployed in a collapsed position within the guide sheath 48 using the delivery system 44 already described. After maneuvering the distal end of the guide sheath 48 to the desired location within the right or left atria 12/14, the physician deploys the bladder 166 outside the guide sheath 48.

The physician then conducts positive fluid pressure through the supply tube 172 and lumen(s) 168 into the bladder 166. The positive fluid pressure causes the bladder 166 to expand or inflate.

Preferably, the inflation occurs under relatively low pressures of approximately 3–10 psi. The inflation is conducted to the extent that the bladder 166 is filled and expanded, but not stretched. The electrical conductivity of the conductive regions 104 on the bladder 166 is thus not disturbed or impaired. The inflating bladder 166 assumes a prescribed three-dimension shape, just as the baskets 92(1) to 92(5). The shape can vary, depending upon the shape of the bladder 166. In the illustrated embodiment, the bladder 166 assumes a toroidal shape, with an interior central opening to allow blood flow through it.

Due to its pliant nature, the bladder 166, when inflated, naturally conforms to the topography of the surrounding atria 12/14 surface, and vice versa, like the baskets 92(1) to 92(4).

By releasing the positive fluid pressure and applying negative pressure through the supply tube 172, the physician can drain fluid from the bladder 166. This collapses the bladder 166 for enclosure in the guide sheath 48 for maneuvering within the atria 12/14.

As before described, aided by the viewing probe 118 or other means of fluoroscopic or ultrasonic monitoring, the physician can maneuver the bladder 166 within the atria 12/14. Aided by the probe 118, the physician can repeatedly inflate and deflate the bladder 166 to deploy and withdraw the bladder 166 from and into the guide sheath 48, while rotating it within the guide sheath 48, until the desired orientation for the bladder 166 within the atria 12/14 is achieved.

The physician now takes steps to ablate the myocardial tissue areas contacted by the conducting regions 104 of the bladder 166. In this way, the physician forms the desired pattern of lesions L in the atria 12/14.

Release of the positive fluid pressure and the application of negative pressure through the supply tube 172 collapses the bladder 166 for enclosure in the guide sheath 48 and removal from the atria 12/14.

Category 2

Curvilinear Ablating Elements

FIGS. 27 to 55 show structures representative of Category 2 Curvilinear Ablating Elements 42 that the probes 66 can carry. Elements 42 in this category comprise a family of flexible, elongated ablating elements 176 (1) to (5) of various alternative constructions. In the preferred and illustrated embodiments, each element 176 is about 1 to 2.5 mm in diameter and about 1 to 5 cm long.

As FIG. 27 shows, each ablating element 176 is carried at the distal end of a catheter body 178 of an ablating probe 180. The ablating probe 180 includes a handle 184 at the proximal end of the catheter body 178. The handle 184 and catheter body 178 carry a steering mechanism 182 for selectively bending or flexing the ablating element 176 along its length, as the arrows in FIG. 27 show.

The steering mechanism 182 can vary. In the illustrated embodiment, the steering mechanism 182 is like that shown in FIG. 13. The steering mechanism 182 includes a rotating cam wheel 76 with an external steering lever 186. As FIG. 13 shows, the cam wheel holds the proximal ends of right and left steering wires 80. The wires 80 pass through the catheter body 178 and connect to the left and right sides of a resilient bendable wire or spring within the ablating element 176.

As FIG. 27 shows, forward movement of the steering lever 186 flexes or curves the ablating element 176 down. Rearward movement of the steering lever 186 flexes or curves the ablating element 176 up.

In this way the physician can flex the ablating element 176 in either direction along its length. Through flexing, the ablating element 176 is made to assume a multitude of elongated shapes, from a generally straight line to a generally arcuate curve, and all intermediate variable curvilinear shapes between. Through flexing, the ablating element 176 can also be brought into intimate contact along its entire ablating surface against the surface of the atrial wall to be ablated, despite the particular contours and geometry that the wall presents.

One or more signal wires (not shown) attached to the ablating element 176 extend through the catheter body 178 and terminate with an external connector 188 carried by the handle 184. The connector 188 plugs into a source of ablating energy (also not shown) to convey the ablating energy to the element 176.

By first remotely flexing the element 176 into the desired curvilinear shape and then applying ablating energy to it, the physician can form both elongated straight lesions and virtually an infinite variety of elongated, curvilinear lesions.

In use, the probe 180 and associated flexible ablating element 176 is introduced into the atria 12/14. Aided by the internal viewing probe 118 or another means of fluoroscopic or ultrasonic monitoring, the physician manipulates the steering lever 186 to steer the probe 180 into the desired atrial region.

For entry into the right atrium 12, the physician can direct the probe 180 through a conventional vascular introducer through the path shown in FIGS. 18 and 19, without using the delivery system 44. For entry into the left atrium 14, the physician can direct the probe 180 through a conventional vascular introducer retrograde through the aortic and mitral valves. Preferably, however, the physician can use the delivery system 44 to simplify access into the left atrium 14, in the manner shown in FIGS. 25 and 26.

Once in the desired region, the physician uses the same steering lever 186 to remotely bend the element 176 into the desired straight or curvilinear shape into intimate contact with the surrounding atrial wall. By then applying ablating energy to the shaped element 176, the physician forms a lesion that conforms to that shape.

By repeating this "shape-and-ablate" process within the atria 12/14, the physician eventually forms a contiguous pattern of straight and curvilinear lesions along the interior atrial surfaces. These lesions form the same desired patterns of longitudinal and transverse lesions that the three dimensional Category 1 Elements form all at once.

A single variable curvature ablating element 176 can be deployed within atria of various sizes and dimensions. Furthermore, a single variable curvature ablating element 176 can be used to form a multitude of different lesion patterns for the treatment of atrial fibrillation. Therefore, a single variable curvature ablating element 176 possesses the flexibility to adapt to different atrial geometries and pathologies.

The flexible, elongated ablating element 176 can also be used with a Category 1 Element to "touch up" or perfect incomplete lesions patterns formed by the Category 1 Element.

FIG. 28 shows one preferred embodiment of a flexible, elongated ablating element 176(1). The element 176(1) comprises a flexible body 190 made of a polymeric material, such as polyethylene. As shown by solid and phantom lines in FIG. 28, the body 190 can be flexed to assumed various curvilinear shapes, as just described.

The body 190 carries on its exterior surface a pattern of closely spaced electrically conductive regions 192. The conductive regions 192 can be formed by coating the polymeric material of the body 190 with a conductive material. The portions 194 of the body 192 between the conductive regions 192 are preserved free of the conductive material. These regions 194 are thereby electrically nonconductive.

Coating of the conductive regions 192 may be accomplished by conventional sputter coating techniques, using gold, for example. Alternatively, an initial layer of titanium can be applied followed by an outer coating of gold using an ion beam assisted deposition (IBAD) process.

Alternatively, the regions 192 can comprise metallic rings of conductive material, like platinum. In this embodiment, the rings are pressure fitted about the body 190, which is made from a nonconductive flexible plastic material, like polyurethane or polyethylene. The portions of the body 190 between the rings comprise the nonconductive regions 194.

The conductive regions 192 of the body 190 are attached to signal wires (not shown) to conduct ablating energy to one or more of the conductive regions 192.

The conductive regions 192 can be operated in a unipolar ablation mode, as FIG. 29 shows, or in a bipolar ablation mode, as FIG. 30 shows. In the unipolar ablation mode (as FIG. 29 shows), each conductive region 192 individually serves as an energy transmitting electrode. The energy transmitted by each conductive region 192 flows to an external indifferent electrode on the patient (not shown), which is typically an epidermal patch. In this mode, each conductive region 192 creates its own discrete lesion. However, due to the close spacing of the conductive regions 192, the lesions overlap to create a single adjoining lesion pattern.

In the bipolar ablation mode (as FIG. 30 shows), the conductive regions 192 are configured as alternating polarity transmitting electrode regions. A first region is designated "+" and a second region is designated "−". In this mode, ablating energy flows between the "+" electrode regions and the "−" electrode regions. This mode creates lesions that span adjacent electrode regions. As in the unipolar mode, the lesions overlap to form a single adjoining lesion pattern.

Figure 31:
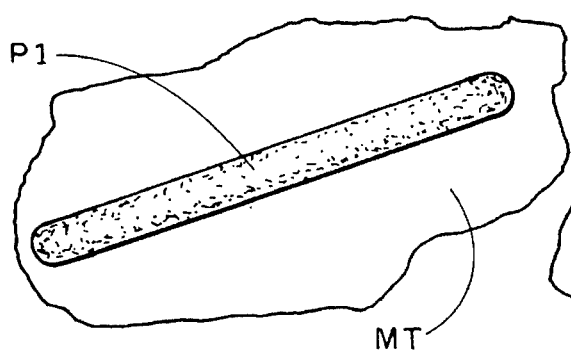
FIG. 31 shows, in somewhat diagrammatic form, a generally straight adjoining lesion pattern that can be formed by the element shown in FIGS. 28 to 30.
Figure 32:
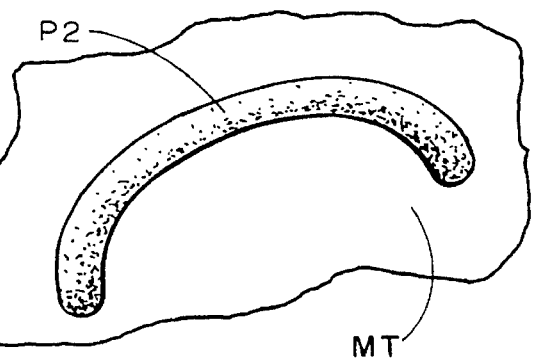
FIG. 32 shows, in somewhat diagrammatic form, a curvilinear adjoining lesion pattern that can be formed by the element shown in FIGS. 28 to 30.

When operated in either the unipolar ablation mode or the bipolar ablation mode, the element 176(1) forms a contiguous lesion pattern P in myocardial tissue MT along the particular curvature of the body 190. Depending upon the curvature of the body 190, the formed lesion pattern P1 in the tissue MT can be straight (as FIG. 31 shows), or the formed lesion pattern P2 in the tissue MT can be curved (as FIG. 32 shows). Both lesion patterns P1 and P2 result from the conformation between the atrial wall and the body 190.

The element 176(1) operates with higher impedance, higher efficiencies, and is more sensitive to tissue contact when operated in the bipolar ablation mode than when operated in the unipolar mode.

The lesion pattern created is approximately twice as wide as the body 190. The lesion pattern can be made wider by using wider conductive regions 192.

In a representative embodiment, the body 190 is about 2.5 mm in diameter. Each conductive region 192 has a width of about 3 mm, and each nonconductive region 194 also has a width of about 3 mm. When eight conductive regions 192 are present and activated with 30 watts of radiofrequency energy for about 30 seconds, the lesion pattern measures about 5 cm in length and about 5 mm in width. The depth of the lesion pattern is about 3 mm, which is more than adequate to create the required transmural lesion (the atrial wall is generally less than 2 mm).

Furthermore, by selectively not activating one or more adjacent regions 192, one can create a lesion pattern that is not adjoining, but is interrupted along the length of the body 190. The interruptions in the lesion pattern provide pathways for propagating the activation wavefront and serve to control pulse conduction across the lesion pattern.

Figure 33:
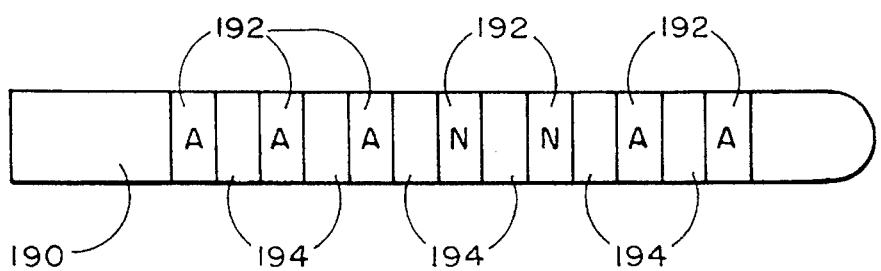
FIG. 33 show the flexible, elongated ablating element shown in FIG. 28 that includes an alternating pattern of conductive regions and non-conductive regions that can form an interrupted pattern of lesions in myocardial tissue.
Figure 34:
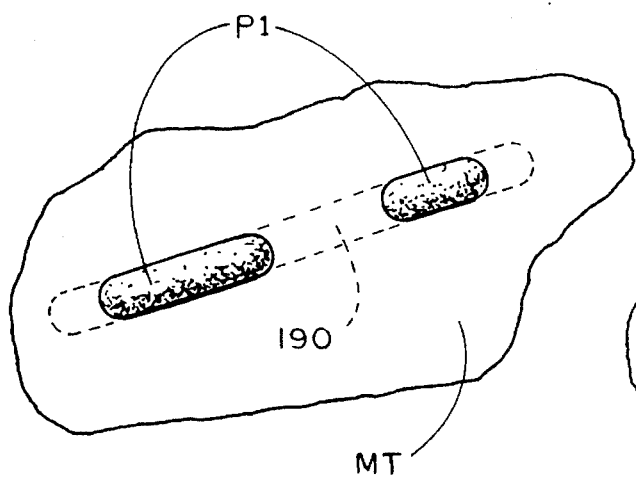
FIG. 34 shows, in somewhat diagrammatic form, an interrupted lesion pattern that can be formed by the element shown in FIG. 33.

For example, as FIG. 33 shows, the body 190 includes an alternating pattern of conductive regions 192 and nonconductive regions 194, each region 192/194 being of equal width. By activating some conductive regions 192 (showed by "A" in FIG. 33), while not activation other conductive regions (showed by "N" in FIG. 33), an interrupted pattern of lesions PI can be made in myocardial tissue MT, as FIG. 34 shows. As FIG. 34 also shows, lesions of different length can be formed along the interrupted pattern PI, depending upon the number of adjacent conductive regions 192 activated.

Figure 35:
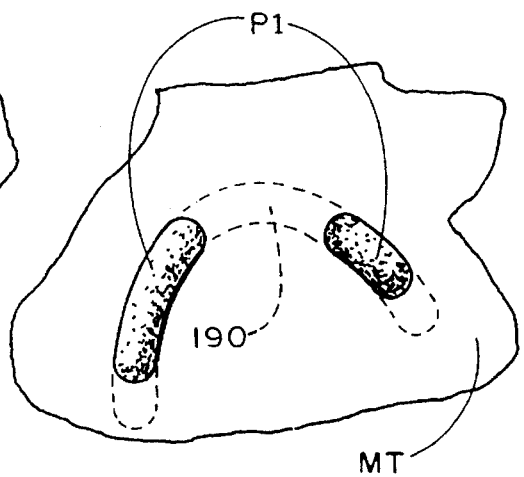
FIG. 35 shows, in somewhat diagrammatic form, an interrupted curvilinear lesion pattern that can be formed by the element shown in FIG. 33.

Of course, by varying the curvature of the body 190, the interrupted pattern PI can assume a generally straight path (as FIG. 34 shows), or it can assume a generally curved path, as FIG. 35 shows.

Figure 59:
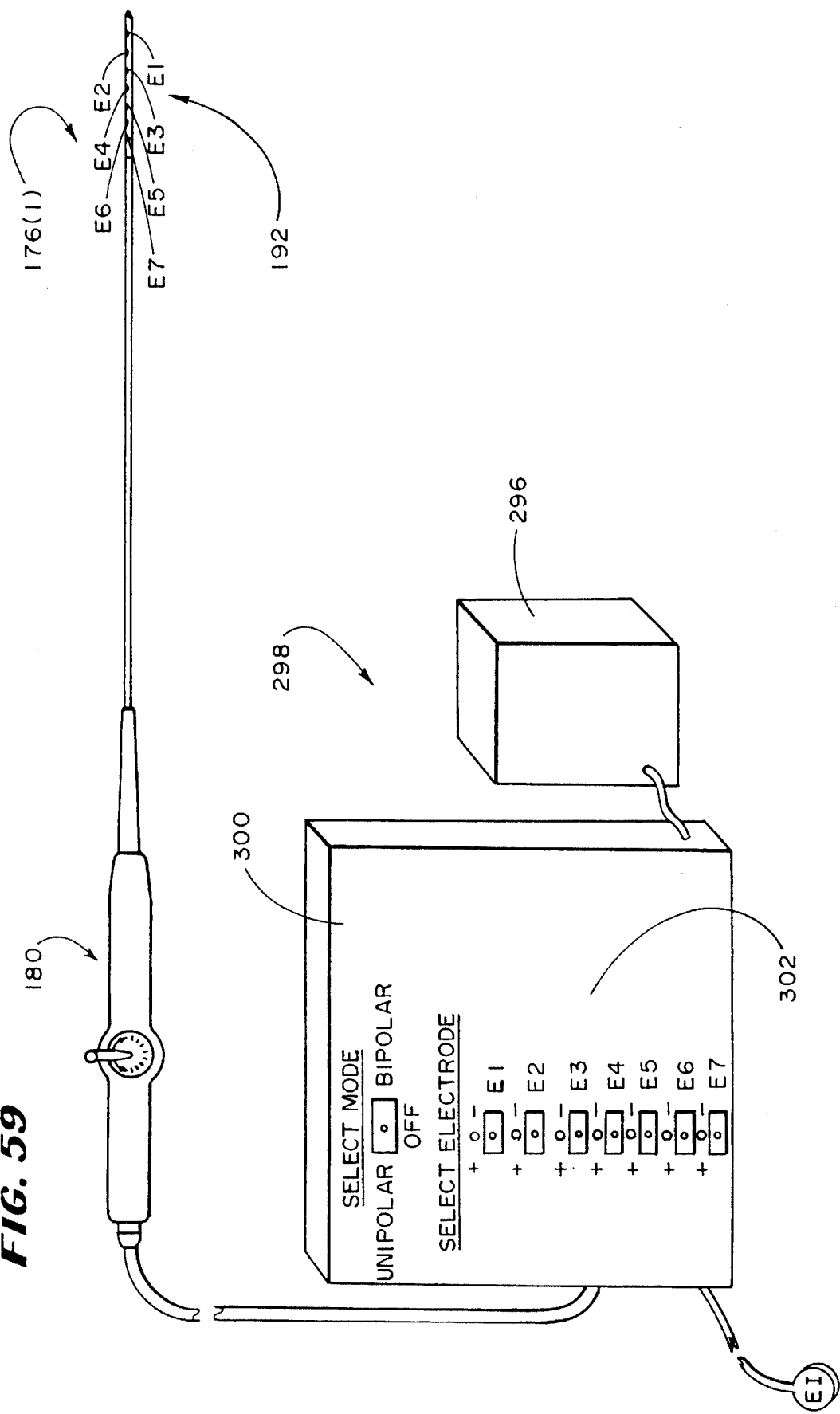
FIG. 59 is a partially diagrammatic view of a system for supplying ablating energy to the element shown in FIG. 28, which includes a controller that electronically adjusts and alters the energy emitting characteristics of the element.

FIG. 59 shows a system 298 that couples an ablating energy source 296 to the energy emitting region 192 of the element 176(1). In the illustrated embodiment, the source 296 supplies electromagnetic radiofrequency (RF) energy to the region 192.

The system 298 includes a controller 300. The controller 300 electronically adjusts and alters the energy emitting characteristics of the energy emitting region 192.

The controller 300 can electronically configure the energy emitting region 192 for operation in either a bipolar ablating mode or a unipolar ablating mode.

The controller 300 also can electronically configure the energy emitting region 192 to form lesion patterns having differing physical characteristics. In one mode, the controller 300 configures the energy emitting region 192 to form the continuous lesion pattern P1/P2 shown in FIGS. 31 and 32. In another mode, controller 300 configures the energy emitting region 192 to form a variety of interrupted lesion patterns PI, one of which is shown FIGS. 34 and 35.

The controller 300 includes an input panel 302 for governing the operation of the controller 300. Through the input panel 302, the physician chooses the ablation mode and physical characteristics of the lesion patterns. In response, the controller 300 electronically configures the energy emitting region 192 to operate in the chosen manner. In this way, the system 298 provides the flexibility to choose and then electronically create specially shaped lesions virtually instantaneously (i.e., "on the fly") during an ablation procedure.

Figure 60:
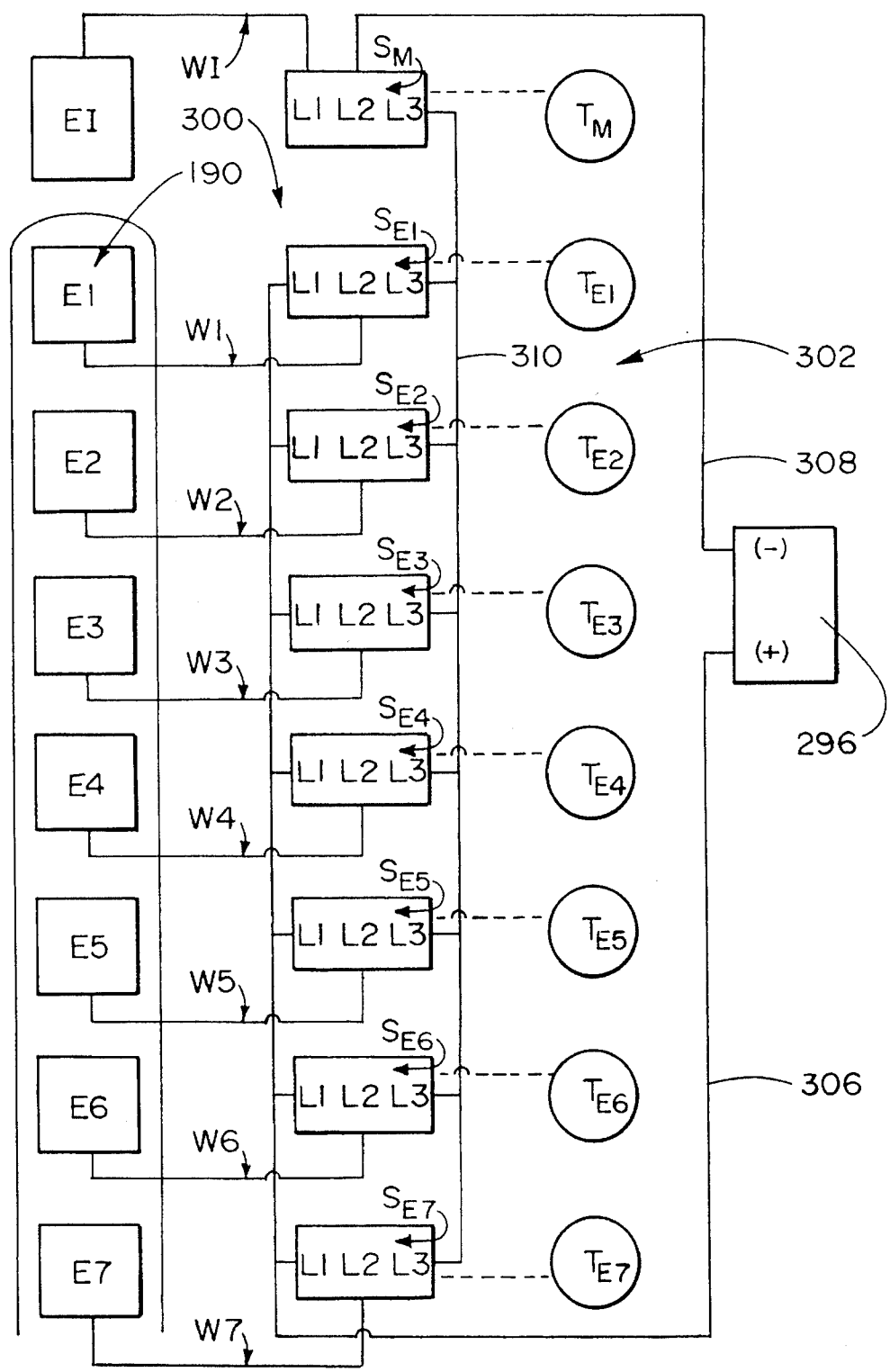
FIG. 60 is a schematic view of the controller and associated input panel shown in FIG. 59.

The configuration of the controller 300 and associated input panel 302 can vary. FIG. 60 diagrammatically shows one preferred arrangement.

In FIG. 60, the element 176(1) includes seven conductive regions, designated E1 to E7, carried on the body 190. Each conductive region E1 to E7 is electrically coupled to its own signal wire, designated W1 to W7. The indifferent electrode, designated E1 in FIG. 60, is also electrically coupled to its own signal wire W1.

In this arrangement, the controller 300 includes a switch $S_M$ and switches $S_{E1}$ to $S_{E7}$ that electrically couple the source 296 to the signal wires W1 to W7. The switch $S_M$ governs the overall operating mode of the regions E1 to E7 (i.e., unipolar or bipolar). The switches $S_{E1}$ to $S_{E7}$ govern the activation pattern of the regions 192.

Each switch $S_M$ and $S_{E1\ to\ E7}$ includes three leads L1; L2; and L3. Electrically, each switch $S_M$ and $S_{E1\ to\ E7}$ serves as three-way switch.

The three-way switches $S_M$ and $S_{E1\ to\ E7}$ are electrically coupled in parallel to the RF energy source 296. The (+) output of the RF source 294 is electrically coupled in parallel by a connector 306 to the leads L1 of the switches $S_{E1\ to\ E7}$. The (−) output of the RF source 294 is electrically directly coupled by a connector 308 to the center lead L2 of the mode selection switch $S_M$. A connector 310 electrically couples in parallel the leads L3 of the switches $S_M$ and $S_{E1\ to\ E7}$.

The center leads L2 of the selecting switch $S_{E1\ to\ E7}$ are directly electrically coupled to the signal wires W1 to W7 serving the energy emitting regions E1 to E7, so that one switch $S_{E(N)}$ serves only one energy emitting region $E_{(N)}$.

The lead L1 of the switch $S_M$ is directly electrically coupled to the signal wire WI serving the indifferent electrode EI.

The input panel 302 carries manually operable toggles $T_M$ and $T_{E1\ to\ E7}$. One toggle $T_M$ and $T_{E1\ to\ E7}$ is electrically coupled to one switch, respectively $S_M$ and $S_{E1\ to\ E7}$. When manipulated manually by the physician, each toggle $T_M$ and $T_{E1\ to\ E7}$ can be placed in three positions, designated A, B, and C in FIG. 61.

Figure 61:
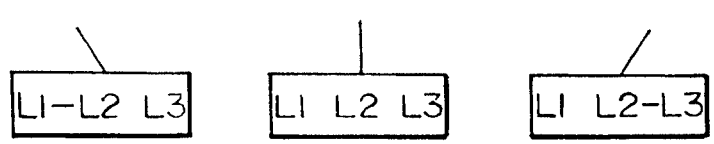
FIG. 61 is a schematic view of the toggle carried on the input panel shown in FIG. 60 in its three operative positions.

As FIG. 61 shows, toggle Position A electrically couples leads L1 and L2 of the associated switch. Toggle Position C electrically couples leads L2 and L3 of the associated switch. Toggle Position B electrically isolates both leads L1 and L3 from lead L2 of the associated switch.

Position B of toggle $T_M$ and toggles $T_{E1\ to\ E7}$ is an electrically OFF or INACTIVATED Position. Positions A and B of toggle $T_M$ and toggles $T_{E1\ to\ E7}$ are electrically ON or ACTIVATED Positions.

By placing toggle $T_M$ in its Position B (see FIG. 62), the physician electronically inactivates the controller 300. With toggle $T_M$ in Position B, the controller 300 conveys no RF energy from the source 296 to any region 192, regardless of the position of toggles $T_{E1\ to\ E7}$.

By placing toggle $T_M$ in Position A (see FIG. 63), the physician electronically configures the controller 300 for operation in the unipolar mode. With toggle $T_M$ in Position A, the center lead L2 of switch $S_M$ is coupled to lead L1, electronically coupling the indifferent electrode EI to the (−) output of the source 296. This configures the indifferent electrode EI to receive RF energy.

With toggle $T_M$ in Position A, the physician electronically configures the regions E1 to E7 to emit RF energy by placing the associated toggle $T_{E1\ to\ E7}$ in Position A (as FIG. 63 shows). This electronically couples each region E1 to E7 to the (+) output of the source 296, configuring the regions E1 to E7 to emit energy. The indifferent electrode EI receives the RF energy emitted by these regions E1 to E7.

With toggle $T_M$ in Position A and all toggles $T_{E1\ to\ E7}$ in their Positions A, a continuous, unipolar lesion pattern results, as FIG. 63 shows (like that shown in FIGS. 31 and 32).

With toggle $T_M$ in Position A, the physician can select to electronically interrupt the flow of RF energy one or more regions E1 to E7, by placing the associated toggles $T_{E1\ to\ E7}$ in Position B (see FIG. 64, where the flow is interrupted to regions E3 and E4). As FIG. 64 shows, this configuration forms lesions where the regions E1; E2; and E5 to E7 emit RF energy next to lesion-free areas where the selected region or regions E3 and E4 emit no RF energy. An interrupted, unipolar lesion pattern results (like that shown in FIGS. 34 and 35).

Placing toggle $T_M$ in Position C (see FIG. 65) electronically isolates the indifferent electrode EI from the regions E1 to E7. This configures the controller 300 for operation in the bipolar mode.

With toggle $T_M$ placed in Position C, the physician can electronically alter the polarity of adjacent energy emitting regions E1 to E7, choosing among energy emitting polarity (+), energy receiving polarity (−), or neither (i.e., inactivated).

Toggles $T_{E1\ to\ E7}$ placed in Position A electronically configure their associated regions E1 to E7 to be energy emitting (+). Toggles $T_{E1\ to\ E7}$ placed in Position C electronically configure their associated regions E1 to E7 to be energy receiving (−). Toggles $T_{E1\ to\ E7}$ placed in Position B electronically inactivate their associated regions E1 to E7.

With toggle $T_M$ in Position C, sequentially alternating the toggles $T_{E1\ to\ E7}$ between Positions A and C (as FIG. 65 shows) creates a continuous, bipolar lesion pattern. In FIG. 65, regions E1; E3; E5; and E7 are energy transmitting (+), and regions E2; E4; and E6 are energy receiving (−).

With toggle $T_M$ in Position C, moving selected one or more toggles $T_{E1\ to\ E7}$ to Position B (thereby inactivating the associated regions E1 to E7), while sequentially alternating the remaining toggles $T_{E1\ to\ E7}$ between Positions A and C (as FIG. 66 shows) creates an interrupted, bipolar lesion pattern. In FIG. 66, regions E3 and E4 are inactivated; regions E1; E5; and E7 are energy transmitting (+); and regions E2 and E6 are energy receiving (−).

Figure 36:
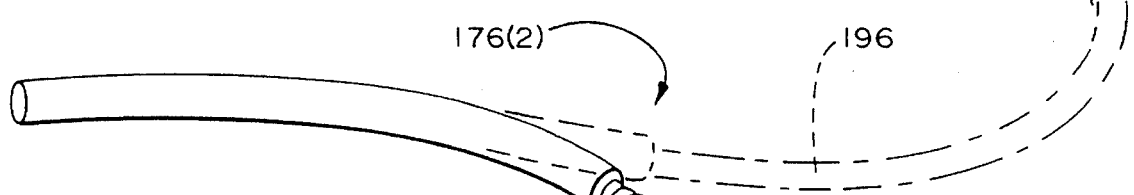
FIGS. 36 to 38 show another embodiment of a flexible, elongated ablating element that comprises a closely wound, single layer spiral winding.

FIG. 36 shows another preferred embodiment of a flexible, elongated ablating element 176(2). The element 176(2) comprises a flexible body core 196 made of a polymeric material, such as polyethylene or Teflon plastic. As shown by solid and phantom lines in FIG. 36, the core body 196 can be flexed to assumed various curvilinear shapes.

In this embodiment, the core body 196 carries a closely wound, spiral winding 198.

The winding 198 can comprise a single length of electrically conducting material, like copper alloy, platinum, or stainless steel. The electrically conducting material of the winding 198 can be further coated with platinum or gold to improve its conduction properties and biocompatibility.

The winding 198 can also comprise a single length of an electrically nonconducting material, to which an electrically conducting coating, like platinum or gold, has been applied.

The winding 198 can also comprise wound lengths of an electrically conducting material juxtaposed with wound lengths of an electrically nonconducting material. In this way, the winding 198 can form predetermined lesion patterns.

When attached to one or more signal wires (not shown), the regions of the winding 198 that comprise electrically conducting materials emit ablating energy. The winding 198 serves as an elongated flexible electrode that can be selectively flexed to form a diverse variety of long, curvilinear or straight lesion patterns.

Figure 37:
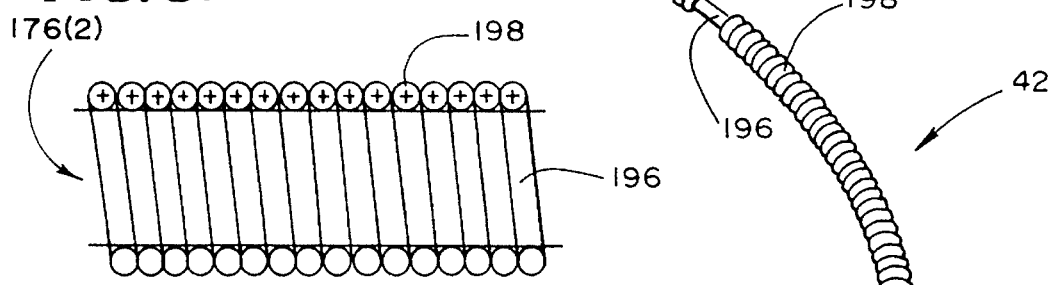
Figure 38:
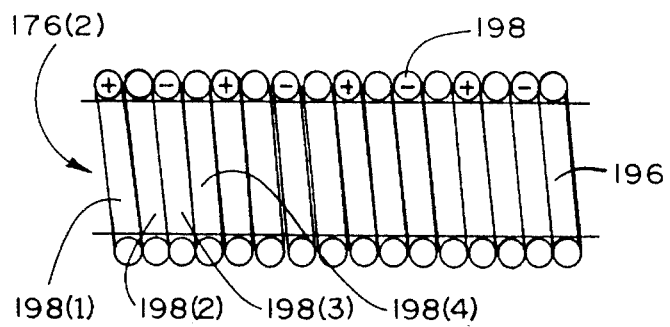

Like the element 176(1), the element 176(2) can be operated both in a unipolar ablation mode (as FIG. 37 shows) and in a bipolar ablation mode (as FIG. 38 shows).

In the unipolar ablation mode (as FIG. 37 shows), the winding 198 is formed from a single length of electrically conductive wire. The winding 198 serves as an energy transmitting electrode (as designated by a positive charge in FIG. 37). In this arrangement, the winding 198 transmits energy into the tissue and to an external indifferent electrode on the patient (not shown) to form a lesion.

In the bipolar ablation mode (as FIG. 38 shows), the winding 198 comprises four wrapped lengths of wire (designated 198(1); 198(2); 198(3); and 198(4) in FIG. 38). The wires 198(1) and 198(3) are each electrically conducting. The wire 198(2) and 198(4) are not electrically conducting. Instead, wires 198(2) and 198(4) serve to insulate the wires 198(1) and 198(3) from each other.

In the bipolar oblation mode, energy is applied to so that the turns of the wire 198(1) serve an energy transmitting regions (designated as "+"), while the turns of the wires 198(3) serve as energy receiving electrode regions (designated as "−").

In this mode, ablating energy flows from a transmitting electrode (positive) turn of wire 198(1) to an adjacent receiving electrode (negative) turn of wire 198(3), across the insulating intermediate wires 198(2) and 198(4).

Figure 39:
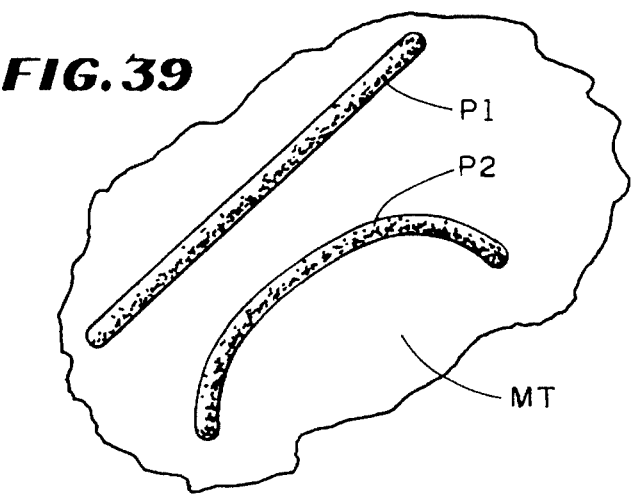
FIG. 39 shows, in somewhat diagrammatic form, adjoining lesion patterns, straight and curvilinear, which the element shown in FIGS. 36 to 38 can form.

When operated in either unipolar or bipolar mode, the element 176(2), like element 176(1), forms a contiguous lesion pattern P in myocardial tissue MT along the curvature of the body 196. As FIG. 39 shows, the lesion pattern P1 can follow a straight path, or the lesion pattern P2 can follow a curved path, depending upon the shape given to the body 96.

Element 176(2) allows the manufacture of a curvilinear ablation element of a smaller diameter than element 176(1). The smaller diameter allows for the creation of a contiguous lesion pattern of less width and depth. The small diameter of element 176(2) also makes it more flexible and more easily placed and maintained in intimate contact against the atrial wall than element 176(1).

In a representative embodiment, the element 176(2) is about 1.3 mm in diameter, but could be made as small as 1.0 mm in diameter. The element 176(2) is about 5 cm in total length. This element 176(2), when activated with 40 watts of radiofrequency energy for 30 seconds, forms a contiguous lesion pattern that is about 3 mm in width, about 5 cm in length, and about 1.5 mm in depth.

FIGS. 40 to 45 show yet another preferred embodiment of a flexible, elongated ablating element 176(3). Like the other elements 176(1) and 176(2), the element 176(3) comprises a flexible body core 200 made of a polymeric material, such as polyethylene. As shown by solid and phantom lines in FIGS. 40 and 43, the core body 200 can also be flexed to assumed various curvilinear shapes.

In this embodiment, the core body 200 carries one or more elongated, exposed strips 202 of flexible, electrically conducting material. Unlike the circumferential conductive regions 192 of element 176(1) and the circumferential winding 198 of the element 176(2), the strips 202(1) and 202(2) of element 176(3) run parallel along the axis of the core body 200.

As FIGS. 40 to 45 show, the parallel strips 202 and the underlying core body 200 can assume different shapes.

Figure 40:
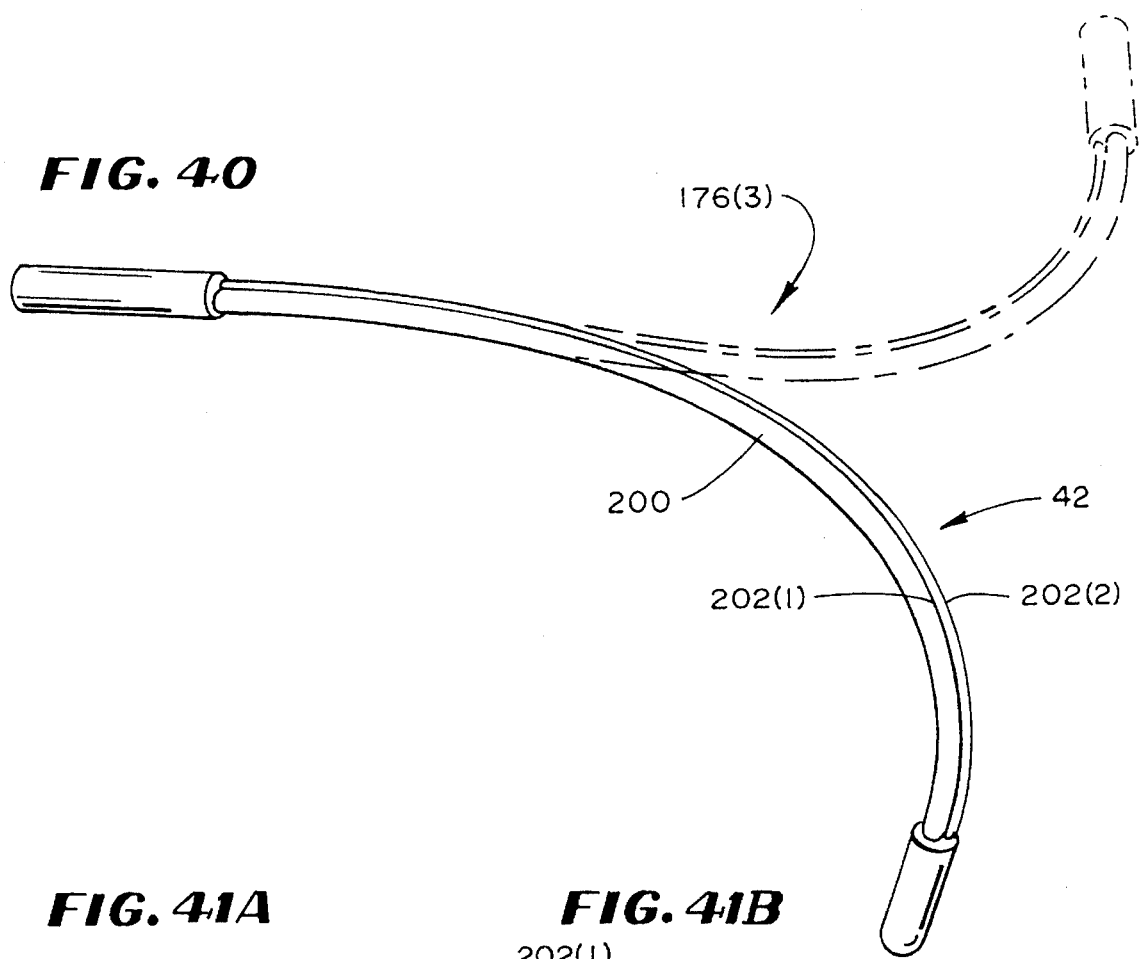
FIGS. 40 to 45 show a flexible, elongated ablating element that carries elongated strips of conductive material that can form curvilinear patterns of lesions in myocardial tissue.

In FIGS. 40 to 42, the core body 200 carries two strips, designated strip 202(1) and 202(2). These strips 202(1) and 202(2) are carried close to each other along the same surface region of the core body 200.

Figures 42A, 42B:
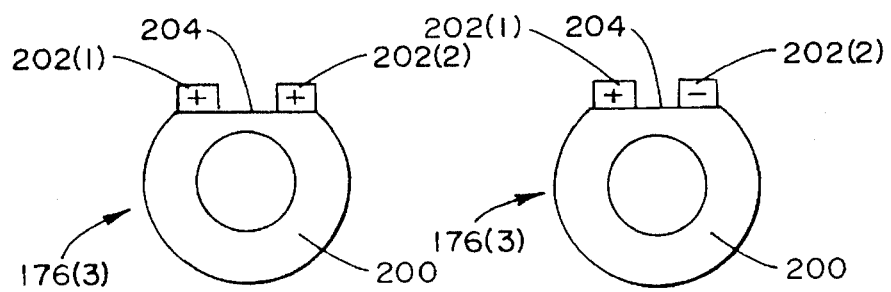
Figure 43:
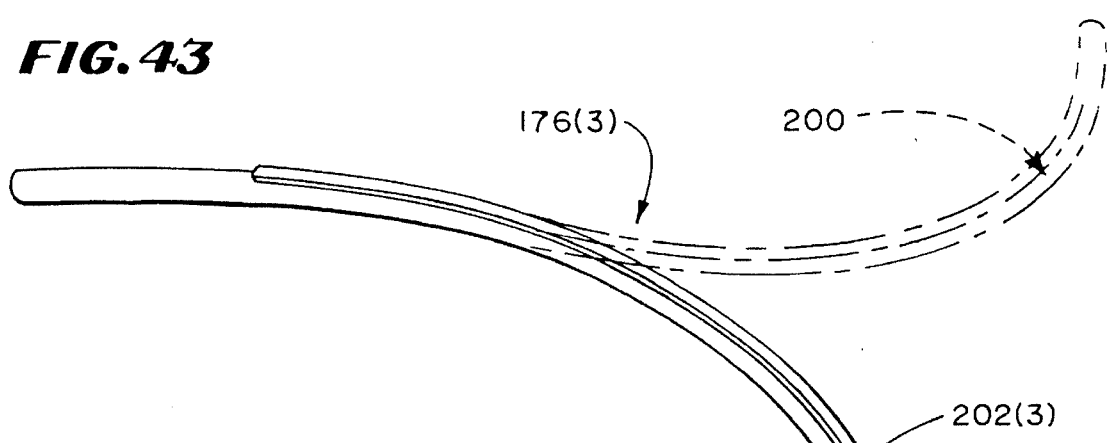

In FIG. 43, the core body 200 carries a single, elongated strip 200(3). This strip 202(3) has a larger surface area than the individual strips 202(1) and 200(2) (shown in FIGS. 40 to 42). However, as will be discussed later, the strip 202(3) can be operated only in a unipolar ablation mode (thereby requiring an external indifferent electrode), whereas the closely spaced pair of strips 202(1)/(2) can be operated in either a unipolar mode or a bipolar ablation mode.

Figure 44:
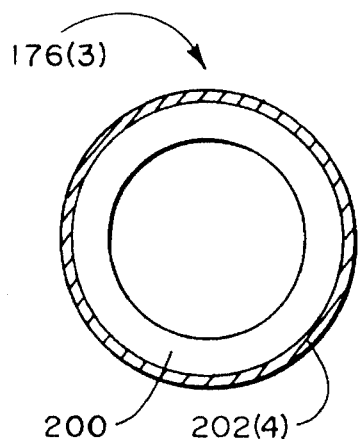
Figure 45:
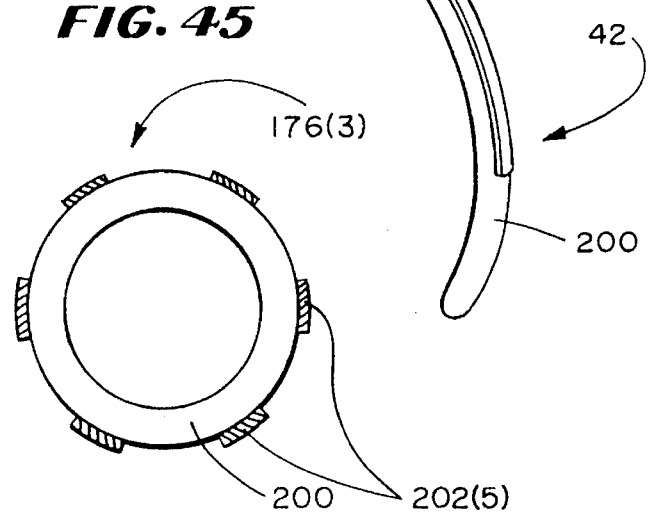

As FIGS. 44 and 45 show, strips 202(4) and strip 202(5) can occupy all or a significant portion of the core body 200.

In FIG. 44, the strip 200(4) covers the entire exterior surface of the core body 200. It therefore becomes an elongated variation of the circumferential regions 192 of element 176(1) and the circumferential winding 198 of the element 176(2).

In FIG. 45, multiple strips 200(5) segment the core body 200 into elongated conducting and nonconducting regions.

Figures 41A, 41B:
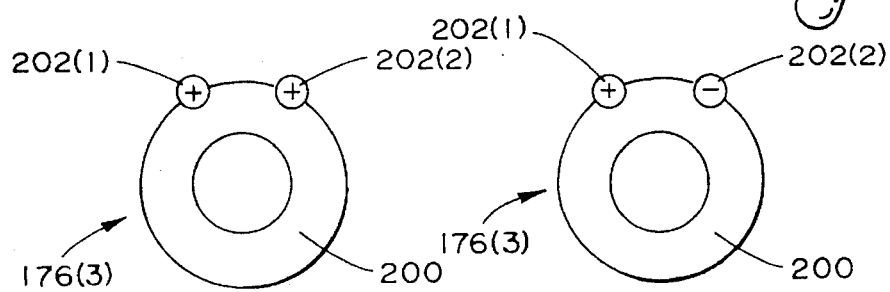

The strips 202 shown in FIGS. 40 to 45 can be affixed by adhesive or thermal bonding to the exterior surface of the core body 196, as FIGS. 41A/B and 43 to 45 show. Alternatively, the strips 200 can consist of coextruded elements of the core body 200 (as FIGS. 40 and 42A/B show).

The strips 202 can comprise elongated lengths of an electrically conducting material, like copper alloy. The strips can be further coated with platinum or gold to improve conduction properties and biocompatibility. The strips 202 can also comprise a single length of an electrically nonconducting material to which an electrically conducting coating, like platinum or gold, has been applied.

Alternatively, the strips 202 can comprise coatings applied by conventional sputter coating or IBAD techniques.

The strips 202 can also have differing cross sectional shapes. In FIGS. 41A/B, the strips 202(1) and 202(2) each have a circular cross section and thereby present a generally rounded contact zone with the tissue. The FIGS. 42A/B; 44; and 45, the strips 202 have a rectilinear cross section and thereby present a generally flat contact zone with the tissue.

As FIGS. 41A/B and 42A/B also show, the cross sectional shape of the underlying core body 200 can also vary. In FIGS. 41A/B, the core body 200 has a generally circular cross section. In FIGS. 42A/B, the core body 200 has a generally flattened region 204, upon which the strips 202(1) and 202(2) are laid. The flattened region 204 provides more stable surface contact.

The strips 202(1) and 202(2) can be operated in both a unipolar ablation mode (as FIGS. 41A and 42A show) and in a bipolar ablation mode (as FIGS. 41B and 42B show), depending upon the efficiencies required, as before discussed.

When operated in the unipolar mode (see FIGS. 41A and 42A), each strip 202(1)and 202(2) serves as elongated, flexible energy emitting electrode (designated with positive charges). The strips 202(3)/(4)/(5) (FIGS. 43 to 45) similarly operate as elongated flexible electrodes in the unipolar ablation mode.

When operated in the bipolar mode (see FIGS. 41B and 42B), one strip 202(1)/(2) serves as an elongated energy emitting electrode (designated with a positive charge), while the other strip serves as an elongated indifferent electrode (designated with a negative charge).

No matter its particular shape, the element 176(3) forms a contiguous, elongated lesion P in myocardial tissue MT arrayed along the curvature of the body 200.

Figure 46:
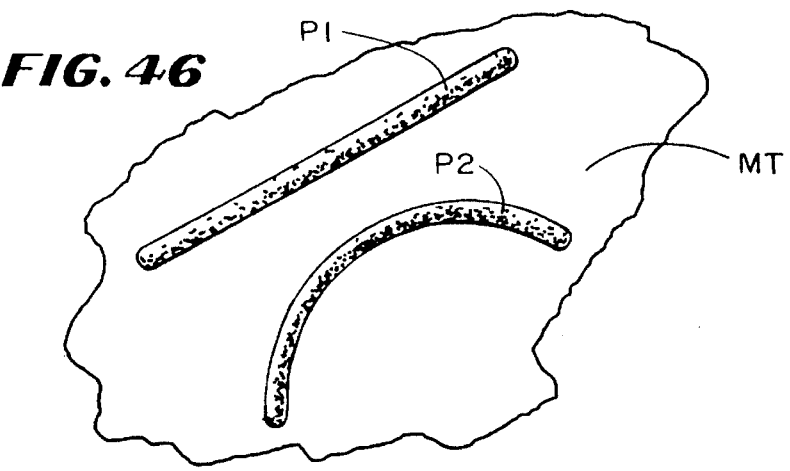
FIG. 46 shows, in somewhat diagrammatic form, adjoining lesion patterns, straight and curvilinear, which the element shown in FIGS. 40 to 45 can form.

As FIG. 46 shows, the lesion P1 in the tissue MT can follow a straight path, or the lesion P2 can follow a curved path, depending upon the shape of the body 200. In the multiple strip embodiments shown in FIGS. 40 to 42, the width of the lesion P1 or P2 can be controlled by the spacing between the strips 202(1)/(2) and 202(5). In the single strip embodiments shown in FIGS. 43 to 45, the width of the lesion P1 or P2 can be controlled by the width of the strips 202(3)/202(4)/202(5) themselves.

Figure 47:
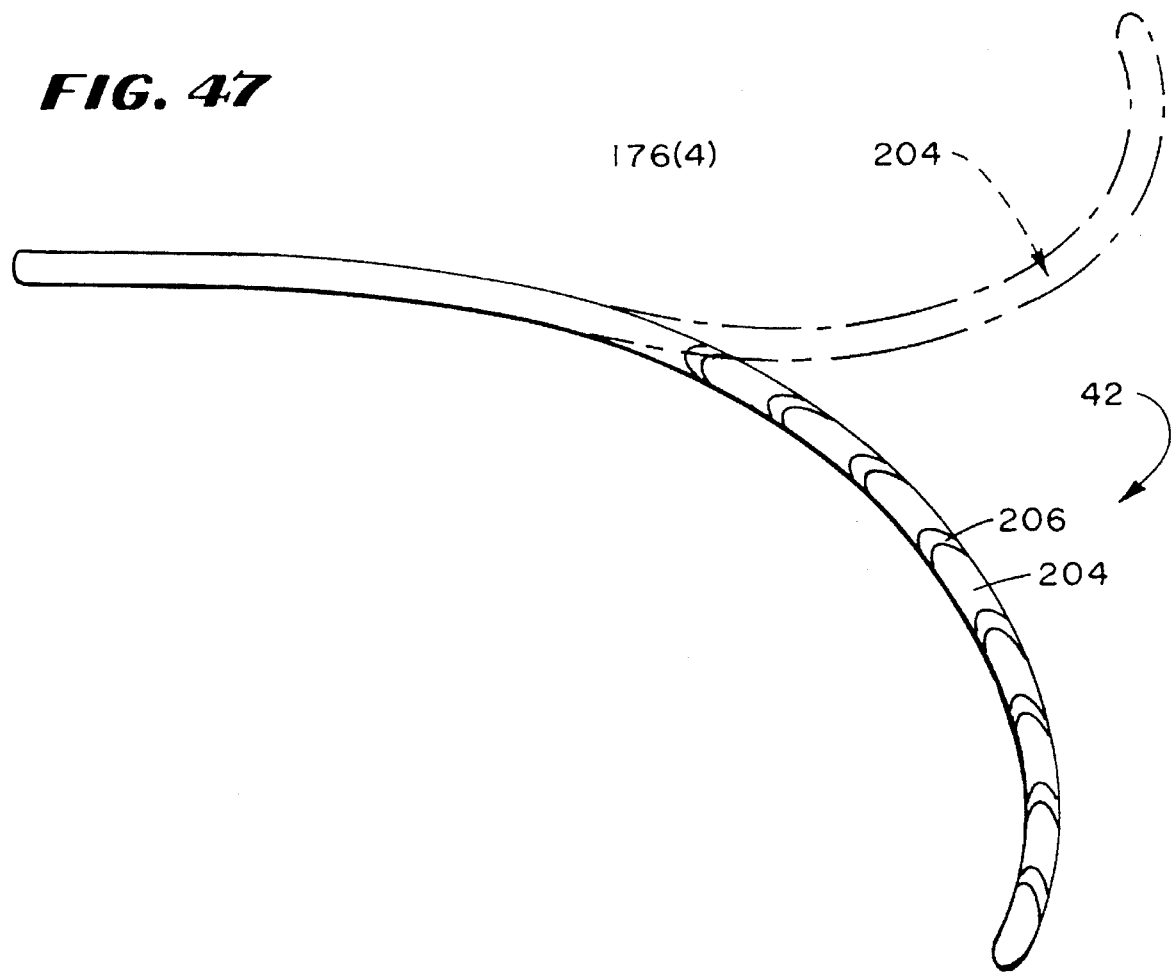
FIG. 47 and 48 show a flexible elongated ablating element that carries a thin, flat ribbon of spirally wound conductive material that can form curvilinear patterns of lesions in myocardial tissue.
Figure 48:
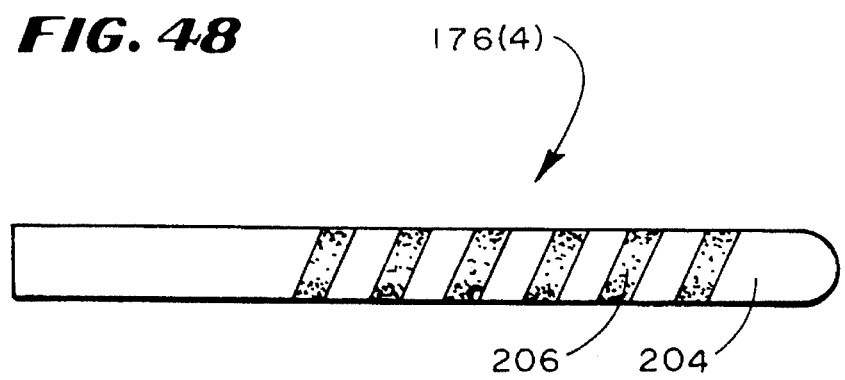

FIGS. 47 and 48 show still another preferred embodiment of a flexible, elongated ablating element 176(4). Like the other elements 176(1) to (3), the element 176(3) comprises a flexible body core 204 made of a polymeric material, such as polyethylene. As shown by solid and phantom lines in FIG. 40, the core body 204 can also be flexed to assumed various curvilinear shapes.

In this embodiment, a thin, flat ribbon 206 of material is spirally wound about and affixed to the core body 204.

The ribbon 206 comprises a polymeric material to which an electrically conducting coating, like platinum or gold, has been applied. Alternatively, the spiral electrically conductive ribbon 206 can be applied directly on the core body 204 using an ion beam assisted deposition (IBAD) process.

The spiral ribbon 206 serves as an elongated flexible electrode. Like the preceding element 176(1), the element 176(4) can be operated to emit ablating energy to form a pattern P1 or P2 of closely spaced lesions arrayed along the curvature of the body 204, as FIGS. 31 and 32 show. The element 176(4) can be operated only in a unipolar ablation mode in association with an external indifferent electrode.

FIGS. 49 and 50 show another preferred embodiment of a flexible, elongated ablating element 176(5). Unlike the other elements 176(1) to (4), the element 176(5) comprises a flexible body core 208 made of an electrically conducting material. As shown by solid and phantom lines in FIG. 42, the core body 208 can be flexed to assumed various curvilinear shapes.

In this embodiment, the core body 208 is partially enclosed by a shroud 210 made from an electrically non-conducting material, like polyethylene. The shroud 210 includes an elongated opening 212 that exposes the underlying core body 208. The shroud 210 electrically insulates the core body 208, except that portion 214 exposed through the opening 212.

When ablating energy is applied to the core body 208, only the portion 214 exposed through the window 212 emits energy. The rest of the shroud 214 blocks the transmission of the ablating energy to the tissue. The element 176(5) creates a continuous elongated ablation pattern, like that shown in FIG. 46 as created by the elongated strip 202(3) shown in FIG. 37.

Figure 51:
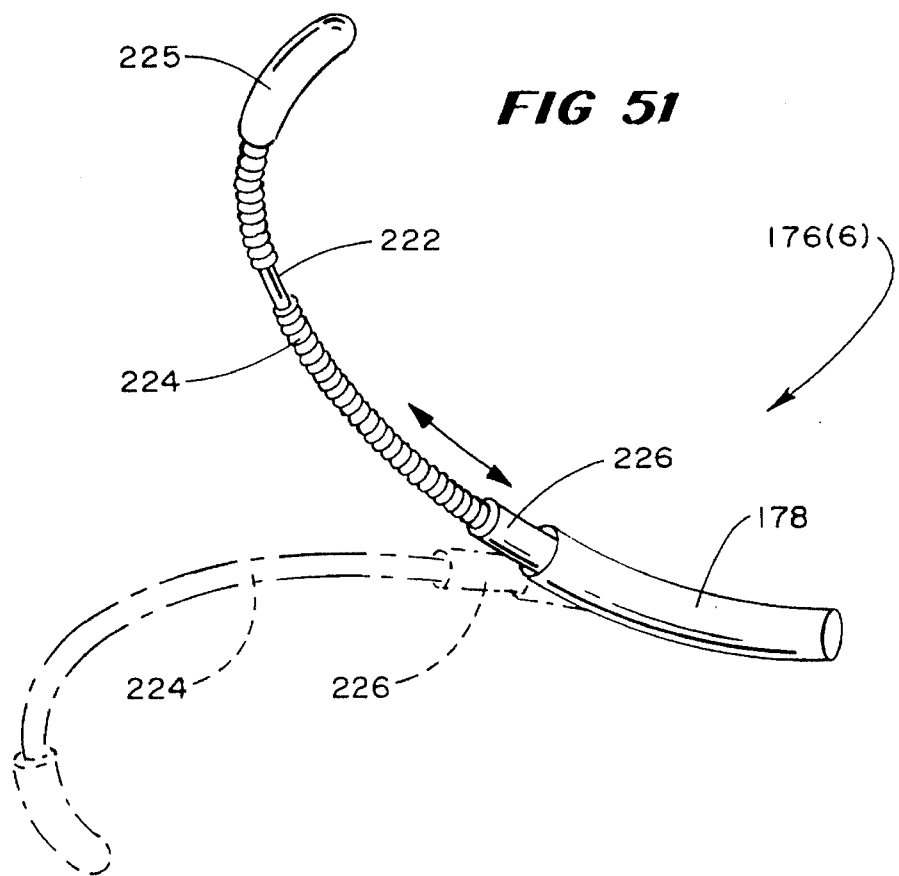

FIG. 51 shows an ablation probe 246 that carries another type of flexible, elongated ablating element 176(6). In many respects, the probe 246 is like the probe 180 shown in FIGS. 27 and 36.

The element 176(6) comprises a flexible body core 222 made of a polymeric material, such as polyethylene or Teflon plastic. The core 222 is carried at the distal end of the catheter body 248 of the associated probe 246.

Figure 55:
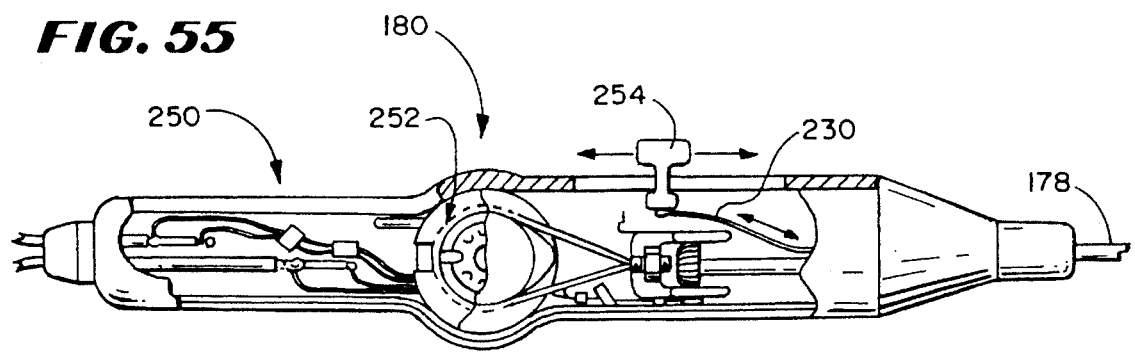
FIG. 55 shows a handle for the ablating element shown in FIGS. 51 to 54.

The probe 246 includes a handle 250 that carries a steering mechanism 252 for flexing the core body 222 into various curvilinear shapes, as shown by solid and phantom lines in FIG. 51. As FIG. 55 shows, the steering mechanism 252 is like the steering mechanism shown in FIG. 17, already described.

As FIG. 53 shows, the core body 222 carries a closely wound, spiral winding 224, like that shown in FIG. 36. The winding 224 comprises a single length of electrically conducting material, like copper alloy or platinum stainless steel. The electrically conducting material of the winding 224 can be further coated with platinum or gold to improve its conduction properties and biocompatibility.

Alternatively, the winding 224 can also comprise a single length of an electrically nonconducting material, to which an electrically conducting coating, like platinum or gold, has been applied.

When attached to one or more signal wires (not shown), the winding 224 emits ablating energy into the tissue and to an external indifferent electrode on the patient (not shown). The winding 224 thereby serves as an elongated flexible electrode that can be selectively flexed to form a diverse variety of long, curvilinear or straight lesion patterns, like those shown in FIG. 39.

Figure 52:
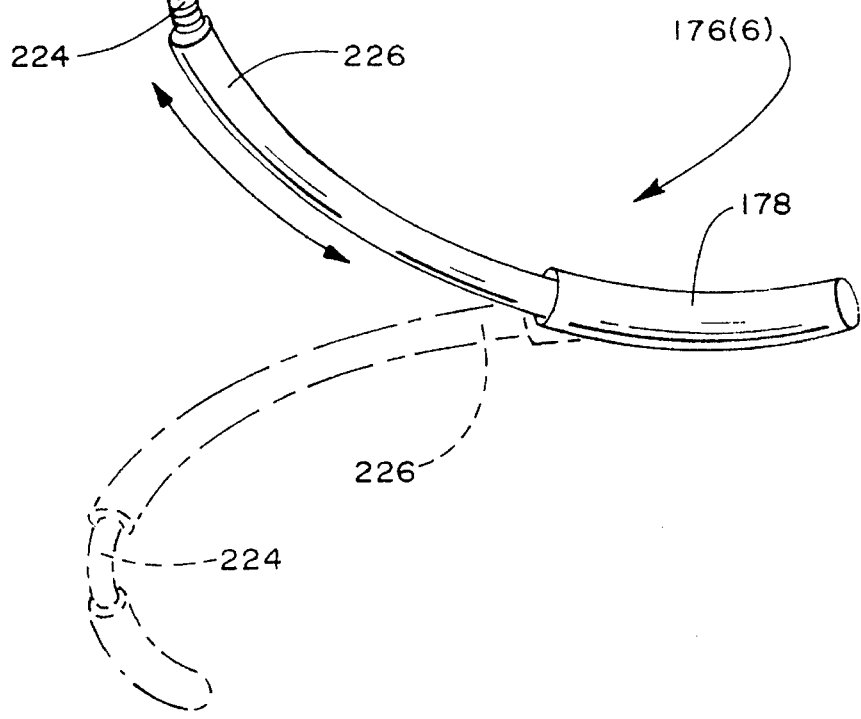

Unlike the element 176(2) shown in FIG. 36, the ablating element 176(6) includes a sliding sheath 226 carried about the winding 224 (see FIGS. 51 and 52). The sheath 226 is made of an electrically nonconducting material, like polyimide.

The interior diameter of the sheath 226 is greater than the exterior diameter of the winding 224, so it can be moved axially fore and aft along the exterior of the winding 224, as shown by the arrows in FIG. 52.

As FIG. 53 also shows, the sheath 226 carries a retaining ring 228 on its proximal end. A stylet 230 is attached to the retaining ring 228. The stylet 230 extends from the retaining ring 228, through the associated catheter body 248, and attaches to a sliding control lever 254 carried on the probe handle 250 (see FIG. 55).

Fore and aft movement of the control lever 254 (as arrows in FIG. 55 show) imparts, through movement of the stylet 230, fore and aft movement to the sheath 226 in a one-to-one relationship.

The sheath 226 carries a strip 234 of electrically conducting material at its distal end (see FIG. 53). The strip 234 includes a contact region 236 that extends through the sheath 226 to contact one or more turns of the underlying winding 224.

A signal wire 238 is electrically connected to the strip 234. The signal wire 238 conveys ablating energy from the source to the winding 224 through the contact region 236. The region 236 maintains electrical contact with the winding 224 during movement of the sheath 226.

The signal wire 238 and strip 234 are enclosed upon the sheath 226 by a layer of electrically insulating shrink tubing 240. A nonconducting adhesive is also used to electrically insulate the signal wire 238 and stylet 230 connections.

By moving the sheath 226 forward, the sheath 226 progressively covers more of the winding 224. Similarly, by moving the sheath 226 rearward, the sheath 226 progressively exposes more of the winding 224.

The impedance of the ablating element 176(6) varies with the area of the winding 224 exposed beyond the sheath 226. As progressively less area of the winding 224 is exposed beyond the sheath 226, the impedance of the ablating element 176(6) becomes progressively greater. Conversely, as progressively more area of the winding 224 is exposed beyond the sheath 226, the impedance of the ablating element 176(6) becomes progressively less.

By manipulating the control mechanism 232 on the handle 184, the physician can thereby remotely adjust the impedance of the ablating element 176(6). In this way, the physician gains direct control over the efficiency of the ablation process.

By moving the sheath 226 to expose more or less of the winding 224, the physician also gains direct control over the size of the ablating element 176(6) and, thus, over the size of the curvilinear lesion itself.

By selecting materials of different stiffness for the sheath 226, one can also alter the bending characteristics of the winding 224.

Figure 56:
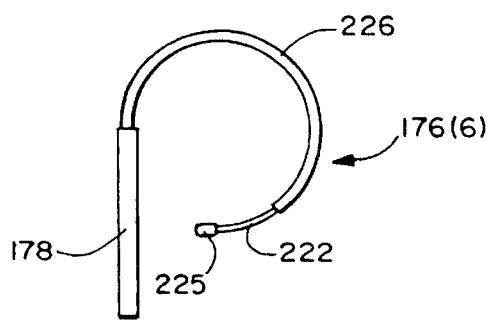
FIG. 56 shows a flexible, elongated ablation element, generally like that shown in FIGS. 51 to 54, with a sheath made of a non rigid material that is less flexible that the underlying element.

As FIG. 56 shows, when the sheath 226 is made of a non rigid material that less flexible that the underlying core body 222, movement of the sheath 226 over the core body 222 imparts more total stiffness to the body 222. In this way, the physician can alter the shape of the curvilinear lesion. The physician can also gain a greater degree of tissue contact with a stiffer flexible body 222.

Figure 57:
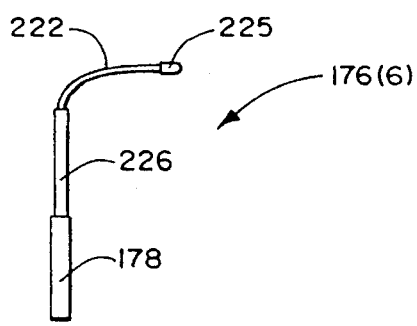
FIG. 57 shows a flexible, elongated ablation element, generally like that shown in FIGS. 51 to 54, with a sheath made of a relatively rigid material.

As FIG. 57 shows when the sheath 226 is made of a relatively rigid material, movement of the sheath 226 effectively changes the fulcrum point about which the body core 222 curves. The shape of the body 222, when flexed, therefore changes with movement of the sheath 226.

Further details regarding the concepts of using of a movable sheath to varying the flexing characteristics of a steerable catheter are revealed in copending patent application Ser. No. 08/099,843, filed Jul. 30, 1993 now U.S. Pat. No. 5,397,321, and entitled "Variable Curve Electrophysiology Catheter" and copending patent application Ser. No. 08/100,739, filed Jul. 30, 1993 and entitled "Variable Stiffness Electrophysiology Catheter."

In one preferred construction, the ablating element 176(6) is about 1.2 to 2.0 mm in diameter and about 5 cm long. The outer diameter of the catheter body 178 that carries the element 176(6) is about 7 French (one French is 0.33 mm). The contact strip 234 measures about 0.05 mm by 0.5 mm by 5 mm.

Figure 58:
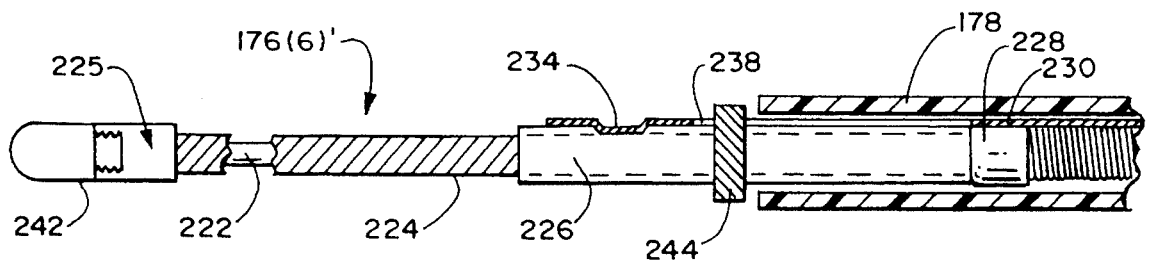
FIG. 58 shows a flexible, elongated alternation element, like that shown in FIGS. 51 to 54, except that it can be operated in a bipolar ablation mode to form curvilinear patterns of lesions in myocardial tissue.

FIG. 58 shows an alternative ablation element 176(6)', which can be operated in a bipolar ablation mode. The element 176(6)' shares many structural elements with the element 176(6) shown in FIGS. 51 to 54. The common structural elements are identified with the same reference numbers.

Unlike the element 176(6) shown in FIG. 51, the element 176(6)' shown in FIG. 58 includes an operative electrode 242 at the distal tip 225 of the core body 222. Also, unlike the element 176(6) in FIG. 51, the sheath 226 of the element 176(6) carries an operative electrode ring 244.

In use, the electrodes 242 and 24.4 can be maintained at one polarity, while the winding 224 is maintained at the opposite polarity. This arrangement makes operation in a bipolar ablation mode possible.

Therefore, along with all the benefits obtained by using the moveable sheath 226 (as already discussed concerning the element 176(6)), the element 176(6)' can also obtain the added benefits that bipolar mode operation provides.

The features of the invention are set forth in the following claims.

We claim:

1. A device for forming curvilinear lesions in tissue within the body comprising a source for generating ablating energy, a first energy emitting electrode connected to the source, and a second energy emitting electrode connected to the source, the second energy emitting electrode intersecting the first energy emitting electrode to form an angled junction between them creating, when ablating energy is emitted by the electrodes, an intersecting, curvilinear lesion pattern in the body tissue.

2. A device according to claim 1 wherein the electrodes are elongated and the curvilinear lesion pattern created is elongated in length.

3. A device according to claim 2 wherein the electrodes are elongated and the curvilinear lesion pattern created has a length to width ratio that is at least about 3:1.

4. A device according to claim 3 wherein the electrodes are elongated and the curvilinear lesion pattern created has a width that is no greater than about 5 mm.

5. A device according to claim 2 wherein the electrodes are elongated and the curvilinear lesion pattern created has a length to width ratio that is in the range of about 10:1 to 20:1.

6. A device according to claim 5 wherein the electrodes are elongated and the curvilinear lesion pattern created has a width that is no greater than about 5 mm.

7. A device according to claim 1 wherein the first and second energy emitting electrodes are mutually resilient for bending relative to each other when exposed to body tissue.

8. A device according to claim 1 wherein the intersecting energy emitting electrodes form a slidable point of contact at the angled junction to allow relative movement between the intersecting energy emitting electrodes at the angled junction.

9. A device according to claim 8 wherein the first and second energy emitting electrodes are mutually resilient for bending relative to each other when exposed to body tissue.

10. A device for forming compound curvilinear lesions in tissue within the body comprising a source for generating ablating energy, a first energy emitting electrode connected to the source, and a second energy emitting electrode connected to the source, the second energy emitting electrode intersecting the first energy emitting electrode to form a first angled junction, a third energy emitting electrode connected to the source, the third energy emitting electrode intersecting the first energy emitting electrode to form a second angled junction for creating, when ablating energy is emitted by the first, second, and third electrodes, an intersecting compound curvilinear lesion pattern in the body tissue.

11. A device according to claim 10 wherein the electrodes are elongated and the curvilinear lesion pattern created is elongated in length.

12. A device according to claim 11 wherein the electrodes are elongated and the curvilinear lesion pattern created has a length to width ratio that is at least about 3:1.

13. A device according to claim 12 wherein the electrodes are elongated and the curvilinear lesion pattern created has a width that is no greater than about 5 mm.

14. A device according to claim 10 wherein the electrodes are elongated and the continuous compound lesion pattern created has a length to width ratio that is in the range of about 10:1 to 20:1.

15. A device according to claim 14 wherein the electrodes are elongated and the continuous compound lesion pattern created has a width that is no greater than about 5 mm.

16. A device according to claim 15 wherein the electrodes are elongated and the continuous compound lesion pattern created has a width that is no greater than about 5 mm.

17. A device according to claim 10 wherein at least two of the first, second, and third energy emitting electrodes are mutually resilient for bending relative to each other when exposed to body tissue.

18. A device according to claim 10 wherein the intersecting energy emitting electrodes form a slidable point of contact at least one of the first and second angled junctions to allow relative movement between the intersecting energy emitting electrodes.

19. A device for creating curvilinear lesions in tissue within the body comprising a source for generating ablating energy, an array of main splines extending side by side in a spaced apart relationship to form a structure, at least one bridge spline extending between two main splines, the bridge spline intersecting one main spline to form an angled junction, a first region connected to the source for emitting energy on the one main spline, and a second region connected to the source for emitting energy on the bridge spline, said first energy emitting region on said main spline and said second energy emitting region on said bridge spline intersecting each other at the angled junction to create, when ablating energy is emitted by the regions, an intersecting curvilinear lesion pattern in the body tissue.

20. A device according to claim 19 wherein the one main spline and the bridge spline are resilient for bending relative to each other when exposed to body tissue.

21. A device according to claim 19 wherein the bridge spline is free to move relative to the one main spline at the angled junction.

22. A device according to claim 19 wherein the bridge spline is fixedly attached to the one main spline.

23. A device according to claim 19 wherein the main splines form a three-dimensional basket structure that encloses an open interior, and wherein the bridge spline is located within the open interior of the three-dimensional basket structure.

24. A device according to claim 23 wherein the bridge spline is part of a helical structure located within the open interior of the three-dimensional basket structure.

25. A device according to claim 23 wherein the bridge spline is steerable within the open interior of the three-dimensional basket structure.

26. A device according to claim 23 wherein the bridge spline is part of a three-dimensional structure located within the open interior of the three-dimensional basket structure.

27. A device according to claim 19 wherein the main splines form a three-dimensional basket structure that encloses an open interior, and wherein the bridge spline extends outside of the three-dimensional basket structure.

28. A device according to claim 27 wherein the bridge spline comprises a helical structure wrapped about the outside of the three-dimensional basket structure.

29. A device for creating curvilinear lesions in tissue within the body comprising a source for generating ablating energy, an array of main splines extending side by side in a spaced apart relationship to form a structure, at least one bridge spline extending between two main splines, the bridge spline intersecting one main spline to form a first angled junction and intersecting the other main spline to form a second angled junction, electrodes connected to the source for emitting energy on the two main splines, and an electrode connected to the source for emitting energy on the bridge spline, the energy emitting electrodes intersecting at the first and second angled junctions to create, when ablating energy is emitted by the electrodes, an intersecting compound curvilinear lesion pattern in the body tissue.

30. A device according to claim 29 wherein the two main splines and the bridge spline are resilient for bending relative to each other exposed to body tissue.

31. A device according to claim 29 wherein the bridge spline is free to move relative to the two main splines at the angled junctions.

32. A device according to claim 29 wherein the bridge spline is attached to the two main splines at the angled junctions.

33. A device according to claim 29 wherein the main splines form a three-dimensional basket structure that encloses an open interior, and wherein the bridge spline is located within the open interior of the three-dimensional basket structure.

34. A device according to claim 33 wherein the bridge spline is part of a helical structure located within the open interior of the three-dimensional basket structure.

35. A device according to claim 33 wherein the bridge spline is steerable within the open interior of the three-dimensional basket structure.

36. A device according to claim 33 wherein the bridge spline is part of a three-dimensional structure located within the open interior of the three-dimensional basket structure.

37. A device according to claim 29 wherein the main splines form a three-dimensional basket structure that encloses an open interior, and wherein the bridge spline extends outside of the three-dimensional basket structure.

38. A device according to claim 37 wherein the bridge spline comprises a helical structure wrapped about the three-dimensional basket structure.

39. A method for forming curvilinear lesions in tissue within the body comprising the steps of exposing tissue to an electrode array comprising a first energy emitting electrode and a second energy emitting electrode that intersects the first energy emitting electrode to form an angled junction between them, and applying ablating energy for emission by both elements to create an intersecting curvilinear lesion pattern in the tissue.

40. A method for forming compound curvilinear lesions in tissue within the body comprising the steps of exposing tissue to an electrode array comprising a first energy emitting electrode, a second energy emitting electrode that intersects the first energy emitting electrode to form an angled junction between them, and a third energy emitting electrode that intersects one of the first and second energy emitting electrodes at a second angled junction spaced from the first mentioned angled junction, and applying ablating energy for emission by the first, second, and third electrodes to create an intersecting compound curvilinear lesion pattern.

\* \* \* \* \*